US006262059B1

(12) United States Patent
Pamukcu et al.

(10) Patent No.: US 6,262,059 B1
(45) Date of Patent: Jul. 17, 2001

(54) METHOD OF TREATING A PATIENT HAVING PRECANCEROUS LESIONS WITH QUINAZOLINE DERIVATIVES

(75) Inventors: Rifat Pamukcu, Spring House, PA (US); Gary Piazza, Highlands Ranch, CO (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/055,829

(22) Filed: Apr. 6, 1998

Related U.S. Application Data

(63) Continuation of application No. 08/477,227, filed on Jun. 7, 1995, now abandoned.

(51) Int. Cl.[7] ................................................. A61K 31/505
(52) U.S. Cl. ............................................................ 514/260
(58) Field of Search .................................... 514/258, 260

(56) References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,460,590 | 7/1984 | Möller . |
| 4,460,591 | 7/1984 | DeGraw et al. . |
| 4,880,810 | 11/1989 | Lowe, III et al. . |
| 4,885,301 | 12/1989 | Coates . |
| 4,923,874 | 5/1990 | McMahon et al. . |
| 5,073,559 | 12/1991 | Coates . |
| 5,147,875 | 9/1992 | Coates et al. . |
| 5,223,501 | 6/1993 | Chakravarty et al. . |
| 5,250,535 | 10/1993 | Verheyden et al. . |
| 5,254,571 | 10/1993 | Coates et al. . |
| 5,358,952 | 10/1994 | Moschel et al. . |
| 5,401,774 | 3/1995 | Pamukcu et al. . |
| 5,439,895 | 8/1995 | Lee et al. . |
| 5,614,530 | 3/1997 | Kumar et al. . |
| 5,614,627 | 3/1997 | Takase et al. . |
| 5,696,159 | 12/1997 | Gross et al. . |

FOREIGN PATENT DOCUMENTS

| | | |
|---|---|---|
| 3038166 | 5/1981 | (DE) . |
| 0 347146 A2 | 12/1989 | (EP) . |
| 274218 | 12/1989 | (DE) . |
| 0 349239 A2 | 1/1990 | (EP) . |
| 0 351058 | 1/1990 | (EP) . |
| 0 352 960 A2 | 1/1990 | (EP) . |
| 0 395328 A2 | 10/1990 | (EP) . |
| 0 428268 A2 | 5/1991 | (EP) . |
| 0 463756 A1 | 1/1992 | (EP) . |
| 0 485157 A2 | 5/1992 | (EP) . |
| 0 485158 A2 | 5/1992 | (EP) . |
| 0 485171 A2 | 5/1992 | (EP) . |
| 0 485172 A2 | 5/1992 | (EP) . |
| 0 485173 A2 | 5/1992 | (EP) . |
| 0 508586 A1 | 10/1992 | (EP) . |
| 0 526004 A1 | 2/1993 | (EP) . |
| 0 607 439 A1 | 7/1994 | (EP) . |
| 807826 | 1/1959 | (GB) . |
| 2063249 | 6/1981 | (GB) . |
| 56-53659 | 5/1981 | (JP) . |
| 57-167974 | 10/1982 | (JP) . |
| WO 92/03419 | 3/1992 | (WO) . |
| WO 93/07149 | 4/1993 | (WO) . |
| WO 93/12095 | 6/1993 | (WO) . |
| WO 94/05661 | 3/1994 | (WO) . |
| WO 95/19978 | 7/1995 | (WO) . |
| WO 97/03985 | 2/1997 | (WO) . |

OTHER PUBLICATIONS

Waddell, W.R. et al., Am. J. Surgery, vol. 157, pp. 175–179 (1989).
Gonzaga, R.A.F. et al., The Lancet, Mar. 30, 1985, p. 751.
Waddell, W.R. et al., J. Surg. Oncology, vol. 24, pp. 83–87 (1983).
Federation Proceedings (1972) of the Federation of American Societies for Experimental Biology abstract Nos. 2044 and 2045.
Gilman, S.C. et al., Nonsteroidal Anti–inflammatory Drugs in Cancer Therapy, (circa 1985).
Brogden, R.N. et al., Drugs, vol. 16, pp. 97–114 (1978).
Hucker, H.B. et al., Drug Metabolism & Disposition, vol. 1, No. 6, pp. 721–736 (1973).
Shen, T.Y. et al., Chemical and Biological Studies on Indomethacin, Sulindac and Their Analogs, pp. 107–178 (circa 1975).
Duggan, D.E. et al., Clin. Pharm. & Therapeutics, vol. 21, No. 3, pp. 326–335 (1976).

(List continued on next page.)

*Primary Examiner*—Jerome D. Goldberg
(74) *Attorney, Agent, or Firm*—Robert W. Stevenson

(57) ABSTRACT

Derivatives of Quinazoline are useful for the treatment of patients having precancerous lesions. These compounds are also useful to inhibit growth of neoplastic cells.

19 Claims, No Drawings

OTHER PUBLICATIONS

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Lugnier, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 and RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor nucrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimidio–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnette, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5'cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoyl)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF-a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Andersson, Tomas L. G. et al., Interactions between isoprenaline, sodium nitroprusside, and isozyme–selective phosphodiesterase inhibitors on ADP–induced aggregation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, the Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC $^{-/-}$Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

METHOD OF TREATING A PATIENT HAVING PRECANCEROUS LESIONS WITH QUINAZOLINE DERIVATIVES

This application is a continuation of application Ser. No. 08/477,227, filed Jun. 7, 1995, now abandoned.

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps— literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptotis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

SUMMARY OF THE INVENTION

This invention is a method of treating patients with precancerous lesions or neoplasms by administering a pharmacologically effective amount of a compound of Formula I below to a patient in need of such treatment. Such compositions are effective in modulating apoptosis, and eliminating and inhibiting precancerous lesions, and neoplastic cells.

DETAILED DESCRIPTION OF THE PRESENTLY PREFERRED EMBODIMENTS

As discussed above, this invention is a method of treating a patient with precancerous lesions or neoplasms by administering a pharmacologically effective amount of the quinazoline derivative represented by the following formula (I), or the pharmacologically acceptable salt thereof;

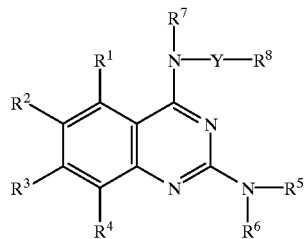

wherein $R^1$, $R^2$, $R^3$ and $R^4$, each of which may be the same or different from one another, represent each a hydrogen atom, a halogen atom, a alkyl group having 1 to 6 carbon atoms, a alkoxy group having 1 to 6 carbon atoms, a hydroxyalkyl group having 1 to 6 carbon atoms, a cyano group, an acylamino group, or a carboxyl group which may be protected, or two of $R^1$, $R^2$, $R^3$ and $R^4$ may together form methylenedioxy, ethylenedioxy, or a phenyl ring;

R5 and R6, each of which may be the same or different, are selected from a hydrogen atom, a lower alkyl group having 1 to 6 carbon atoms, a hydroxylalkyl group having from 1 to 6 carbon atoms, an aminoalkyl group having from 1 to 6 carbon atoms, a carboxyalkyl group which may be protected, alkylcarbamoyl group having 2 to 8 carbon atoms, a 1,3-benzdioxolyalkyl group or a 1,4-benzdioxylalkyl group, or further R5 and R6 may form a ring which may contain another nitrogen atom and or oxygen atom together with the nitrogen atom to which they are bonded, and which may be substituted;

R7 is selected from a hydrogen atom, a alkyl group having 1 to 6 carbon atoms, an acyl group, a alkoxyalkyl group having 2 to 8 carbon atoms, a carboxyalkyl group having 2 to 8 carbon atoms which may be protected or a hydroxyalkyl group having 2 to 8 carbon atoms;

R8 is selected from a hydrogen atom, a hydroxyl group, a carboxyl group which may be protected, a cyano group, an acyl group, a heteroaryl group which may be substituted or a benzyl group which may be substituted, said substitutions, which may be the same or different, are selected from a hydrogen atom, a halogen atom, a hydroxyl group, an amino group, a nitro group, a alkyl group having from 1 to 6 carbon atoms, a alkoxy group having from 1 to 6 carbon atoms, a alkoxyalkyl group having from 2 to 8 carbon atoms, a alkenyl group having from 2 to 8 carbon atoms, an acyl group an acylamino group, an alkylsulfonylamino group, a hydroiminoalkyl group, an alkyloxy-carbonylamino group, an alkyloxycarbonyloxy group or a heteroaryl group which may be substituted: or two of said substitutions may together form a saturated or unsaturated ring which may contain a nitrogen, a sulfer atom or an oxygen atom; and Y is a group represented by the formula—(CH2)q—(wherein q is 0 or an integer of 1 to 8), when q is an integer of 1 to 8, each carbon atom may have from 1 to 2 substituents, or Y is a group represented by the formula:

Preferably, R1, R2, R3, and R4, each of which may be the same or different from one another, are selected from a hydrogen atom, a cyano group, a halogen atom, or a lower alkoxy group. More preferably, one of R1, R2, R3 and R4 is a cyano group, a halogen atom or a methoxy group. Still more preferably, R2 is a halogen atom. Most preferably, R2 is a chlorine atom, and R1, R3 and R4 are hydrogen atoms.

It is preferred that Y is a group represented by the formula—$(CH_2)_q$—, wherein q is an integer of 1 to 8. When such occurs, R8 is benzyl group which may be substituted, said substitutions, each of which may be the same or different, are each selected from a hydrogen atom, a halogen atom, a hydroxy group, an amino group, a nitro group, a lower alkyl group, a lower alkoxy group, a lower alkoxyalkyl group, a lower alkenyl group, an acyl group, an acylamino group, an alkylsulfonylamino group, a hydroxyiminoalkyl group, an alkyloxycarbonylamino group, an alkyloxycarbonyloxy group or a heteroaryl group which may be substituted, or two of the substitutions may together form a saturated or unsaturated ring which may contain a nitrogen atom, a sulfer atom or an oxygen atom; and q is an integer of 1 to 8. However, it is preferred that R8 is a group represented by the formula:

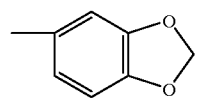

In which case, preferably, R7 is a hydrogen atom, and R5 and R6 form a ring represented by the formula:

wherein R9 is selected from a hydroxyl group which may be protected, a halogen atom, a alkyl group having 1 to 8 carbon atoms, a lower alkoxy group, a carboxyl group which may be protected, a hydroxyalkyl group, a carboxyalkyl group and a heteroacyl group.

Also, R5 and R6 may form a substituted ring structure represented by the formula:

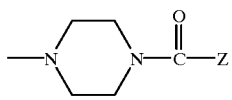

wherein Z is represented by the formula:

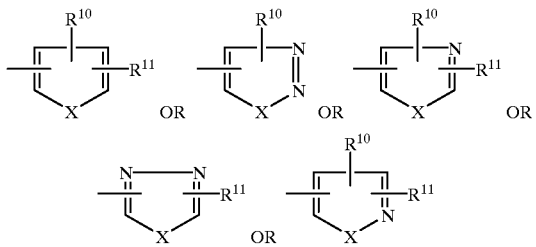

wherein X is S or O;

or Z is a cycloalkyl having 3 to 8 ring carbon atoms or a cycloalkenyl having 4 to 8 ring carbon atoms;

wherein R10 and R11 are independently selected from hydrogen, amino, lower alkyl, lower alkoxy and lower alkylthio; and X is either sulfur or oxygen.

Also, R5 and R6 may form a substituted ring structure represented by the formula:

wherein A represents a group selected from the following (i) and (ii):

(i) R12-CO—:
wherein R12 represents a lower alkyl group; phenyl substituted with a halogen atom, methoxy group or methanesulfonyl group; a styryl group unsubstituted or ring substituted with a halogen atom, methoxy group or 3,4-methylenedioxy group or 2-furyl group; and (ii) R13-:
wherein R13 represents a lower alkyl group of C1–C4; benzyl group substituted with a halogen atom or methoxy group; or B-(2-pyridyl)ethyl group.

"Alkyl group" refers to straight or branched chain $C_1$–$C_{12}$ groups such as methyl, ethyl, propyl, isopropyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine.

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, some of the compounds may form metal salts such as Na, K, Ca or Mg, and the pharmacologically acceptable salt of formula (I) also includes these metal salts.

Although the compound of formula I may be present as various isomers including geometrical isomers, i.e., cis-isomer and trans-isomer. and optical isomers, i.e., d-isomer and l-isomer depending upon the kinds and combination of the substituents, it is needless to say that the compounds include all of the isomers.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

Compounds of formula I may be formulated into compositions together with pharmaceutically acceptable carriers for injection, oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I, excipients such as cocoa butter or a suppository wax.

The pharmaceutically acceptable carrier and compounds of Formula I are formulated into unit dosage forms for administration to a patient. The dosage levels of active ingredient (i.e. compounds of Formula I) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In another form, the invention is a method of inhibiting the growth of neoplastic cells by exposing them to an effective amount of the compound of formula [I] above.

In still another form, the invention is a method of inducing apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of the compound of formula [I] above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formula above.

Preferable specific examples of the compound will now be described in order to facilitate the understanding of the present invention, though it is needless to say that the compounds of the present invention are not limited to these examples.

Preparation Process

Representative processes for the preparation of the compounds utilized in the present invention will now be described below. A representative quinazoline skeleton as shown following is useful to represent the processes.

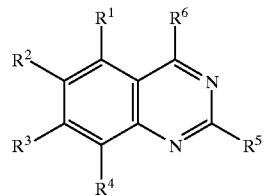

Though compounds having a quinazoline skeleton are mainly described in the following explanation, the following explanation can be applied for compounds having a skeleton other than the quinazoline skeleton.

Preparation Process 1

When $R^5$ is a hydrogen atom, a halogen atom or a group selected from among those which are directly bonded to the quinazoline skeleton through a carbon atom in the general formula (I), a compound similar to the general formula (I) can also be prepared by the following process:

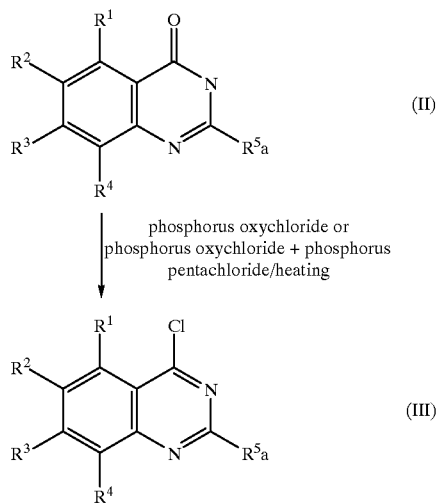

(in a series of formulas, $R^5_a$ is a hydrogen atom, a halogen atom or a group selected from among those which are directly bonded to the quinazoline skeleton through a carbon atom in $R^5$ described above; and $R^1$, $R^2$, $R^3$ and $R^4$ are each as defined above.

That is, this process is one for preparing a quinazoline derivative represented by the general formula (III) by reacting a quinazoline derivative represented by the general formula (II) with phosphorus oxychloride or by reacting it with phosphorus oxychloride in the presence of phosphorus pentachloride under heating.

Preparation Process 2

When $R^5$ is a group selected from among a hydrogen atom, a halogen atom, a group represented by the formula:

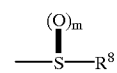

(wherein $R^8$ and m are each as defined above), a group represented by the formula —O—$R^9$ (wherein $R^9$ represents a hydroxyalkyl group which may be protected, a carboxyalkyl group which may be protected or a benzyl group), a heteroaryl group which may be substituted and a group which is directly bonded to the ring through a carbon atom (for example, a lower alkyl group, a carboxyl group which may be protected, a 1,3-benzodioxolyl group which may be substituted, a 1,4-benzodioxyl group which may be substituted, a 1,3-benzodioxolylalkyl group which may be substituted and a 1,4-benzodioxylalkyl group which may be substituted); and $R^6$ is a group selected from among those defined above with respect to $NR^7YR^8$ except a hydrogen atom, halogen atoms and lower alkyl groups in the general formula (I), a compound similar the general formula (I) can be prepared by the following process:

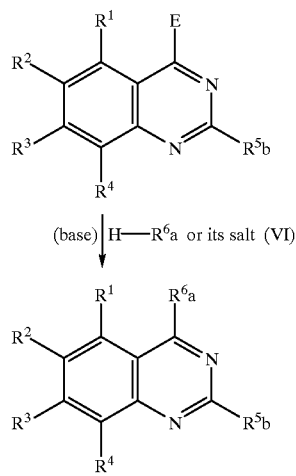

(IV)

(base) ↓ H—R⁶a or its salt (VI)

(V)

[in a series of formulas $R^1$, $R^2$, $R^3$ and $R^4$, are each as defined above; $R_b$ represents a group selected from among a hydrogen atom, a halogen atom, a group represented by the formula

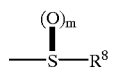

(wherein $R^8$ and m are each as defined above), a group represented by the formula —O—$R^9$ (wherein $R^9$ is as defined above), a heteroaryl group which may be substituted and a group which is directly bonded to the ring through a carbon atom (for example, a lower alkyl group, a carboxyl group which may be protected, a 1,3-benzodioxolyl group which may be substituted, a 1,4-benzodioxyl group which may be substituted, a 1,3-benzodioxylalkyl group which may be substituted and 1,4-benzodioxylalkyl group which may be substituted); $R^6_a$ represents a group selected from among those defined above with respect to $R^6$ except a hydrogen atom, halogen atoms and lower alkyl groups; and E represents an eliminable group].

That is, this process is one for preparing an objective compound (V) by condensing a quinazoline derivative represented by the general formula (IV) with a compound represented by the general formula (VI).

The eliminable group represented by E in the formula includes halogen atoms and alkoxy groups.

This process may be conducted in the presence of a base at need.

The base includes organic bases such as triethylamine, pyridine and diisopropylethylamine; inorganic bases such as sodium carbonate, potassium carbonate, sodium hydrogencarbonate, sodium hydroxide and sodium hydride; and alkoxides such as sodium methoxide and potassium t-butoxide.

As the reaction solvent, every solvent which is inert to the reaction can be used and examples thereof include ethanol, isopropyl alcohol, tetrahydrofuran, dimethylformamide and dimethyl sulfoxide. This process can be conducted even in the absence of any solvent in some cases.

The reaction temperature preferably ranges from −20 to 300° C.

Preparation Process 3

When $R^5$ is a group selected from among those defined above with respect to $NR^5R^6$ except a hydrogen atom, halogen atoms and groups which are directly bonded to the quinazoline skeleton through a carbon atom; and $R^6$ is a group selected from among those defined above with respect to $R^6$ except halogen atoms in the general formula (I), a compound similar to the general formula (I) can be prepared by the following process:

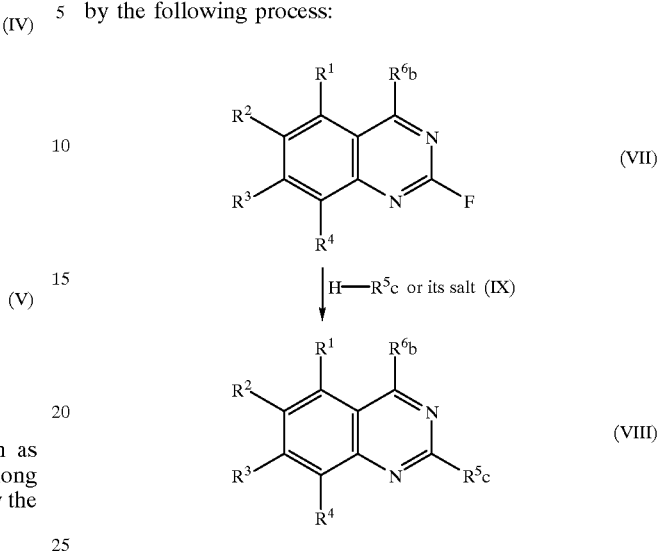

(in a series of formulas, $R^1$, $R^2$, $R^3$ and $R^4$ are each as defined above; $R^5_c$ is a group selected from among those defined above with respect to $R^5$ except a hydrogen atom, halogen atoms and groups which are directly bonded to the quinazoline skeleton through a carbon atom;

$R^6_b$ is a group selected from among those defined above with respect to $R^6$, except halogen atoms; and F represents an eliminable group).

That is, this process is one for preparing an objective compound (VIII) by condensing a compound represented by the general formula (VII) with a compound represented by the general formula (IX).

The eliminable group represented by F in the formula includes, for example, halogen atoms, alkylthio groups and so forth.

This process may be conducted in the presence of a base at need.

The base includes organic bases such as triethylamine, pyridine and diisopropylethylamine; inorganic bases such as sodium carbonate, potassium carbonate, sodium hydrogencarbonate, sodium hydroxide and sodium hydride; and alkoxides such as sodium methoxide and potassium t-butoxide.

As the reaction solvent, every solvent which is inert to the reaction can be used and examples thereof include ethanol, isopropanol, tetrahydrofuran, dimethylformamide and dimethyl sulfoxide.

The reaction temperature preferably ranges from 0 to 300° C.

Preparation Process 4

When $R^5$ is a group represented by the formula

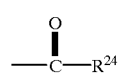

(wherein $R^{24}$ is a hydrogen atom or a lower alkyl group in the general formula (I), a compound similar to the general formula (I) can also be prepared by the following process:

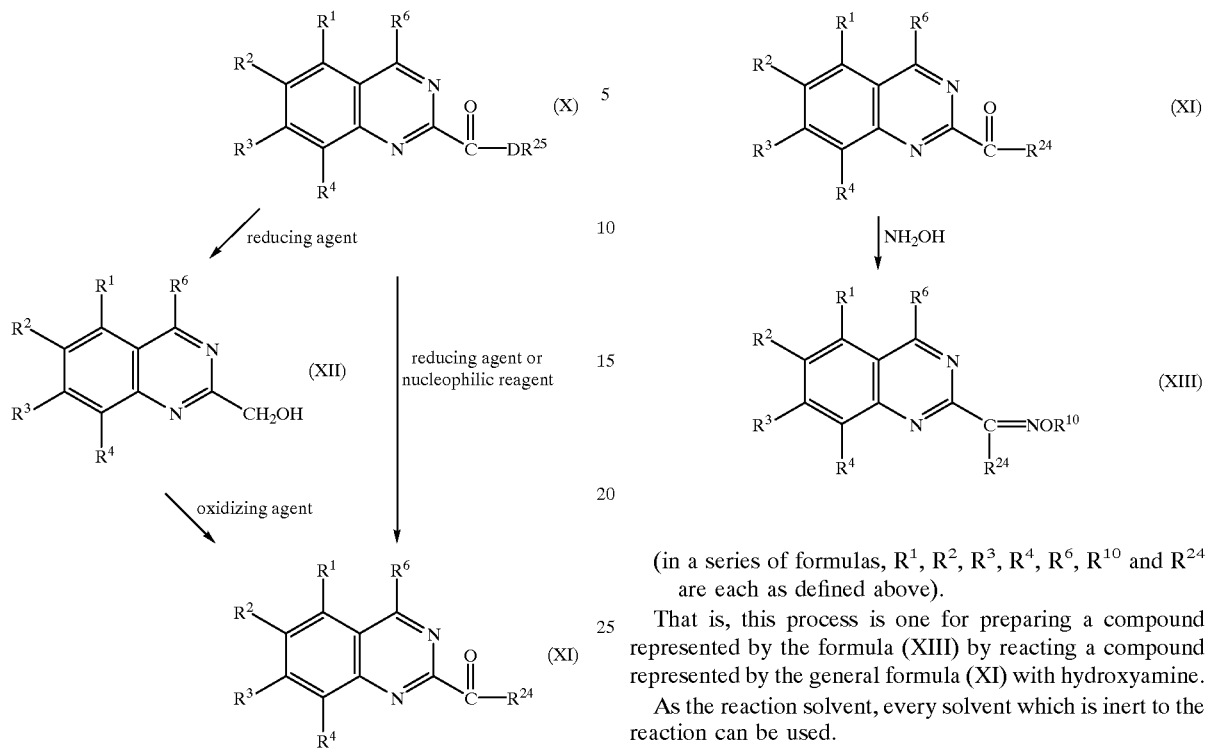

(in a series of formulas, $R^1$, $R^2$, $R^3$ and $R^4$ and $R^6$ are each as defined above; and $R^{24}$ and $R^{25}$, each of which may be the same or different from each other, represent each a hydrogen atom or a lower alkyl group).

That is, this process is one for preparing an objective compound (XI) by reacting a compound represented by the general formula (X) with an ordinary reducing agent or an ordinary nucleophilic reagent, either directly or through the oxidation of an alcohol (XII).

The reducing agent includes lithium aluminum hydride, sodium borohydride, diisobutylaluminum hydride and so forth.

The nucleophilic reagent includes lower alkyl metals such as methyllithium, methylmagnesium bromide and so forth.

The oxidizing agent to be used when the reaction is conducted through the alcohol (XII) includes potassium bichromate/sulfuric acid, dimethyl sulfoxide/oxalyl chloride and so forth.

As the reaction solvent, every solvent which is inert to the reaction can be used.

The reaction temperature ranges from 0° C. to the refluxing temperature of the solvent.

Preparation Process 5

When $R^5$ is a group represented by the formula

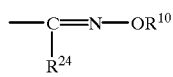

(wherein $R^{10}$ and $R^{24}$ are each as defined above) in the general formula (I), a compound represented by the general formula (I) can also be prepared by the following process (in a series of formulas, $R^1$, $R^2$, $R^3$, $R^4$, $R^6$, $R^{10}$ and $R^{24}$ are each as defined above).

That is, this process is one for preparing a compound represented by the formula (XIII) by reacting a compound represented by the general formula (XI) with hydroxyamine.

As the reaction solvent, every solvent which is inert to the reaction can be used.

The reaction temperature ranges from 0° C. to the refluxing temperature of the solvent.

Preparation Process 6

When $R^5$ is a group represented by the formula

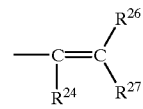

(wherein $R^{24}$ is as defined above; $R^{26}$ represents a hydrogen atom or a lower alkyl group; and $R^{27}$ represents a hydrogen atom, a lower alkyl group, a carboxyl group which may be protected or a carboxyalkyl group which may be protected) in the general formula (I), a compound represented by the formula (I) can also be prepared by the following process:

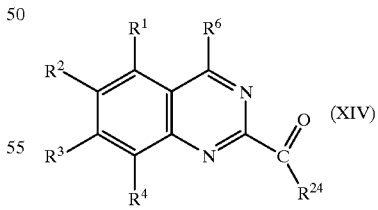

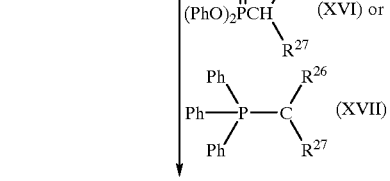

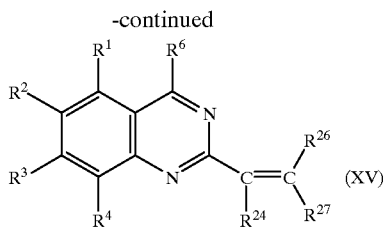

(in a series of formulas, $R^1$, $R^2$, $R^3$, $R^4$, $R^6$, $R^{24}$, $R^{26}$ and $R^{27}$ are each as defined above; and Ph represents a phenyl group).

That is, this process is one for preparing a compound represented by the general formula (XV) by reacting a compound represented by the general formula (XIV) with a compound represented by the general formula (XVI) or the general formula (XVII) through the Wittig reaction.

As the reaction solvent, every solvent which is inert to the reaction can be used.

The reaction temperature ranges from 0° C. to the refluxing temperature of the solvent.

Preparation Process 7

When $R^5$ is a group represented by the formula

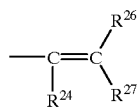

(wherein $R^{24}$, $R^{26}$, and $R^{27}$ are each as defined above) in the general formula (I), a compound represented by the formula (I) can also be prepared by the following process:

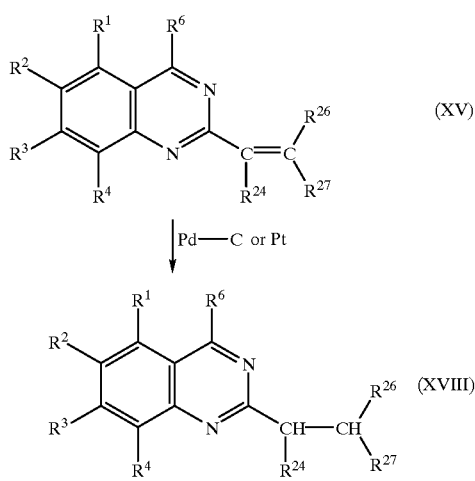

(in a series of formulas, $R^1$, $R^2$, $R^3$, $R^4$, $R^6$, $R^{24}$, $R^{26}$ and $R^{27}$ are each as defined above).

That is, this process is one for preparing an objective compound (XVIII) by reducing the compound represented by the general formula (XV) prepared in the Preparation process 6.

The reduction can be conducted by conventional means, for example, catalytic reduction using palladium/carbon or platinum catalyst.

As the reaction solvent, every solvent which is inert to the reaction is used.

Preparation Process 8

When $R^6$ is a group represented by the formula

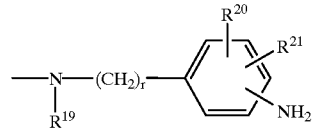

(wherein $R^{19}$, $R^{20}$, $R^{21}$ and r are each as defined above) in the general formula (I), a compound represented by the general formula (I) can also be prepared by the following process:

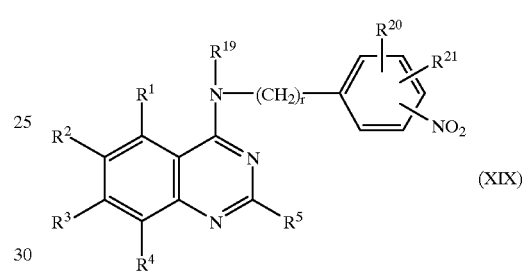

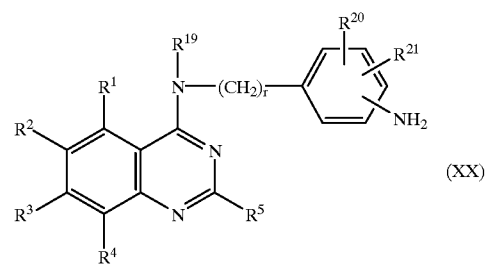

(in a series of formulas, $R^1$, $R^2$, $R^3$, $R^4$, $R^5$, $R^{19}$, $R^{20}$, $R^{21}$ and r are each as defined above).

That is, this process is one for preparing an objective compound (XX) by reducing a compound represented by the general formula (XIX).

The reduction is conducted by conventional means, e.g., catalytic reduction using palladium/carbon or platinum catalyst or reduction with iron or tin.

As the reaction solvent, every solvent which is inert to the reaction can be used.

Preparation Process 9

When $R^5$ is a group represented by the formula —O—$R^9$ (wherein $R^9$ is a carboxyl group which may be protected) in the general formula (I), a compound represented by the formula (I) can be prepared by the following process:

(The First Step)

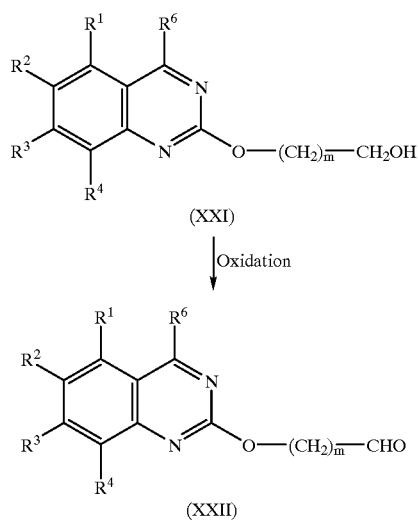

(in a series of formulas, $R^1$, $R^2$, $R^3$, $R^4$ and $R^6$ are each as defined above; and m represented 0 or an integer of 1 to 2).

That is, this process is one for preparing a compound represented by the general formula (XXII) by oxidizing a compound represented by the general formula (XXI) by conventional means.

As the oxidizing agent, everyone can be used so far as it is conventionally used and examples thereof include chromium (VI), dimethyl sulfoxide and oxalyl chloride.

As the reaction solvent, every solvent which is inert to the reaction can be used.

The reaction temperature ranges from 0° C. to the refluxing temperature of the solvent.

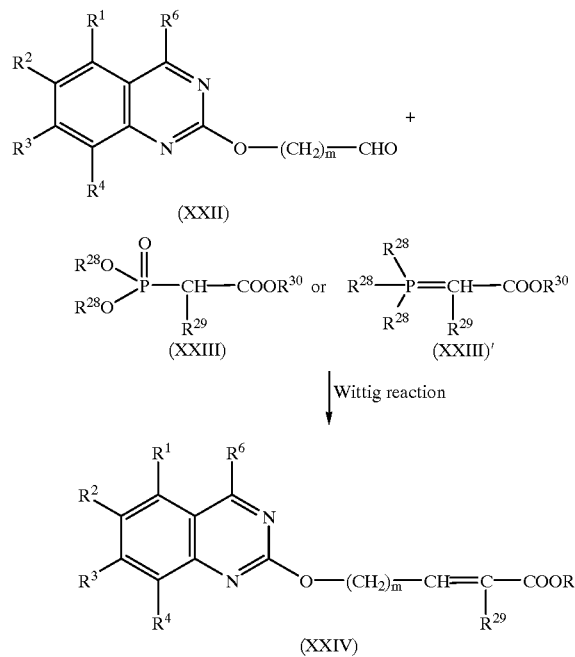

(in a series of formulas, $R^1$, $R^2$, $R^3$, $R^4$, $R^6$ and m are each as defined above; and $R^{28}$, $R^{29}$ and $R^{30}$ each of which may be the same or different from one another, represent each a hydrogen atom or a lower alkyl group).

That is, this process is one for preparing a compound represented by the general formula (XXIV) by reacting the compound (XXII) prepared in the first step with the Wittig reagents (XXIII) or (XXIII)'.

As the reaction solvent, everyone which is inert to the reaction can be used.

The reaction temperature ranges from 0° C. to the refluxing temperature of the solvent.

(The Third Step)

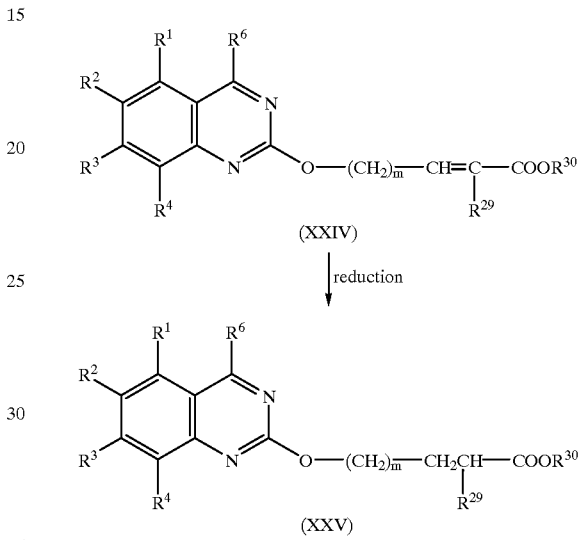

(in a series of formulas, $R^1$, $R^2$, $R^3$, $R^4$, $R^6$, $R^{29}$, $R^{30}$ and m are each as defined above).

That is, this process is one for preparing the objective compound (XXV) by reducing the compound (XXIV) prepared in the second step.

The reduction may be conducted by conventional means, and examples thereof include catalytic reduction using palladium/carbon or platinum catalyst.

Preparation Process 10

When $R^6$ is a group represented by the formula

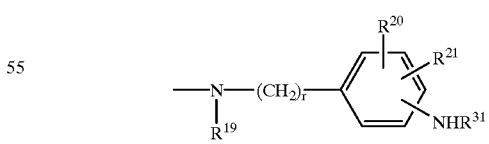

(wherein $R^{19}$, $R^{20}$, $R^{21}$ and r are each as defined above; and $R^{31}$ represents an acyl group, a lower alkylsulfonyl group or a lower alkyloxycarbonyl group) in the general formula (I), a compound represented by the general formula (I) can also be prepared by the following process:

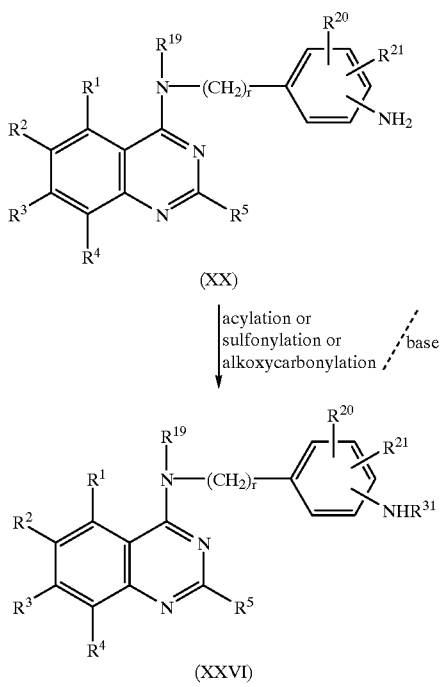

(XX)

acylation or
sulfonylation or
alkoxycarbonylation / base (XXVI)

(in a series of formulas, $R^1$, $R^2$, $R^3$, $R^4$, $R^5$ $R^{19}$, $R^{20}$, $R^{21}$ and $R^{31}$, and r are each as defined above).

That is, this process is one for preparing an objective compound (XXVI) by subjecting the compound represented by the general formula (XX) prepared in the Preparative process 8 to the conventional acylation, sulfonylation or alkoxycarbonylation in the presence of a base.

As the acylating agent, every acylating agent which is conventionally used, for example, activated derivatives of carboxylic acids such as acid chloride, acid anhydride and mixed acid anhydride; and condensing agents such as dicyclohexylcarbodiimide is used.

As the sulfonylating agent, every sulfonylating agent which is conventionally used can be used and examples thereof include a lower alkylsulfonyl chloride and a lower alkylsulfonic anhydride.

The alkoxycarbonylating agent includes every alkoxycarbonylating agent which is conventionally used, for example, a lower alkyloxycarbonyl chloride and a lower alkyl pyrocarbonate.

At the base, every base can be used and examples thereof include organic bases such as pyridine and triethylamine; and inorganic bases such as sodium carbonate, potassium carbonate, sodium hydroxide and sodium hydride.

Preparation Process 11

When a compound similar to formula (I) is desired, except having 2 rings A and B, the ring A is selected from any of a benzene ring, a pyridine ring and a cyclohexane ring, the ring B is selected from among a pyridine ring, a pyrimidine ring and an imidazole ring, $R^5$ represents a group selected from among those defined above with respect to $R^5$ except groups which are directly bonded to the ring portion through a carbon atom; and $R^6$ represents a group selected from among those defined above with respect to $R^5$ except groups which are directly bonded to the ring portion through a carbon atom in the general formula (I), the compound represented by the general formula (I) can also be prepared by the following process. The case in which the ring portion forms a quinazoline skeleton is shown below as the representative of the above (The First Step)

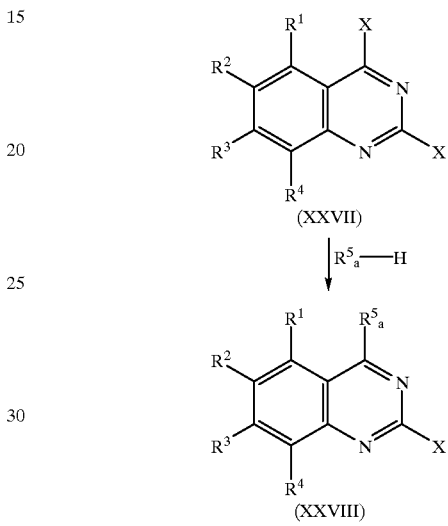

(XXVII)

$R^5_a$—H (XXVIII)

(in a series of formulas, $R^1$, $R^2$, $R^3$ and $R^4$ are each as defined above; $R^5_a$ represents a group selected from among those defined above with respect to $R^5$ except groups which are directly bonded to the ring portion through a carbon atom; and X represent s a halogen atom).

That is, the first step is a condensation reaction according to a conventional process.

Alcohol solvents such as isopropyl alcohol, ether solvents such as tetrahydrofuran and dimethylformamide are preferably used as the reaction solvent. However, every solvent which is inert to the reaction can be used.

In the case where $R^5_a$ is bonded to the ring portion through a nitrogen atom, it is preferred that the reaction is proceeded by heating under reflux in the presence of a tertiary amine such as triethylamine while removing HCl generated. While in the case where $R^5_a$ is bonded to the ring portion through an oxygen atom or a sulfur atom, it is preferred that the reaction is proceeded by heating under reflux in the presence of an a alkali such as sodium hydroxide and sodium carbonate.

(The Second Step)

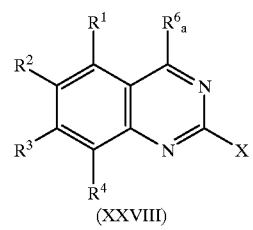

(XXVIII)

↓ $R^6{}_a$—H

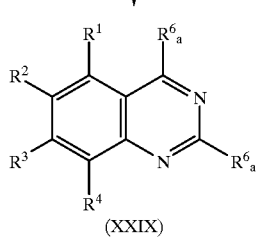

(XXIX)

(in a series of formulas, $R^1$, $R^2$, $R^3$, $R^4$, $R^5{}_a$ and X are each as defined above: $R^6{}_a$ represents a group selected from among those defined above with respect to $R^6$ except groups which are directly bonded to the ring portion through a carbon atom).

The second step is a reaction wherein the compound (XXVIII) obtained in the first step is condensed with a compound represented by the formula $R^6{}_a$—H according to a conventional process.

Alcohol solvents such as isopropyl alcohol, ether solvents such as tetrahydrofuran and dimethylformamide are preferably used as the reaction solvent. However, every solvent which is inert to the reaction can be used.

In the case where $R^6{}_a$ is bonded to the ring portion through a nitrogen atom, it is preferred that the reaction is proceeded by heating under reflux in the presence of an organic base such as triethylamine, pyridine and ethyldiisopropylamine, an inorganic base such as sodium carbonate, potassium carbonate, sodium hydrogencarbonate, sodium hydride and sodium hydroxide or an alkoxide such as sodium methoxide and potassium t-butoxide. While in the case where $R^6{}_a$ is bonded to the ring portion through an oxygen atom or a sulfur atom, it is preferred that the reaction is proceeded by heating under reflux in the presence of an alkali such as sodium hydroxide and sodium carbonate.

Preparation Process 12

When the compound represented by the general formula (1) is a compound represented by the following general formula (XXXII):

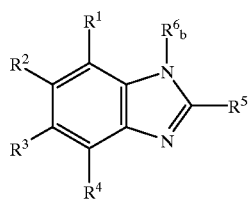

(XXXII)

the compound can also be prepared by the following process.

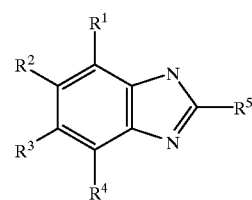

(XXX)

$R^6{}_b$—Cl
(XXXI)/NaI

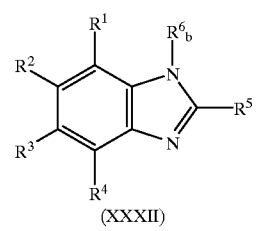

(XXXII)

(in a series of formulas $R^1$, $R^2$, $R^3$, $R^4$, and $R^5$ are each as defined above; and $R^6{}_b$ represents a group selected from among groups which are directly bonded to the ring portion through a carbon atom in those defined above with respect to $R^6$).

That is, this process is one for preparing an objective compound by reacting, for example, piperonyl chloride (XXXI) with a benzimidazole derivative represented by the general formula (XXX) in the presence of an alkali by a conventional process.

Sodium iodide is preferred as alkali.

Although every solvent which is inert to the reaction can be used as the reaction solvent, polar solvents such as dimethylforamide can be cited as preferable ones.

The reaction temperature is preferably about 60 to 100° C., particularly preferably about 70 to 80° C.

Preparation Process 13

Additional compounds can also be prepared by the following process:

(The First Step)

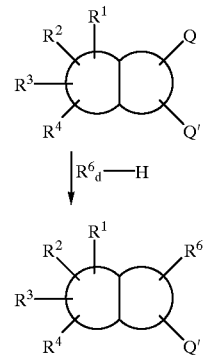

↓ $R^6{}_d$—H

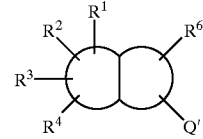

(in a series of formulas, $R^1$, $R^2$, $R^3$ and $R^4$ are each as defined above; $R^6{}_d$ represents a group selected from among those defined above with respect to $R^6$ except groups which are directly bonded to the ring portion through a carbon atom; and Q and Q' represent halogen atoms).

The first step is a condensation reaction according to a conventional process In the case where $R^6{}_d$ is bonded to the ring portion through a nitrogen atom, it is preferred that the reaction is proceeded by heating under ref lux in the presence of an organic base such as triethylamine, pyridine and diisopropylethylamine, an inorganic base such as sodium carbonate, potassium carbonate, sodium hydrogencarbonate, sodium hydroxide and sodium hydride or an alkoxide such as sodium methoxide and potassium t-butoxide. While in the case where $R^6_d$ is bonded to the ring portion through an oxygen atom or a sulfur atom, it is preferred that the reaction is proceeded by heating under reflux in the presence of an inorganic base such as sodium hydroxide and sodium carbonate.

Every solvent which is inert to the reaction can be used as the reaction solvent, and examples thereof include alcohol solvents such as ethanol and isopropyl alcohol, ether solvents such as tetrahydrofuran, dimethylformamide and dimethylsulfoxide. Further, in the present process, the reaction can be proceeded in the absence of a reaction solvent in some cases.

(The Second Step)

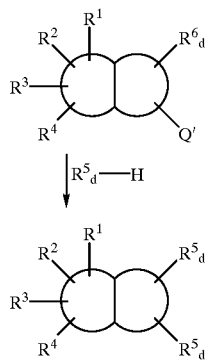

(in a series of formulas, $R^1$, $R^2$, $R^3$, $R^4$, $R^6_d$ and Q are each as defined above; and $R^5_d$ represents a group selected from among those defined above with respect to $R^5$ except groups which are directly bonded to the ring portion through a carbon atom).

That is, the second step is a process for preparing an objective compound in which the compound obtained in the first step is condensed with a compound represented by the general formula $R^5_d$—H.

In the present process, the reaction can be processed in the presence of a base at need.

As the base, organic bases such as triethylamine, pyridine and diisopropylethylamine, inorganic bases such as sodium carbonate, potassium carbonate, sodium hydrogencarbonate, sodium hydroxide and sodium hydride and alkoxides such as sodium methoxide and potassium t-butoxide can be cited.

Every solvent which inert to the reaction can be used as the reaction solvent, and examples thereof include alcohol solvents such as ethanol and isopropanol, ether solvents such as tetrahydrofuran, dimethylformamide and dimethylsulfoxide.

The reaction temperature is preferably 0° C. to 300° C.

In the case where $R^5_d$ is a group which is bonded to the ring portion through a nitrogen atom, it is preferred that the reaction is proceeded by heating under reflux in the presence of a tertiary amine such as triethylamine. While in the case where $R^5_d$ is a group which is bonded to the ring portion through a oxygen atom or a sulfur atom, it is preferred that the reaction is proceeded by heating under reflux in the presence of an alkali such as sodium hydroxide and sodium carbonate.

The compounds thus obtained in the preparation processes 1 to 13 described above can form salts thereof by a conventional process, for example, by adding sodium hydroxide, potassium hydroxide or methanesulfonic chloride.

Next, the preparation processes for the raw compounds used in the preparation processes will be shown.

Preparation Process A

Among the starting materials used in the preparation process 13, the compound in which the ring portion is a quinazoline ring and Q and Q' are chlorine atoms can also be prepared by the following process:

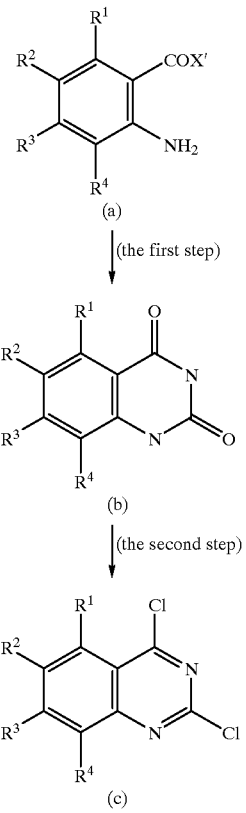

(in a series of formulas, $R^1$, $R^2$, $R^3$ and $R^4$ are each as defined above; and X' represents any group among a hydroxyl group, an alkoxy group and an amino group).

That is, this process is one for preparing the objective compound (c) by cyclizing the compound (a) by a conventional process to obtain the compound (b) and then chlorinating it by a conventional process.

The first step is a cyclization reaction. It is a step in which urea is reacted with the compound (a) to obtain the compound (b). In this case, the reaction temperature is preferably about 170 to 190° C., and although every solvent can be used as long as it is inert to the reaction, preferable examples thereof include N-methylpyrrolidone and the like. In this step, the reaction can also be proceeded in the absence of the solvent.

Further, the compound (b) can also be obtained by cyclizing with carbonyldiimidazole or by cyclizing under an acidic or basic condition after converting to urethane with a chloroformic ester when X' is an amino group.

The second step is a chlorination reaction. This step can be carried out by a conventional manner, and examples thereof include a process in which the compound (b) is heated under reflux with phosphorus pentachloride and phosphorus oxychloride, or phosphorus oxychloride while stirring to chlorinate.

Preparation Process B

The starting material (II) used in the preparation process 1 can be prepared by the following process:

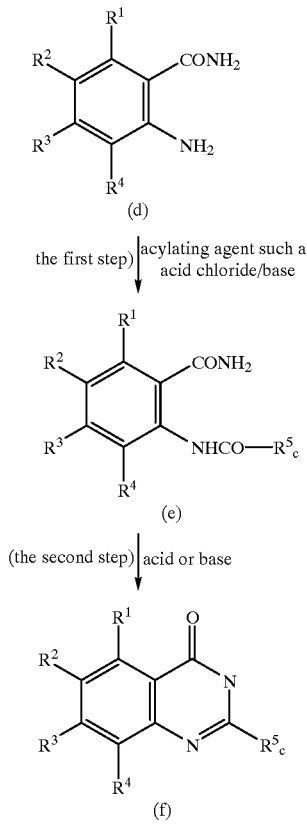

(in a series of formulas, $R^1$, $R^2$, $R^3$ and $R^4$ are each as defined above; and $R^5_c$ represents a halogen atom or a group selected from among groups which are directly bonded to the ring portion through a carbon atom in those defined with respect to above $R^5$).

That is, the above process is a reaction in which an amide product is obtained by a conventional process in the first step and a cyclization is carried out in the presence of an acid or a base in the second step.

The amide produce (e) can be obtained by a conventional process, and it can be obtained, for example, by reacting the compound (d) with an acylating agent such as an acid chloride represented by $R^5_c$—COCl in the presence of a base.

Tertiary amines such as triethylamine and organic bases such as pyridine are preferably cited as the base.

Specific examples of the acylating agent include acid chlorides such as benzoyl chloride, acetyl chloride, ethyloxalyl chloride and benzyloxyacetyl chloride.

The reaction temperature is preferably about 0° C. to 30° C.

In the second step, the compound (e) obtained in the first step is heated under reflux in the presence of an acid or a base to obtain the compound (f).

The acid includes acetic anhydride and the like.
The base includes sodium hydroxide and the like.

Preparation Process C

The starting material (II) can also be prepared by the following process when $R^5_a$ is a hydrogen atom in the preparation process 1:

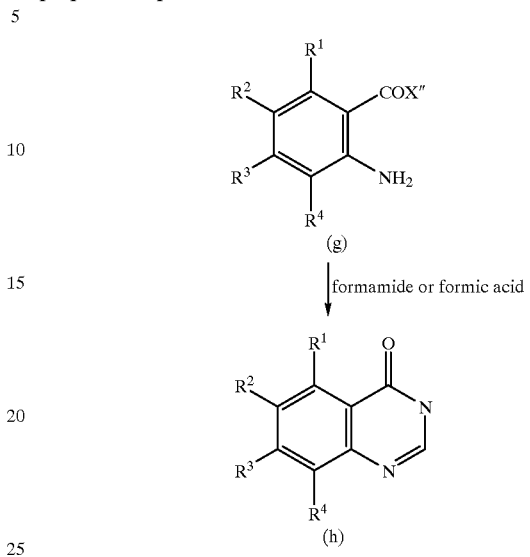

(in a series of formulas, $R^1$, $R^2$, $R^3$ and $R^4$ are each as defined above; and X" represents a hydroxyl group or a lower alkoxy group).

That is, the above process is a cyclization reaction by a conventional process.

The objective compound (h) can be synthesized, for example, by condensing the raw compound (g) with formamide by heating under reflux, or by heating it together with formic acid.

Examples of the present invention will now be described, though it is needless to say that the present invention is not limited to them. In advance of Examples, preparative examples of the raw compound for compounds according to the present invention will be described. In the Examples, Me represents a methyl group, Et an ethyl group, Bzl a benzyl group and Ac an acetyl group.

EXAMPLES

Preparative Example 1

2-Ethoxycarbonyl-6-chloroquinazolin-4(3H)-one

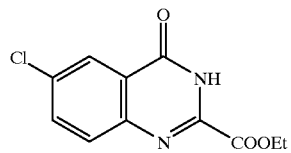

2.50 g (0.0147 mol) of 2-amino-5-chlorobenzamide was dissolved in 15 ml of pyridine. 2.0 ml of ethyloxalyl chloride was dropped into the obtained solution under stirring at room temperature. The obtained mixture was stirred for several hours and distilled under a reduced pressure to remove the solvent. The obtained residue was used as such in the subsequent reaction.

The residue was dissolved in 50 ml of acetic acid, followed by the addition of 5 ml of acetic anhydride. The obtained mixture was heated under reflux for 24 hours. The solvent was distilled away under a reduced pressure and ethanol was added to the obtained crystalline residue. The obtained mixture was filtered to recover the crystal. The crystal was washed with ethanol and ether and air-dried to give 2.78 g of the title compound as a pale-yellow crystal.

yield (%); 75 m.p.(° C.); 239~240

Mass; 253 (M+H)$^+$

NMR δ(DMSO-d$_6$);

1.36 (3H, t, J=7.2 Hz), 4.39 (2H, q, J=7.2 Hz), 7.86 (1H, d, J=8.8 Hz), 7.92 (1H, dd, J=8.8 Hz, 2.4 Hz), 8.11(1H,d, J=2.4 Hz), 12.85(1H,brs)

Example 1

2-Morpholino-4-(3,4-methylenedioxybenzyl)amino-6-cyanoquinazoline

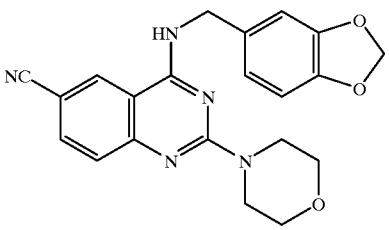

A mixture comprising 338 mg of 2-chloro-4-(3,4-methylenedioxybenzyl)amino-6-cyanoquinazoline, 435 mg of morpholine and 20 ml of isopropyl alcohol was heated under reflux for 3 hours, followed by the addition of 30 ml of water under heating. The precipitate thus formed was recovered by filtration and washed with 30 ml of water and 30 ml of ethyl acetate. Thus, 310 mg of the title compound was obtained.

molecular formula; $C_{21}H_{19}N_5O_3$ (389)

yield (%); 80 m.p.(° C.); 270~272 (dec.)

Mass; 390 (M+1)$^+$

NMR δ(DMSO-d$_6$);

3.57–3.61 (4H, m), 3.73~3.79 (4H, m), 4.57 (2H, d, J=5.6 Hz), 5.95 (2H, s), 6.82 (1H, d, J=8.0 Hz), 6.85 (1H, d, J=8.0 Hz), 6.93 (1H, s), 7.27 (1H, d, J=8.8 Hz), 7.74 (1H, dd, J=8.8 Hz, 1.6 Hz), 8.56 (1H, d, J=1.6 Hz), 8.75 (1H, brt, J=5.6 Hz)

Examples 2 to 3

The following compounds were prepared in a similar manner to that of Example 1.

Example 2

2-Morpholino-4-(3,4-methylenedioxybenzyl)amino-6-chloroquinazoline

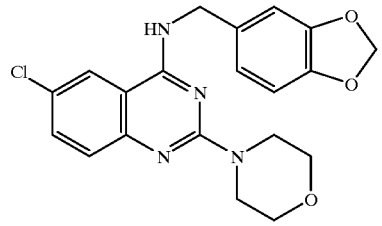

molecular formula; $C_{20}H_{19}N_4O_3Cl$ (398.850)

yield (%); 96 m.p.(° C.); 208~209

Mass; 399 (MH)$^+$

NMR δ(DMSO-d$_6$);

3.61 (4H, t, J=5 Hz), 3.72 (4H, t, J=5 Hz), 4.58 (2H, d, J=5.7 Hz), 5.97 (2H, s), 6.85 (2H, s), 6.95 (1H, s) 7.28 (1H, d, J=9.0 Hz), 7.51 (1H, dd, J=2.4 Hz, 9.0 Hz), 8.18 (1H, d, J=2.4 Hz), 8.60 (1H, t, J=5.7 Hz)

Example 3

2-Morpholino-4-(3-chloro-4-methoxybenzyl)amino-6-cyanoquinazoline

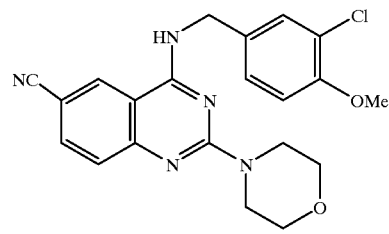

molecular formula; $C_{21}H_{20}N_5O_2Cl$ (407.5)

yield (%); 51 m.p.(° C.); 222~223

Mass; 410 (M+1)$^+$

NMR δ(DMSO-d$_6$);

3.56~3.61 (4H, m), 3.74~3.80 (4H, m), 3.80 (3H, s), 4.58 (2H, d, J=5.2 Hz), 7.27~7.32 (2H, m), 7.44 (1H, d, J=1.6 Hz), 7.75 (1H, dd, J=8.8 Hz, 1.6 Hz), 8.55 (1H, d, J=1.6 Hz), 8.80 (1H, brt, J=5.2 Hz)

Example 4

2-(4-Hydroxypiperidino)-4-(3,4-methylenedioxybenzyl)amino-6-cyanoquinazoline

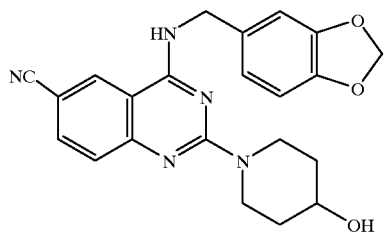

A mixture comprising 339 mg of 2-chloro-4-(3,4-methylenedioxybenzyl)amino-6-cyanoquinazoline, 500 mg of 4-hydroxypiperidine and 20 ml of N,N-dimethylformamide was heated under reflux for 5 hours and poured into 50 ml of water, followed by the addition of 50 ml of ethyl acetate. The obtained mixture was filtered to remove insolubles. The organic layer of the filtrate was dried over magnesium sulfate and concentrated under a reduced pressure to give a crystalline residue. This residue was washed with chloroform to give 145 mg of the title compound.

molecular formula; $C_{22}H_{21}N_5O_3$ (403)

yield (%); 36 m.p.(° C.); 229

Mass; 404 (M+1)$^+$

NMR δ(DMSO-d$_6$);

1.19~1.30 (2H, m), 1.64~1.77 (2H, m), 3.21~3.30 (2H, m), 3.63~3.75 (1H, m), 4.34~4.38 (2H, m), 4.55 (2H, d, J=5.6 Hz), 4.66 (1H, d, J=4.0 Hz), 5.94 (2H, s), 6.80 6.86 (2H, m), 6.93 (1H, d, J=0.8 Hz), 7.24 (1H, d, J=8.4 Hz), 7.70 (1H, dd, J=8.4 Hz, 1.6 Hz), 8.52 (1H, d, J=1.6 Hz), 8.70 (1H, br)

Examples 5 to 11

The following compounds were prepared in a similar manner to that of Example 4.

Example 5

2-(4-Hydroxypiperidino)-4-(3,4-methylenedioxybenzyl)amino-6-chloroquinazoline

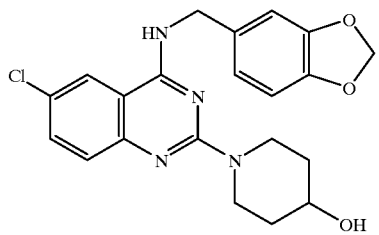

molecular formula; $C_{21}H_{21}N_4O_3Cl$ (412.877)

yield (%); 56 m.p.(° C.); 157~158

Mass; 413 (MH$^+$)

NMR δ(DMSO-d$_6$);

1.2~1.3 (2H, m), 1.6~1.8 (2H, m), 3.1~3.2 (2H, m), 3.6~3.7 (1H, m), 4.3~4.4 (2H, m), 4.55 (2H, d, J=5.7 Hz), 4.65 (1H, d, J=4.4 Hz), 5.96 (2H, s), 6.84 (2H, s), 6.95 (1H, s), 7.24 (1H, d, J=9.0 Hz), 7.47 (1H, dd, J=2.4 Hz, 9.0 Hz), 8.13 (1H, d, J=2.4 Hz), 8.53 (1H, t, J=5.7 Hz)

Example 6

2-(4-Hydroxypiperidino)-4-(3-chloro-4-methoxybenzyl)amino-6-cyanoquinazoline

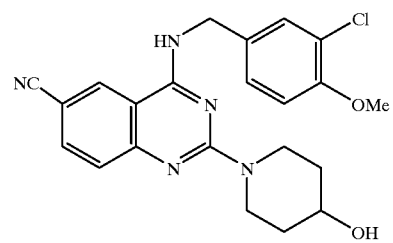

molecular formula; $C_{22}H_{22}N_5O_2Cl$ (423.5)

yield (%); 80 m.p.(° C.); 207~208

Mass; 424 (M+1)$^+$

NMR δ(DMSO-d$_6$);

1.18~1.30 (2H, m), 1.65~1.76 (2H, m), 3.21~3.33 (2H, m), 3.30 (3H, s), 3.64~3.72 (1H, m), 4.29~4.37 (2H, m), 4.57 (2H, d, J=5.6 Hz), 4.66 (1H, d, J=1.8 Hz), 7.07 (1H, d, J=8.4 Hz), 7.24 (1H, d, J=8.8 Hz), 7.29 (1H, dd, J=8.4 Hz, 2.0 Hz), 7.43 (1H, d, J=2.0 Hz), 7.71 (1H, dd, J=8.8 Hz, 2.0 Hz), 8.51 (1H, d, J=2.0 Hz), 8.74 (1H, brt, J=1.8 Hz)

Example 7

2-(2-Hydroxyethyl)amino-4-(3,4-methylenedioxybenzyl)amino-6,7,8-trimethoxyquinazoline

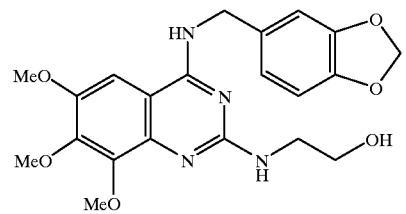

molecular formula; $C_{21}H_{24}N_4O_6$ yield (%); 38 m.p.(° C.); amorphous

Mass; 429 (M+H)$^+$

NMR δ(CDCl$_3$);

3.60 (2H, m), 3.88 (3H, s & 1H, m), 3.99 (3H, s), 4.01 (3H, s), 4.67 (2H, d, J=5.6 Hz), 5.32 (1H, brs), 5.53 (1H, brs), 5.97 (2H, s), 6.55 (1H, s), 6.80 (1H, d, J=8.0 Hz), 6.85 (1H, d, J=8.0 Hz), 6.89 (1H, s)

Example 8

2-(2-Hydroxyethyl)amino-4-(3,4-methylenedioxybenzyl)amino-6-chloroquinazoline

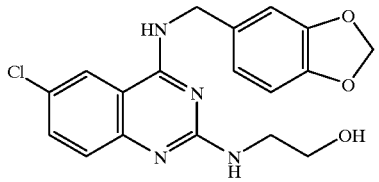

molecular formula; C₁₈H₁₇N₄O₃Cl yield (%); 47 m.p.(° C.); 138~139

Mass m/e; 373 (M+1)

NMR δ(CDCl₃(+DMSO-d₆));

3.60 (2H, m), 3.79 (2H, t, J=4.8 Hz), 4.65 (2H, d, J=5.2 Hz), 5.94 (2H, s), 6.76 (1H, d, J=8.0 Hz), 6.85 (1H, dd, J=8.0 Hz, 2.0 Hz), 6.90 (1H, d, J=2.0 Hz), 7.34 (1H, d, J=8.8 Hz), 7.44 (1H, dd, J=8.8 Hz, 2.4 Hz), 8.02 (2H, brs)

Example 9

2-[N-(2-Hydroxyethyl)-N-methylamino]-4-(3,4-methylenedioxybenzyl)amino-6-chloroquinazoline

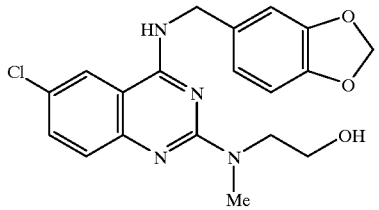

molecular formula; C₁₉H₁₉N₄O₃Cl yield (%); 48 m.p. (° C.); 146~148

Mass m/e; 387 (M+1)

NMR δ(CDCl₃(+DMSO-d₆));

3.27 (3H, s), 3.82 (2H, t, J=4.8 Hz), 3.89 (2H, t, J=4.8 Hz), 4.67 (2H, d, J=5.6 Hz), 5.95 (2H, s), 6.77 (1H, d, J=8.0 Hz), 6.86 (1H, dd, J=8.0 Hz, 1.6 Hz), 6.90 (1H, d, J=1.6 Hz), 7.43 (2H, m), 7.76 (1H, brs)

Example 10

2-(2-Hydroxymethylpyrrolidin-1-yl)-4-(3,4-methylenedioxybenzyl)amino-6-chloroquinazoline

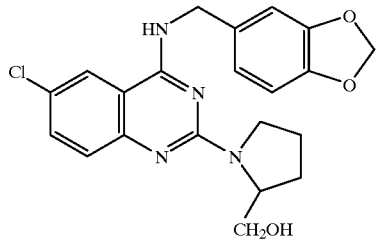

molecular formula; C₂₁H₂₁N₄O₃Cl (412.877)

yield (%); 70 m.p.(° C.); 182~183

Mass; 413 (MH⁺)

NMR δ(DMSO-d₆);

1.8~2.0 (4H, br 2 peaks), 3.4~3.7 (3H, br 2 peaks), 4.1~4.2 (1H, brs), 4.58 (2H, d, J=5.8 Hz), 5.96 (2H, s), 6.84 (1H, d, J=8.0 Hz), 6.88 (1H, dd, J=1.3 Hz, 8.0 Hz), 6.96 (1H, d, J=1.3 Hz), 7.23 (1H, d, J=8.8 Hz), 7.47 (1H, dd, J=2.4 Hz, 8.8 Hz), 8.15 (1H, d, J=2.4 Hz), 8.4~8.6 (1H, brs)

Example 11

2-Bis(2-hydroxyethyl)amino-4-(3,4-methylenedioxybenzyl)amino-6-chloroquinazoline

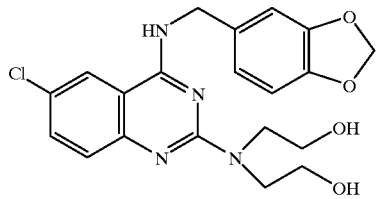

molecular formula; C₂₀H₂₁N₄O₄Cl (416.865)

yield (%); 56 m.p.(° C.); 167~168

Mass; 417 (MH⁺)

NMR δ(DMSO-d₆);

3.5~3.7 (8H, br 2 peaks), 4.56 (2H, d, J=5.7 Hz), 5.96 (2H, s), 6.85 (2H, s), 6.93 (1H, s), 7.22 (1H, d, J=9.0 Hz), 7.47 (1H, dd, J=2.4 Hz, 9.0 Hz), 8.15 (1H, d, J=2.4 Hz), 8.55 (1H, brt, J=5.7 Hz)

Example 12

2-(1-Imidazolyl)-4-(3,4-methylenedioxybenzyl)
amino-6-chloroquinazoline

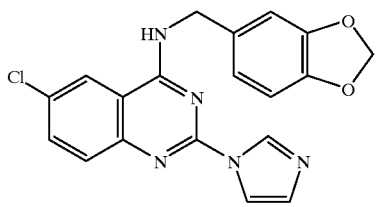

103 mg of imidazole was added to a suspension of 66 mg of sodium hydride in 6 ml of dimethylformamide at 0° C. The obtained mixture was stirred for 10 minutes. 500 mg of 2,6-dichloro-4-(3,4-methylenedioxybenzyl)amino-6-chloroquinazoline was added to the resulting mixture at room temperature. The mixture thus prepared was stirred at 100° C. for 20 minutes, followed by the addition of water. The crystals precipitated were recovered by filtration and washed with water and ethanol/acetone successively to give 325 mg of the title compound.

molecular formula; $C_{19}H_{14}N_5O_2Cl$ yield (%); 59 m.p.(° C.); 275~276 (dec.)

Mass m/e; 380 (M+1)

NMR δ(DMSO-$d_6$);

4.74 (2H, d, J=5.6 Hz), 5.96 (2H, s), 6.85 (1H, d, J=8.0 Hz), 6.95 (1H, dd, J=8.0 Hz, 1.6 Hz), 7.03 (1H, d, J=1.6 Hz), 7.08 (1H, d, J=1.2 Hz), 7.68 (1H, d, J=8.8 Hz), 7.78 (1H, dd, J=8.8 Hz, 2.4 Hz), 7.94 (1H, d, J=1.2 Hz), 8.47 (1H, d, J=2.4 Hz), 8.58 (1H, t, J=2.4 Hz), 9.28 (1H, t, J=5.6 Hz)

Examples 13 to 17

The following compounds were prepared in a similar manner to that of Example 12.

Example 13

2-(Imidazol-1-yl)-4-(3,4-methylenedioxybenzyl)
amino-6-cyanoquinazoline

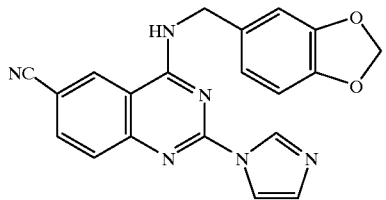

molecular formula; $C_{20}H_{14}N_6O_2$ (370)

yield (%); 81 m.p.(° C.); >290

Mass; 371 (M+1)$^+$

NMR δ(DMSO-$d_6$);

4.74 (2H, d, J=6.0 Hz), 5.95 (2H, s), 6.86 (1H, d, J=8.0 Hz), 6.95 (1H, dd, J=8.0 Hz, 1.6 Hz), 7.04 (1H, d, J=1.6 Hz), 7.09 (1H, d, J=1.6 Hz), 7.73 (1H, d, J=8.4 Hz), 7.95 (1H, d, J=1.6 Hz), 8.06 (1H, dd, J=8.4 Hz, 1.6 Hz), 8.61 (1H, d, J=1.6 Hz), 8.87 (1H, d, J=1.6 Hz), 9.47 (1H, brt, J=6.0 Hz)

Example 14

2-Pentylamino-4-(3,4-methylenedioxybenzyl)amino-
6-chloroquinazoline

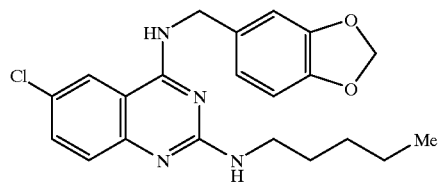

molecular formula; $C_{21}H_{23}N_4O_2Cl$ yield (%); 97 m.p.(° C.); 194~195

Mass m/e; 399 (M+1)

NMR δ(CDCl$_3$);

0.86 (3H, t, J=7.2 Hz), 1.29 (4H, m), 1.58 (2H, quintet, J=6.8 Hz), 3.47 (2H, q, J=6.8 Hz), 4.78 (2H, d, J=5.6 Hz), 5.87 (2H, s), 6.66 (1H, d, J=8.0 Hz), 6.89 (1H, d, J=8.0 Hz), 6.94 (1H, s), 7.26 (1H, d, J=8.8 Hz), 7.41 (1H, d, J=8.8 Hz), 7.90 (1H, t, J=5.6 Hz), 8.55 (1H, s), 9.53 (1H, brs)

Example 15

2-(2-Aminoethyl)amino-4-(3,4-
methylenedioxybenzyl)amino-6,7,8-
trimethoxyquinazoline

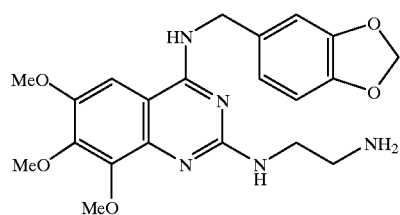

molecular formula; $C_{21}H_{25}N_5O_5$ yield (%); 87 m.p.(° C.); amorphous

Mass; 428 (M+H)$^+$

NMR δ(CDCl$_3$);

1.44 (2H, s), 2.93 (2H, t, J=6.0 Hz), 3.57 (2H, brs), 3.88 (3H, s), 4.00 (3H, s), 4.07 (3H, s), 4.70 (2H, d, J=4.8 Hz), 5.16 (1H, brs), 5.51 (1H, brs), 5.96 (2H, s), 6.56 (1H, s), 6.80 (1H, d, J=8.0 Hz), 6.86 (1H, d, J=8.0 Hz), 6.90 (1H, s)

Example 16

2-Hydrazino-4-(3,4-methylenedioxybenzyl)amino-6,7,8-trimethoxyquinazoline

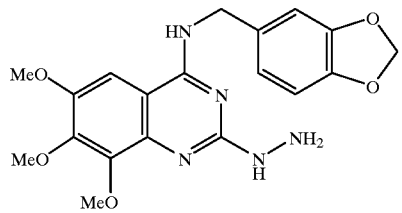

molecular formula; $C_{19}H_{21}N_5O_5$
yield (%); 12
m.p.(° C.); oily substance
Mass; 400 (M+H)$^+$
NMR δ(CDCl$_3$);
3.88 (3H, s), 3.99 (3H, s), 4.05 (3H, s), 4.66 (2H, d, J=3.6 Hz), 5.92 (2H, s), 6.75 (1H, d, J=8.0 Hz), 6.83 (1H, d, J=8.0 Hz), 6.87 (1H, s), 7.04 (2H, brs)

Example 17

2-(Carbamoylmethyl)amino-4-(3,4-methylenedioxybenzyl)amino-6-chloroquinazoline

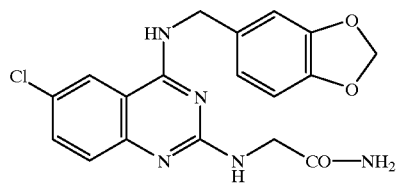

molecular formula; $C_{18}H_{16}N_53Cl$
yield (%); 63
m.p.(° C.); 259~260 (dec.)
Mass m/e; 386 (M+1)
NMR δ(DMSO-d$_6$);
4.02 (2H, d, J=4.8 Hz), 4.66 (2H, d, J=5.6 Hz), 5.97 (2H, s), 6.86 (1H, d, J=8.0 Hz), 6.91 (1H, d, J=8.0 Hz), 6.99 (1H, s), 7.19 (1H, s), 7.50 (1H, d, J=8.8 Hz), 7.61 (1H, s), 7.83 (1H, d, J=8.8 Hz), 8.09 (1H, brs), 8.49 (1H, brs), 10.03 (1H, brs)

Example 18

2-(3,4-Methylenedioxybenzyl)amino-4,6,7,8-tetramethoxyquinazoline

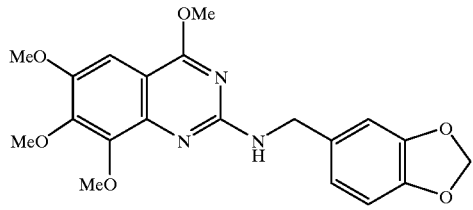

1.00 g (3.51 mmol) of 2-chloro-4,6,7,8-tetramethoxyquinazoline, 0.60 g (3.97 mmol) of piperonylamine and 0.60 g of sodium carbonate were mixed with 30 ml of isopropyl alcohol. The obtained mixture was heated under reflux for 24 hours and distilled under a reduced pressure to remove the solvent. The residue was purified by silica gel column chromatography (ethyl acetate/n-hexane) to give 0.12 g of the title compound as an oily substance.
molecular formula; $C_{20}H_{21}N_3O_6$
yield (%); 9
m.p.(° C.); oily substance
NMR δ(CDCl$_3$);
3.91 (3H, s), 4.02 (3H, s), 4.04 (6H, s), 4.63 (2H, d, J=6.0 Hz), 5.30 (1H, brs), 5.93 (2H, s), 6.75 (1H, d, J=8.0 Hz), 6.86 (1H, dd, J=8.0 Hz, 1.6 Hz), 6.92 (1H, d, J=1.6 Hz), 7.06 (1H, s)

Example 19

2-Chloro-4,6,7,8-tetramethoxyquinazoline

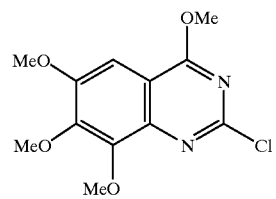

5.00 g (17.3 mmol) of 2,4-dichloro-6,7,8-trimethoxyquinazoline was suspended in 100 ml of methanol, followed by the gradual addition of 1.5 g of sodium hydride. The obtained mixture was heated under reflux. After several hours, the reaction mixture was concentrated under a reduced pressure, followed by the addition of water. The crystal thus precipitated was recovered by filtration, washed with water and air-dried to give 4.80 g of the title compound as a pale-pink crystal.
yield (%); 97
m.p.(° C.); 119~120
Mass; 285 (M+1)$^+$
NMR δ(CDCl$_3$);
3.98 (3H, s), 4.06 (3H, s), 4.12 (3H, s), 4.19 (3H, s), 7.17 (1H, s)

Example 20

2-Amino-4-(3,4-methylenedioxybenzyl)amino-6-chloroquinazoline

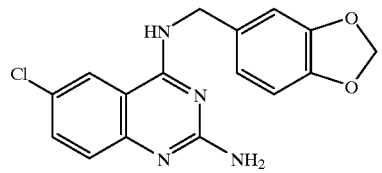

2.0 g of 2.6-dichloro-4-(3,4-methylenedioxybenzyl)aminoquinazoline was heated to 120° C. in 50 ml of ethanolic ammonia put in a pressure vessel for 18 hours, cooled and concentrated under a reduced pressure. The obtained residue was introduced to a silica gel column and eluted with a chloroform/methanol (9:1) mixture to give 830 mg of the title compound.
molecular formula; $C_{16}H_{13}N_4O_2Cl$ yield (%); 44
m.p.(° C.); 285 (dec.)
Mass; 329 (M+1)$^+$
NMR δ(CDCl$_3$);
4.67 (2H, d, J=5.6 Hz), 4.98 (2H, br), 5.74 (1H, br), 5.96 (2H, s), 6.78 (1H, d, J=7.6 Hz), 6.83 (1H, dd, J=7.6 Hz, 1.6 Hz), 6.86 (1H, d, J=1.6 Hz), 7.38 (1H, d, J=9.6 Hz), 7.46~7.49 (2H, m)

Example 21

2-Amino-4-(3,4-methylenedioxybenzyl)amino-6-cyanoquinazoline

The title compound was prepared in a similar manner to those of Examples 19 and 20.

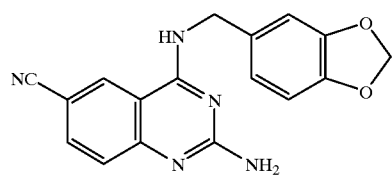

molecular formula; C$_{17}$H$_{13}$N$_5$O$_2$ (319)
yield (%); 60
m.p.(° C.); 284 (dec.)
Mass; 320 (M+1)$^+$
NMR δ(CDCl$_3$);
4.31 (2H, d, J=5.6 Hz), 5.25 (2H, brs), 5.58 (2H, s), 6.40 (1H, d, J=7.6 Hz), 6.51 (1H, dd, J=7.6 Hz, 1.2 Hz), 6.57 (1H, d, J=1.2 Hz), 6.95 (1H, d, J=8.4 Hz), 7.25 (1H, dd, J=8.4 Hz, 1.6 Hz), 8.00 (1H, br), 8.20 (1H, d, J=1.6 Hz)

Example 22

2-(Methylcarbamoyl)amino-4-(3,4-methylenedioxybenzyl)amino-6-chloroquinazoline

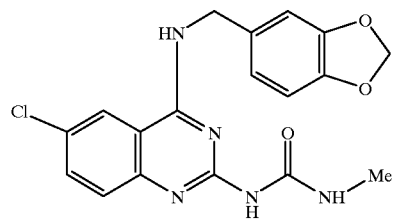

4 ml of dimethyl sulfoxide and 260 mg of methyl isocyanate were added to 500 mg of 2-amino-4-(3,4-methylenedioxybenzyl)amino-6-chloroquinazoline. The obtained mixture was stirred at 50° C. for 3 hours and distilled under a reduced pressure to remove excess methyl isocyanate, followed by the addition of chloroform and water. The mixture thus obtained was filtered and the filtrate was extracted with chloroform twice. The organic layers were combined, washed with water twice, dried over magnesium sulfate and distilled under a reduced pressure to remove the solvent. The residue was purified by silica gel column chromatography (benzene/acetone) and recrystallized (from benzene/chloroform/ethanol) to give 72 mg of the title compound.

molecular formula; C$_{18}$H$_{16}$N$_5$O$_3$Cl
yield (%); 12
m.p.(° C.); 245~247
Mass m/e; 386 (M+1)
NMR δ(DMSO-d$_6$);
2.75 (3H, d, J=4.4 Hz), 4.56 (2H, d, J=6.0 Hz), 5.95 (2H, s), 6.82 (1H, d, J=8.4 Hz), 6.92 (1H, d, J=8.4 Hz), 7.11 (1H, s), 7.56 (1H, d, J=8.8 Hz), 7.67 (1H, dd, J=8.8 Hz, 1.6 Hz), 8.27 (1H, d, J=1.6 Hz), 8.90 (1H, t, J=6.0 Hz), 9.20 (1H, s), 9.38 (1H, d, J=4.4 Hz)

Examples 23 and 24

The following compounds were prepared in a similar manner to that of Example 22.

Example 23

2-Bis(methylcarbamoyl)amino-4-(3,4-methylenedioxybenzyl)amino-6-chloroquinazoline

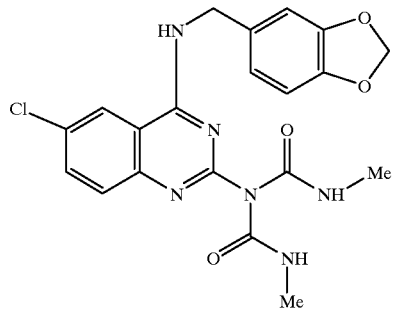

molecular formula; C$_{20}$H$_{19}$N$_6$O$_4$Cl
yield (%); 8
amt. of product (mg); 45
m.p.(° C.); 243~245
Mass m/e; 443 (M+1)
NMR δ(DMSO-d$_6$);
2.71 (6H, d, J=4.8 Hz), 4.53 (2H, d, J=6.0 Hz), 5.94 (2H, s), 6.80 (1H, d, J=8.0 Hz), 6.85 (1H, d, J=8.0 Hz), 6.95 (1H, s), 7.66 (1H, d, J=8.8 Hz), 7.72 (1H, dd, J=8.8 Hz, 2.0 Hz), 8.32 (1H, dd, J=2.0 Hz), 8.85 (1H, dd, J=4.8 Hz), 9.01 (1H, t, J=6.0 Hz)

Example 24

2-(n-Butylcarbamoyl)amino-4-(3,4-methylenedioxybenzyl)amino-6- chloroquinazoline

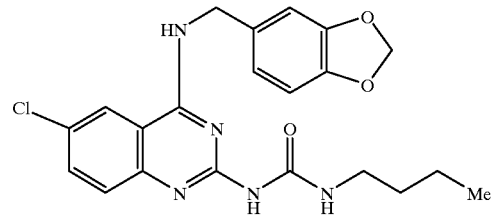

molecular formula; C$_{21}$H$_{22}$N$_5$O$_3$Cl
yield (%); 40
m.p.(° C.); 209~210

Mass m/e; 428 (M+1)

NMR δ(DMSO-d$_6$);

0.89 (3H, t, J=7.2 Hz), 1.33 (2H, sextet, J=7.2 Hz), 1.45 (2H, quintet, J=7.2 Hz), 3.18 (2H, t, J=7.2 Hz), 4.56 (2H, d, J=6.0 Hz), 5.95 (2H, s), 6.83 (1H, d, J=8.0 Hz), 6.91 (1H, d, J=8.0 Hz), 7.09 (1H, s), 7.46 (1H, d, J=8.8 Hz), 7.66 (1H, dd, J=8.8 Hz, 2.0 Hz), 8.27 (1H, d, J=2.0 Hz), 8.90 (1H, t, J=6.0 Hz), 9.17 (1H, s), 9.58 (1H, t, J=7.2 Hz)

Example 25

2-(4-Ethoxycarbonylpiperidino)-4-(3,4-methylenedioxybenzyl)amino-6-chloroquinazoline

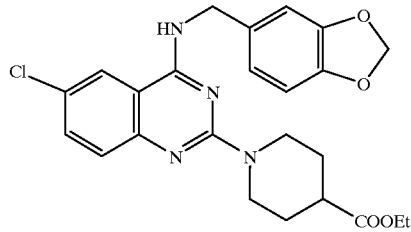

3.61 g of methyl isonipecotate, 2.32 g of triethylamine and 5 ml of 2-propanol were added to 1 g of 2,6-dichloro-4-(3,4-methylenedioxybenzyl)aminoquinazoline prepared in Example 92. The obtained mixture was refluxed for 100 minutes. The mixture thus obtained was extracted with chloroform twice. The organic layers were combined, washed with water, dried over magnesium sulfate and freed from the solvent by distillation. The residue was recrystallized (from ethanol/water) to give 1.31 g of the title compound.

molecular formula; $C_{24}H_{25}ClN_4O_4$ yield (%); 97 m.p.(° C.); 118~119

Mass; 469 (M+1)

NMR δ(DMSO-d$_6$);

1.18 (3H, t, J=7.2 Hz), 1.42 (2H, m), 2.58 (1H, m), 2.98 (2H, m), 4.06 (2H, q, J=7.2 Hz), 4.56 (2H, m, J=5.6 Hz), 4.62 (2H, m), 5.96 (2H, s), 6.82 (1H, d, J=8.0 Hz), 6.86 (1H, dd, J=8.0 Hz, 1.6 Hz), 6.94 (1H, d, J=1.6 Hz), 7.26 (1H, d, J=9.2 Hz), 7.48 (1H, dd, J=9.2 Hz, 2.4 Hz), 8.15 (1H, d, J=2.4 Hz), 8.56 (1H, brt, J=5.6 Hz)

Example 26

2-(4-Ethoxycarbonylpiperidino)-4-(3,4-methylenedioxybenzyl)amino-6-chloroquinazoline hydrochloride

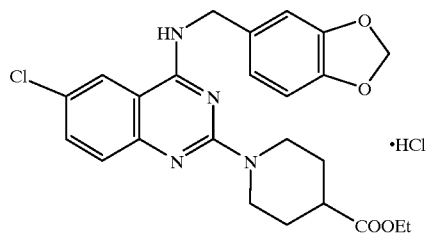

The title compound was prepared from the 2-(4-Ethoxycarbonylpiperidino)-4-(3,4-methylenedioxybenzyl) amino-6-chloroquinazoline prepared in Example 205 by the use of ethanol-hydrochloric acid-ethanol.

molecular formula; $C_{24}H_{25}ClN_4O_4 \cdot HCl$ yield (%); 97 m.p.(° C.); 174~175

NMR δ(DMSO-d$_6$);

1.20 (3H, t, J=7.2 Hz), 1.59 (2H, m), 1.97 (2H, m), 2.75 (1H, m), 3.31 (2H, m), 4.09 (2H, q, J=7.2 Hz), 4.53 (2H, m), 4.67 (2H, d, J=5.6 Hz), 5.98 (2H, s), 6.86 (1H, d, J=8.0 Hz), 6.90 (1H, dd, J=8.0 Hz, 1.6 Hz), 7.01 (1H, d, J=1.6 Hz), 7.83 (1H, dd, J=8.8 Hz, 2.0 Hz), 7.91 (1H, d, J=8.8 Hz), 8.52 (1H, d, J=2.0 Hz), 10.15 (1H, brs), 12.28 (1H, brs)

Example 27

2-(4-Ethoxycarbonylpiperidino)-4-(3,4-methylenedioxybenzyl)amino-6-cyanoquinazoline

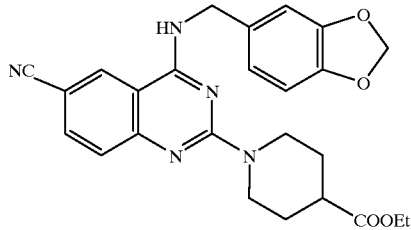

3.71 g of ethyl isonipecotate, 2.38 g of triethylamine and 10 ml of 2-propanol were added to 1 g of 2-chloro-4-(3,4-methylenedioxybenzyl) amino-6-cyanoquinazoline. The obtained mixture was refluxed for 1 hour and cooled to room temperature. The crystals thus precipitated were recovered by filtration and washed with water and ether successively to give 1.126 g of the title compound.

molecular formula; $C_{25}H_{25}N_5O_4$ yield (%); 83 m.p.(° C.); 192~193

Mass; 460 (M+1)

NMR δ(CDCl$_3$);

1.26 (3H, t, J=7.2 Hz), 1.71 (2H, m), 1.99 (2H, m), 2.59 (1H, m), 3.12 (2H, brt, J=12.0 Hz), 4.15 (2H, q, J=7.2 Hz), 4.67 (2H, d, J=5.2 Hz), 4.82 (2H, dt, J=13.2 Hz, 3.6 Hz), 5.96 (2H, s), 6.79 (1H, d, J=8.0 Hz), 6.85 (1H, dd, J=8.0 Hz, 1.6 Hz), 6.88 (1H, d, J=1.6 Hz), 7.42 (1H, brs), 7.61 (1H, dd, J=8.8 Hz, 1.6 Hz), 7.84 (1H, brs)

Example 28

2-(4-Ethoxycarbonylpiperidino)-4-(3-chloro-4-methoxybenzyl)amino-6-cyanoquinazoline

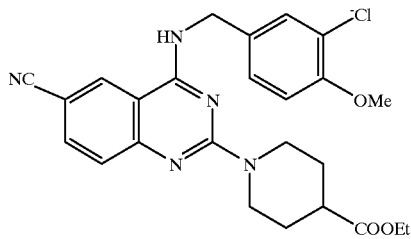

3.5 g of ethyl isonipecotate, 2.25 g of triethylamine and 30 ml of 2-propanol were added to 1 g of 2-chloro-4-(3-chloro- 4-methoxybenzyl)amino-6-cyanoquinazoline. The obtained mixture was refluxed for 30 minutes and cooled to room temperature. The crystals thus precipitated were recovered by filtration and washed with water and ethanol successively to give 1.13 g of the title compound.

molecular formula; $C_{25}H_{26}N_5O_3Cl$ yield (%); 85 m.p.(° C.); 202~203

Mass; 480 (M+1)

NMR δ(CDCl$_3$);

1.26 (3H, t, J=7.2 Hz), 1.72 (2H, m), 1.99 (2H, m), 2.59 (1H, m), 3.13 (2H, brt, J=11.2 Hz), 3.90 (3H, s), 4.15 (2H, q, J=7.2 Hz), 4.69 (2H, d, J=5.6 Hz), 4.80 (2H, m), 6.91 (1H, d, J=8.4 Hz), 7.25 (1H, dd, J=8.4 Hz, 2.4 Hz), 7.42 (1H, d, J=2.4 Hz), 7.43 (1H, brs), 7.61 (1H, dd, J=8.8 Hz, 1.6 Hz), 7.87 (1H, brs)

Example 29

2-[N-(3-Ethoxycarbonylpropyl)-N-methylamino]-4-(3,4-methylenedioxybenzyl)amino-6-cyanoquinazoline

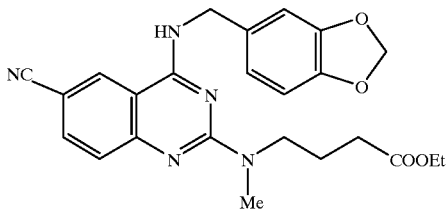

858 mg of ethyl N-methyl-4-aminobutyrate hydrochloride, 238 mg of triethylamine, 4 ml of 2-propanol and 2 ml of N,N-dimethylformamide were added to 400 mg of 2-chloro-4-(3,4-methylenedioxybenzyl)amino-6-cyanoquinazoline. The obtained mixture was refluxed for 1 hour, cooled to room temperature and filtered. The filtrate was distilled under a reduced pressure to remove the solvent and the residue was recrystallized (from ethanol/water) to give 410 mg of the title compound.

molecular formula; $C_{24}H_{25}N_5O_4$ yield (%); 78 m.p.(° C.); 152~153

Mass; 448 (M+1)

NMR δ(CDCl$_3$);

1.22 (3H, t, J=6.8 Hz), 1.97 (2H, brs), 2.30 (2H, brs), 3.24 (3H, s), 3.75 (2H, brs), 4.10 (2H, q, J=6.8 Hz), 4.68 (2H, d, J=5.2 Hz), 5.96 (2H, s), 6.79 (1H, d, J=8.0 Hz), 6.84 (1H, d, J=8.0 Hz), 6.87 (1H, s), 7.42 (1H, brs), 7.60 (1H, d, J=8.8 Hz), 7.81 (1H, brs)

Examples 30 to 41

The following compounds were prepared in a similar manner to that of Examples 25 to 29.

Example 30

2-(4-Ethoxycarbonylpiperidino)-4-(3,4-methylenedioxybenzyl)amino-6,7,8-trimethoxyquinazoline hydrochloride

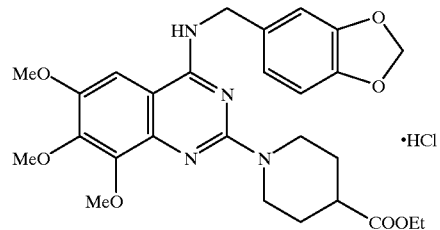

molecular formula; $C_{27}H_{32}N_4O_7 \cdot HCl$ yield (%); 65 m.p.(° C.); 148~150

Mass; 525 (M+1)

NMR δ(CDCl$_3$);

1.275 (3H, t, J=7.2 Hz), 1.76 (2H, m), 2.03 (2H, m), 2.63 (1H, m), 3.38 (2H, m), 3.99 (3H, s), 4.08 (3H, s), 4.12 (3H, s), 4.17 (2H, q, J=7.2 Hz), 4.28 (2H, m), 4.63 (2H, d, J=6.0 Hz), 5.88 (2H, s), 6.68 (1H, d, J=8.0 Hz), 6.92 (1H, dd, J=8.0 Hz, 1.6 Hz), 6.97 (1H, d, J=1.6 Hz), 8.23 (1H, s), 9.38 (1H, brs), 11.1 (1H, s)

Example 31

2-(4-Ethoxycarbonylpiperidino)-4-(3-chloro-4-methoxybenzyl)amino-6,7,8-trimethoxyquinazoline hydrochloride

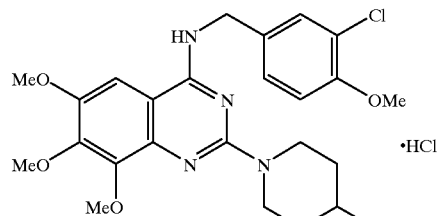

molecular formula; $C_{27}H_{33}N_4O_6Cl \cdot HCl$ yield (%); 93 m.p.(° C.); 177~178

Mass; 545 (M+1)

NMR δ(CDCl$_3$);

1.27 (3H, t, J=7.2 Hz), 1.80 (2H, m), 2.06 (2H, m), 2.67 (1H, m), 3.40 (2H, m), 3.82 (3H, s), 3.98 (3H, s), 4.07 (3H, s), 4.11 (3H, s), 4.17 (2H, q, J=7.2 Hz), 4.27 (2H, m), 4.65 (2H, d, J=6.0 Hz), 6.84 (1H, d, J=8.8 Hz), 7.40 (1H, d, J=2.0 Hz), 7.48 (1H, dd, J=8.8 Hz, 2.0 Hz), 8.23 (1H, s), 9.26 (1H, s), 11.27 (1H, brs)

Example 32

2-(4-Ethoxycarbonylpiperidino)-4-(3-chloro-4-methoxybenzyl)amino-6-chloroquinazoline hydrochloride

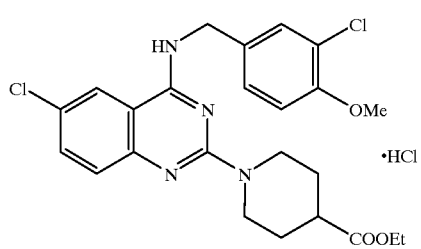

molecular formula; $C_{24}H_{26}N_4O_3Cl_2 \cdot HCl$ yield (%); 97 m.p.(° C.); 201~204

Mass; 489 (M+1)

NMR δ(DMSO-$d_6$);

1.17 (3H, t, J=7.2 Hz), 1.56 (2H, m), 1.93 (2H, m), 2.71 (1H, m), 3.30 (2H, m), 3.80 (3H, s), 4.06 (2H, q, J=7.2 Hz), 4.48 (2H, m), 4.66 (2H, d, J=5.2 Hz), 7.09 (1H, d, J=8.4 Hz), 7.34 (1H, dd, J=8.4 Hz, 2.0 Hz), 7.49 (1H, d, J=2.0 Hz), 7.83 (2H, brs), 8.48 (1H, brs), 10.8 (1H, brs)

Example 33

2-(Ethoxycarbonylmethyl)amino-4-(3,4-methylenedioxybenzyl)amino-6-chloroquinazoline

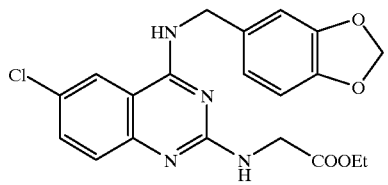

molecular formula; $C_{20}H_{19}N_4O_4Cl$ yield (%); 55 m.p.(° C.); 218~219 (dec.)

Mass m/e; 415 (M+1)

NMR δ(DMSO-$d_6$);

1.13 (3H, t, J=7.2 Hz), 4.07 (2H, q, J=7.2 Hz), 4.18 (2H, brs), 4.63 (2H, brd, J=4.0 Hz), 5.97 (2H, s), 6.85~6.92 (3H, m), 7.53 (1H, brs), 7.84 (1H, brd, J=8.0 Hz), 8.35 (1H, brs), 8.50 (2H, m)

Example 34

2-(3-Ethoxycarbonylpropyl)amino-4-(3,4-methylenedioxybenzyl)amino-6-chloroquinazoline

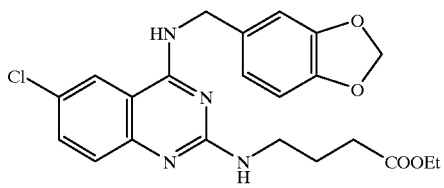

molecular formula; $C_{22}H_{23}N_4O_4Cl$ yield (%); 44 m.p.(° C.); 96~98

Mass m/e; 443 (M+1)

NMR δ(CDCl$_3$);

1.24 (3H, t, J=6.8 Hz), 1.96 (2H, quintet, J=7.2 Hz), 2.41 (2H, t, J=7.2 Hz), 3.54 (2H, q, J=7.2 Hz), 4.12 (2H, q, J=6.8 Hz), 4.66 (2H, q, J=5.2 Hz), 5.97 (2H, s), 6.79 (1H, d, J=8.0 Hz), 6.84 (1H, d, J=8.0 Hz), 6.87 (1H, s), 7.30 (1H, d, J=8.0 Hz), 7.44 (1H, s), 7.47 (1H, d, J=8.0 Hz)

Example 35

2-[N-(3-Ethoxycarbonylpropyl)-N-methylamino]-4-(3,4-methylenedioxybenzyl)amino-6-chloroquinazoline hydrochloride

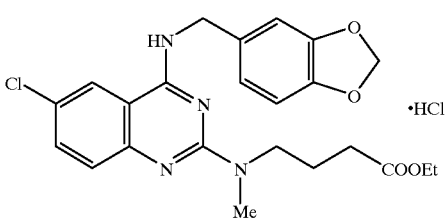

molecular formula; $C_{23}H_{25}N_4O_4Cl \cdot HCl$ yield (%); 67 m.p.(° C.); 182~183

Mass; 457 (M+1)

NMR δ(CDCl$_3$+DMSO-$d_6$);

1.23 (3H, t, J=7.2 Hz), 1.90 (2H, brs), 2.25 (2H, brs), 2.84 (3H, brs), 3.56 (2H, brs), 4.10 (2H, q, J=7.2 Hz), 4.70 (2H, d, J=5.6 Hz), 5.94 (2H, s), 6.76 (1H, d, J=7.6 Hz), 6.87 (2H, m), 7.54 (1H, dd, J=9.2 Hz, 2.0 Hz), 8.40 (1H, d, J=2.0 Hz), 8.66 (1H, d, J=9.2 Hz), 9.69 (1H, brs)

Example 36

2-(5-Ethoxycarbonylpentyl)amino-4-(3,4-methylenedioxybenzyl)amino-6-chloroquinazoline

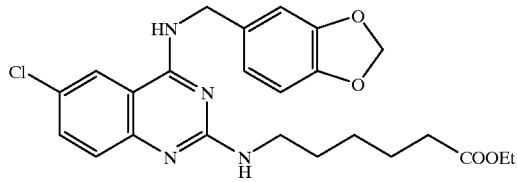

molecular formula; $C_{24}H_{27}N_4O_4Cl$ yield (%); 46 m.p.(° C.); 109~110

Mass m/e; 471 (M+1)

NMR δ(CDCl$_3$);

1.25 (3H, t, J=7.2 Hz), 1.43 (2H, quintet, J=7.6 Hz), 1.66 (4H, m), 2.31 (2H, t, J=7.6 Hz), 3.49 (2H, q, J=7.6 Hz), 4.12 (2H, q, J=7.2 Hz), 4.68 (2H, d, J=5.2 Hz), 5.97 (2H, s), 6.79 (1H, d, J=8.0 Hz), 6.84 (1H, d, J=8.0 Hz), 6.87 (1H, s), 7.43 (3H, m)

Example 37

(S)-2-(N-2-Ethoxycarbonylpyrrolidin-1-yl)-4-(3,4-methylenedioxybenzyl)amino-6-chloroquinazoline hydrochloride

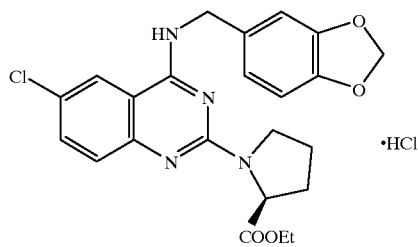

molecular formula; $C_{23}H_{23}N_4O_4Cl \cdot HCl$ yield (%); 52 m.p.(° C.); 206~208

Mass; 455 (M+1)

NMR δ(CDCl$_3$);

1.19 (3H, t, J=7.2 Hz), 2.17 (3H, m), 2.32 (1H, m), 4.12 (2H, m), 4.24 (2H, m), 4.62 (2H, m), 4.67 (1H, m), 5.93 (2H, s), 6.77 (1H, d, J=8.0 Hz), 6.86 (1H, dd, J=8.0 Hz, 1.6 Hz), 6.89 (1H, d, J=1.6 Hz), 7.54 (1H, d, J=8.8 Hz), 8.38 (1H, s), 8.64 (1H, d, J=8.8 Hz), 9.67 (1H, brs), 13.38 (1H, brs)

Example 38

2-(N-Ethoxycarbonylmethyl-N-methylamino)-4-(3,4-methylenedioxybenzyl)amino-6-cyanoquinazoline

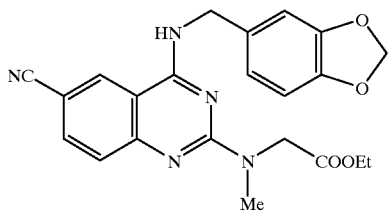

molecular formula; $C_{22}H_{21}N_5O_4$ yield (%); 75 m.p.(° C.); 171~172

Mass; 420 (M+1)

NMR δ(DMSO-d$_6$);

1.12 (3H, m), 3.18 (3H, s), 4.03 (2H, m), 4.38 (2H, m), 4.51 (2H, m), 5.95 (2H, s), 6.84 (3H, m), 7.30 (1H, m), 7.76 (1H, m), 8.58 (1H, s), 8.79 (1H, m)

Example 39

2-[N-Ethyl-N-(3-ethoxycarbonylpropyl)amino]-4-(3,4-methylenedioxybenzyl)amino-6-cyanoquinazoline

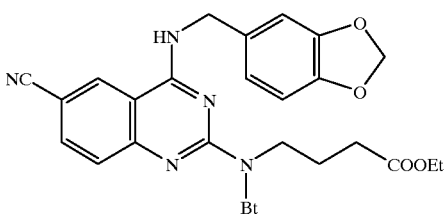

molecular formula; $C_{25}H_{27}N_5O_4$ (461.522)

yield (%); 61 m.p.(° C.); 142~143

Mass; 462 (M+1)

NMR δ(DMSO-d$_6$);

1.0~1.15 (3H, br 2 peaks), 1.13 (3H, t, J=7.1 Hz), 1.65~1.9 (2H, br 2 peaks), 2.15~2.35 (2H, br 2 peaks), 3.58 (4H, brs), 4.01 (2H, q, J=7.1 Hz), 4.58 (2H, d, J=5.7 Hz), 5.96 (2H, s), 6.84 (2H, s), 6.93 (1H, s), 7.25 (1H, brs), 7.72 (1H, dd, J=1.8 Hz, 8.8 Hz), 8.56 (1H, d, J=1.8 Hz), 8.72 (1H, t, J=5.7 Hz)

Example 40

2-[N-(3-Ethoxycarbonylpropyl)-N-methylaminol-4-(3-chloro-4-methoxybenzyl)amino-6-cyanoquinazoline

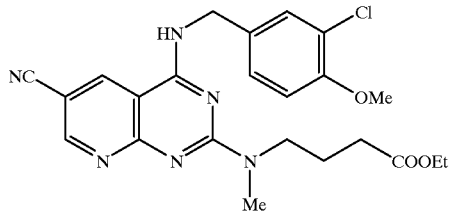

molecular formula; $C_{24}H_{26}N_5O_3Cl$ yield (%); 72 m.p.(° C.); 127~128

Mass; 468 (M+1)

NMR δ(DMSO-$d_6$);

1.11 (3H, t, J=7.2 Hz), 1.74 (2H, brs), 2.14 (2H, brs), 3.09 (3H, s), 3.62 (2H, brs), 3.81 (3H, s), 3.98 (2H, q, J=7.2 Hz), 4.61 (2H, d, J=6.0 Hz), 7.07 (1H, d, J=8.8 Hz), 7.20~7.36 (2H, m), 7.42 (1H, s), 7.72 (1H, d, J=8.8 Hz), 8.55 (1H, s), 8.75 (1H, t, J=6.0 Hz)

Example 41

(S)-2-(N-2-Ethoxycarbonylpyrrolidin-1-yl)-4-(3,4-methylenedioxybenzyl)amino-6-cyanoquinazoline hydrochloride

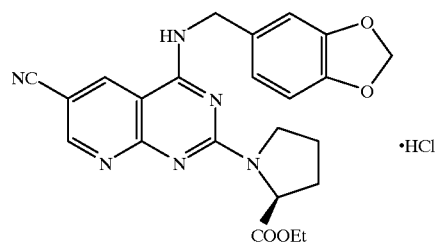

molecular formula; $C_{24}H_{23}N_5O_4 \cdot HCl$ yield (%); 44 m.p.(° C.); 231~232

Mass; 446 (M+1)

NMR δ(CDCl$_3$);

1.21 (3H, t, J=7.2 Hz), 2.19 (3H, m), 2.36 (1H, m), 4.15 (2H, m), 4.28 (2H, m), 4.62 (2H, m), 4.76 (1H, m), 5.95 (2H, s), 6.79 (1H, d, J=8.0 Hz), 6.86 (1H, d, J=8.0 Hz), 6.88 (1H, s), 7.80 (1H, dd, J=8.8 Hz, 1.6 Hz), 8.82 (1H, d, J=1.6 Hz), 8.87 (1H, d, J=8.8 Hz), 9.85 (1H, brs), 13.81 (1H, s)

Example 42

2-(4-Carboxypiperidino)-4-3,4-methylenedioxybenzyl)amino-6-chloroquinazoline

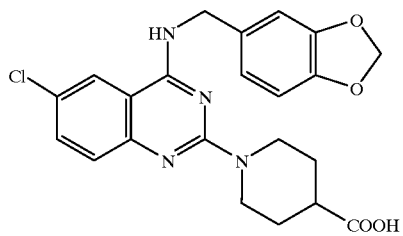

10 ml of ethanol, 5 ml of water and 820 mg of sodium hydroxide were added to 1 g of 2-(4-ethoxycarbonylpiperidino)-4-(3,4-methylenedioxybenzyl)amino-6-chloroquinazoline. The obtained mixture was refluxed for 20 minutes, concentrated under a reduced pressure and neutralized with 1 N hydrochloric acid. The crystals thus precipitated were recovered by filtration to give 920 mg of the title compound.

molecular formula; $C_{22}H_{21}N_4O_4Cl$ yield (%); 98 m.p.(° C.); 221~222

Mass m/e; 441 (M+1)

NMR δ(DMSO-$d_6$);

1.38 (2H, m), 1.80 (2H, dd, J=13.2 Hz, 2.4 Hz), 2.48 (1H, m), 2.96 (2H, t, J=12.0 Hz), 4.54 (2H, d, J=5.6 Hz), 4.56 (2H, dt, J=12.0 Hz, 3.2 Hz), 5.94 (2H, s), 6.81 (1H, d, J=8.0 Hz), 6.84 (1H, d, J=8.0 Hz), 6.93 (1H, s), 7.24 (1H, d, J=9.2 Hz), 7.46 (1H, dd, J=9.2 Hz, 2.0 Hz), 8.13 (1H, d, J=2.0 Hz), 8.55 (1H, t, J=5.6 Hz)

Example 43

Sodium 2-(4-Carboxypiperidino)-4-(3,4-methylenedioxybenzyl)amino-6-chloroquinazoline

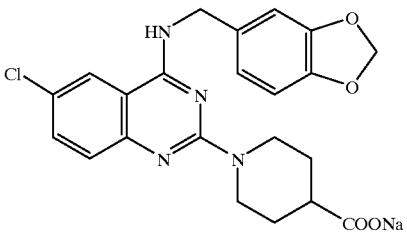

12 ml of a 1N aqueous solution of sodium hydroxide and 40 ml of water were added to 5.00 g (11.3 mmol) of the 2-(4-carboxypiperidino)-4-(3,4-methylenedioxybenzyl)amino-6-chloroquinazoline prepared in Example 222. The obtained mixture was dissolved by heating and cooled by allowing to stand. The crystals thus precipitated were recovered by filtration under suction, washed with a small amount of water, and vacuum-dried in the presence of phosphorus pentaoxide to give 4.34 g of the title compound.

molecular formula; $C_{22}H_{20}ClN_4O_4Na$ yield (%); 98

NMR δ(DMSO-$d_6$);

1.42(2H, m), 1.73(2H, m), 2.06(1H, M), 2.95(2H, M), 4.52(2H, m), 4.56(2H, d, J=5.6 Hz), 5.95(2H, s), 6.81(1H, d,

J=8.0 Hz), 6.86(1H, dd, J=8.0 Hz, 1.6 Hz), 6.95(1H, d, J=1.6 Hz), 7.22(1H, d, J=9.2 Hz), 7.44(1H, dd, J=9.2 Hz, 2.4 Hz), 8.13(1H, d, J=2.4 Hz), 8.58(1H, brt, J=5.6 Hz)

Example 44

Potassium 2-(4-Carboxypiperidino)-4-(3,4-methylenedioxybenzyl)amino-6-chloroquinazoline

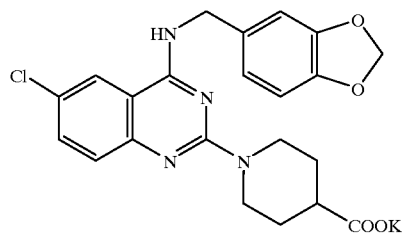

12.5 ml of a 1N aqueous solution of potassium hydroxide and 40 ml of water were added to 5.50 g (12.5 mmol) of the 2-(4-carboxypiperidino)-4-(3,4-methylenedioxybenzylamino)-6-chloroquinazoline prepared in Example 222. The obtained mixture was dissolved by heating and filtered. The filtrate was concentrated in a vacuum. Ethanol and ether were added to the obtained residue to precipitate crystals. The crystals were recovered by filtration, washed with ether, and vacuum-dried in the presence of phosphorus pentaoxide to give 4.69 g of the title compound.

molecular formula; $C_{22}H_{20}ClN_4O_4K$
yield (%); 78
m.p.(° C.); 230~234 (dec.)
NMR δ(DMSO-$d_6$);
1.39 (2H, m), 1.69 (2H, m), 1.96 (1H, m), 2.94 (2H, m), 4.48 (2H, m), 4.55 (2H, d, J=5.6 Hz), 5.96 (2H, s), 6.81 (1H, d, J=8.0 Hz), 6.86 (1H, dd, J=8.0 Hz, 1.6 Hz), 6.94 (1H, d, J=1.6 Hz), 7.22 (1H, d, J=8.8 Hz), 7.43 (1H, dd, J=8.8 Hz, 2.4 Hz), 8.11 (1H, d, J=2.4 Hz), 8.50 (1H, brt, J=5.6 Hz)

Example 45

2-(4-Carboxypiperidino)-4-(3,4-methylenedioxybenzyl)amino-6-chloroquinazoline hydrochloride

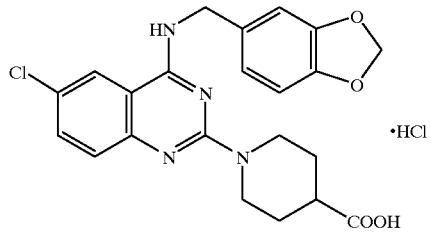

2.00 g (4.54 mmol) of the 2-(4-carboxypiperidino)-4-(3,4-methylenedioxybenzyl)amino-6-chloroquinazoline prepared in Example 222 was dissolved in a mixture comprising 25 ml of tetrahydrofuran and 25 ml of ethanol under heating, followed by the dropwise addition of 1.0 ml of an 8M ethanolic solution of hydrochloric acid. The obtained mixture was cooled by allowing to stand to precipitate crystals. The crystals were recovered by filtration, washed with tetrahydrofuran, and air-dried to give 1.87 g of the title compound.

molecular formula; $C_{22}H_{21}N_4O_4Cl\cdot HCl$
yield (%); 86
m.p.(° C.); 284~286
NMR δ(DMSO-$d_6$);
1.58 (2H, m), 1.96 (2H, m), 2.65 (1H, m), 3.3 (2H, m), 4.47 (2H, m), 4.67 (2H, d, J=5.6 Hz), 5.98 (2H, s), 6.87 (1H, d, J=8.0 Hz), 6.90 (1H, dd, J=8.0 Hz, 1.6 Hz), 7.00 (1H, d, J=1.6 Hz), 7.83 (2H, brs), 8.49 (1H, brs), 10.09 (1H, brs), 12.11 (1H, brs), 12.40 (1H, brs)

Example 46

2-(4-Carboxypiperidino)-4-(3,4-methylenedioxybenzyl)amino-6-chloroquinazoline methanesulfonate

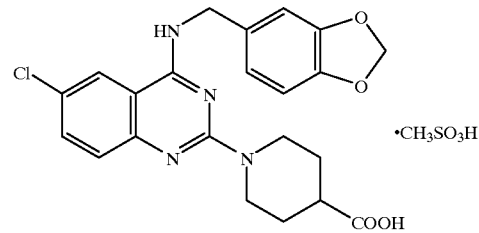

2.00 g (4.54 mmol) of the 2-(4-carboxypiperidino)-4-(3,4-methylenedioxybenzyl)amino-6-chloroquinazoline prepared in Example 222 was dissolved in a mixture comprising 25 ml of tetrahydrofuran and 25 ml of ethanol under heating, followed by the dropwise addition of 0.31 ml (4.78 mmol) of methanesulfonic acid. The obtained mixture was cooled by allowing to stand to precipitate crystals. The crystals were recovered by filtration, washed with tetrahydrofuran, and air-dried to give 2.21 g of the title compound.

molecular formula; $C_{22}H_{21}N_4O_4Cl\cdot CH_4O_3S$
yield (%); 91
m.p.(° C.); 265~266
NMR δ(DMSO-$d_6$);
1.59 (2H, m), 1.97 (2H, m), 2.32 (3H, s), 2.65 (1H, m), 3.3 (2H, m), 4.40 (2H, m), 4.68 (2H, d, J=5.6 Hz), 5.98 (2H, s), 6.87 (1H, d, J=8.0 Hz), 6.90 (1H, dd, J=8.0 Hz, 1.6 Hz), 6.98 (1H, d, J=1.6 Hz), 7.67 (1H, d, J=8.8 Hz), 7.84 (1H, dd, J=8.0 Hz, 2.0 Hz), 8.42 (1H, d, J=2.0 Hz), 9.95 (1H, brs), 11.76 (1H, brs), 12.37 (1H, brs)

Example 47

2-(4-Carboxypiperidino)-4-(3,4-methylenedioxybenzyl)amino-6-cyanoquinazoline

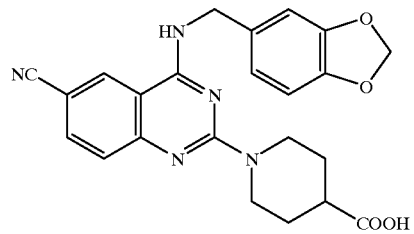

20 ml of ethanol and 2.0 ml of a 1N aqueous solution of sodium hydroxide were added to 318 mg of 2-(4- ethoxycarbonylpiperidino)-4-(3,4-methylenedioxybenzyl) amino-6-cyanoquinazoline. The obtained mixture was stirred at 50° C. for 30 minutes and neutralized with 1N hydrochloric acid. The crystal thus precipitated was recovered by filtration and purified by silica gel column chromatography (chloroform/methanol) to give 116 mg of the title compound.

molecular formula; $C_{23}H_{21}N_5O_4$ yield (%); 39 m.p.(° C.); 269~271

Mass m/e; 432(M+1)

NMR δ(DMSO-$d_6$);

1.40 (2H, m), 1.79 (2H, m), 2.41 (1H, m), 3.04 (1H, dt, J=11.2 Hz, 1.2 Hz), 4.55 (2H, d, J=5.6 Hz), 4.57 (2H, m), 5.95 (2H, s), 6.82 (1H, d, J=8.0 Hz), 6.84 (1H, d, J=8.0 Hz), 6.94 (1H, s), 7.25 (1H, d, J=8.8 Hz), 7.71 (1H, d, J=8.8 Hz), 8.53 (1H, s), 8.72 (1H, t, J=5.6 Hz)

Example 48

2-(4-Carboxypiperidino)-4-(3-chloro-4-methoxybenzyl)amino-6-cyanoquinazoline

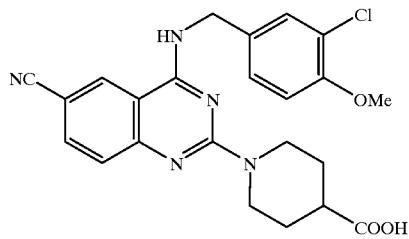

30 ml of tetrahydrofuran, 30 ml of ethanol and 14 ml of a 1N aqueous solution of sodium hydroxide were added to 1.0 g of 2-(4-ethoxycarbonylpiperidino)-4-(3-chloro-4-methoxybenzyl)amino-6-cyanoquinazoline. The obtained mixture was stirred at room temperature for 16 hours and neutralized with 1 N hydrochloric acid, followed by the addition of 100 ml of water. The crystals thus precipitated were recovered by filtration and recrystallized from tetrahydrofuran/ethanol/water to give 860 mg of the title compound.

molecular formula; $C_{23}H_{22}N_5O_3Cl$ yield (%); 91 m.p.(° C.); 277~278 (dec.)

Mass m/e; 452 (M+1)

NMR δ(DMSO-$d_6$);

1.40 (2H, m), 1.84 (2H, m), 2.51 (1H, m), 3.05 (2H, dt, J=12 Hz, 2.4 Hz), 3.82 (3H, s), 4.59 (2H, d, J=5.6 Hz), 4.63 (2H, m), 7.08 (1H, d, J=8.4 Hz), 7.28 (1H, d, J=8.8 Hz), 7.32 (1H, dd, J=8.4 Hz, 2.0 Hz), 7.45 (1H,d, J=2.0 Hz), 7.74 (1H, dd, J=8.8 Hz, 2.0 Hz), 8.54 (1H, d, J=2.0 Hz), 8.79 (1H, t, J=5.6 Hz)

Example 49

Sodium 2-(4-Carboxypiperidino)-4-(3-chloro-4-methoxybenzyl)amino-6-cyanoquinazoline

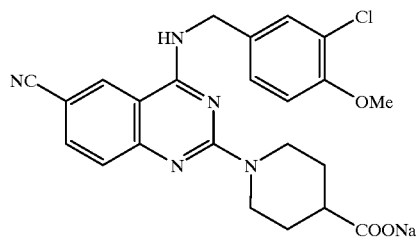

1.00 g (2.21 mmol) of the 2-(4-carboxypiperidino)-4-(3-chloro-4-methoxybenzyl)amino-6-cyanoquinazoline prepared in Example 228 was dissolved in a mixture comprising 30 ml of tetrahydrofuran and 40 ml of ethanol under heating, followed by the addition of 2.3 ml of a 1N aqueous solution of sodium hydroxide and 100 ml of water. The obtained mixture was concentrated in a vacuum to precipitate crystals. The crystals were recovered by filtration, washed with water, and air-dried to give 0.45 g of the title compound.

molecular formula; $C_{23}H_{21}N_5O_3ClNa$ yield (%); 43

NMR δ(DMSO-$d_6$);

1.45 (2H, m), 1.75 (2H, m), 2.12 (1H, m), 3.06 (2H, m), 3.81 (3H, s), 4.52 (2H, m), 4.58 (2H, d, J=5.6 Hz), 7.07 (1H, d, J=8.8 Hz), 7.24 (1H, d, J=8.4 Hz), 7.32 (1H, dd, J=8.4 Hz, 2.0 Hz), 7.45 (1H, d, J=2.0 Hz), 7.69 (1H, dd, J=8.8 Hz, 2.0 Hz), 8.54 (1H, d, J=2.0 Hz), 8.86 (1H, brt, J=5.6 Hz)

Example 50

2-[N-(3-Carboxypropyl)-N-methylamino]-4-(3,4-methylenedioxybenzyl)amino-6-cyanoquinazoline

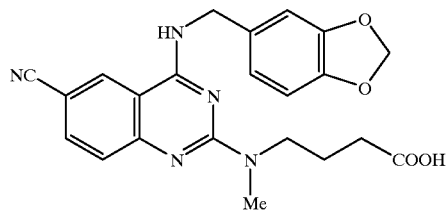

20 ml of ethanol and 2.61 ml of a 1N aqueous solution of sodium hydroxide were added to 389 mg of 2-[N-(3-ethoxycarbonylpropyl)-N-methoxyamino]-4-(3,4-methylenedioxybenzyl)amino-6-cyanoquinazoline. The obtained mixture was stirred at room temperature for 4 hours and at 50° C. for 10 minutes and neutralized with 1N hydrochloric acid. The crystals precipitated were recovered by filtration, purified by silica gel column chromatography (chloroform/methanol) and recrystallized from ethanol/acetone/water to give 305 mg of the title compound.

molecular formula; $C_{22}H_{21}N_5O_4$ yield (%); 84 m.p.(° C.); 138~140

Mass m/e; 420 (M+1)

NMR δ(CDCl$_3$(+DMSO-$d_6$));

1.96 (2H, brs), 2.31 (brs), 3.24 (3H, s), 3.76 (2H, brs), 4.67 (2H, d, J=5.6 Hz), 5.94 (2H, s), 6.77 (1H, d, J=8.0 Hz), 6.86 (1H, d, J=8.0 Hz), 6.91 (1H, s), 7.58 (1H, brs), 7.61 (1H, d, J=8.4 Hz), 8.48 (2H, m)

Examples 51 to 65

The following compounds were prepared in a similar manner to those of Examples 222 to 230.

Example 51

2-(4-Carboxypiperidino)-4-(3,4-methylenedioxybenzyl)amino-6,7,8-trimethoxyquinazoline

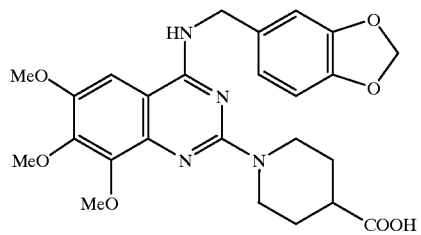

molecular formula; CH$_{25}$H$_{28}$N$_4$O$_7$ yield (%); 73 m.p.(° C.); 216~217

Mass m/e; 297 (M+1)

NMR δ(CDCl$_3$);

1.80 (2H, m), 2.05 (2H, m), 2.65 (1H, m), 3.39 (2H, dt, J=10.8 Hz, 2.8 Hz), 3.98 (3H, s), 4.07 (3H, s), 4.13 (3H, s), 4.26 (2H, m), 4.70 (2H, d, J=6.0 Hz), 5.88 (2H, s), 6.69 (1H, d, J=7.6 Hz), 6.95 (1H, dd, J=7.6 Hz, 1.6 Hz), 7.02 (1H, d, J=1.6 Hz), 8.38 (1H, s), 9.36 (1H, s), 11.24 (1H, t, J=6.0 Hz)

Example 52

2-(4-Carboxypiperidino)-4-(3-chloro-4-methoxybenzyl)amino-6,7,8-trimethoxyquinazoline

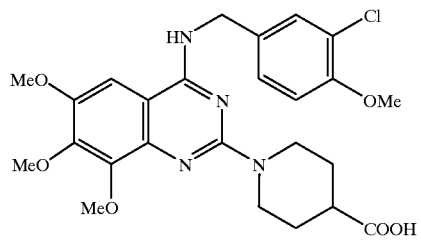

molecular formula; C$_{25}$H$_{23}$N$_4$O$_6$Cl yield (%); 90 m.p.(° C.); 197~198

Mass m/e; 517 (M+1)

NMR δ(DMSO-d$_6$);

1.45 (2H, brs), 1.90 (2H, brs), 2.59 (1H, brs), 3.22 (2H, brs), 3.80 (3H, s), 3.90 (6H, s), 3.92 (3H, s), 4.39 (2H, brs), 4.65 (2H, d, J=5.2 Hz), 7.05 (1H, d, J=8.4 Hz), 7.33 (1H, d, J=8.4 Hz), 7.45 (1H, s), 7.76 (1H, brs), 10.70 (1H, brs)

Example 53

2-(4-Carboxypiperidino)-4-(3,4-methylenedioxybenzyl)amino-6-methoxyquinazoline

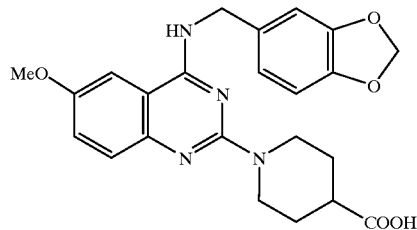

molecular formula; C$_{23}$H$_{24}$N$_4$O$_5$(436)

yield (%); 79 m.p.(° C.); 263 (dec.)

Mass; 437 (M+1)$^+$

NMR δ(DMSO-d$_6$);

1.51~1.59 (2H, m), 1.86~195 (2H, m), 2.59~2.64 (1H, m), 3.21~3.28 (2H, m), 4.39~4.44 (2H, m), 4.67 (2H, d, J=5.6 Hz), 5.78 (2H, s), 6.85 (1H, d, J=7.6 Hz), 6.89 (1H, d, J=7.6 Hz), 6.99 (1H, s), 7.42 (1H, dd, J=9.2 Hz, 1.6 Hz), 7.72 (1H, d, J=9.2 Hz), 7.86 (1H, d, J=1.6 Hz), 10.02 (1H, br), 11.89 (1H, s)

Example 54

2-(4-Carboxypiperidino)-4-(3-chloro-4-methoxybenzyl)amino-6-methoxyquinazoline

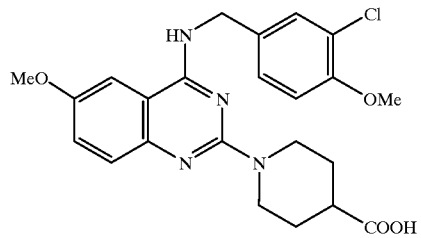

molecular formula; C$_{23}$H$_{25}$N$_4$O$_4$Cl (456.930)

yield (%); 81 m.p.(° C.); 245 (dec.)

Mass; 457 (MH$^+$)

NMR;

1.3~1.5 (2H, m), 1.79 (2H, d, J=10 Hz), 2.4~2.5 (1H, m), 2.91 (2H, t, J=11 Hz), 3.81 (3H, s ), 4.56 (2H, d, J=13 Hz), 4.60 (2H, d, J=5.7 Hz), 7.09 (1H, d, J=8.6 Hz), 7.18 (1H, dd, J=2.7 Hz, 9.2 Hz), 7.24 (1H, d, J=9.2 Hz), 7.32 (1H, dd, J=2.2 Hz, 8.6 Hz), 7.45 (1H, d, J=2.2 Hz), 7.49 (1H, d, J=2.7 Hz), 8.42 (1H, t, J=5.7 Hz), 12.15 (1H, brs)

Example 55

2-(4-Carboxypiperidino)-4-(3-chloro-4-methoxybenzyl)amino-6-chloroquinazoline

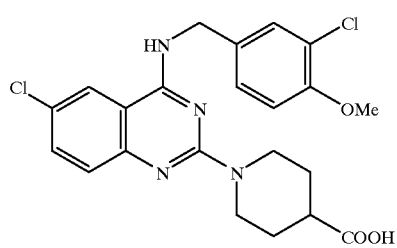

molecular formula; C<sub>22</sub>H<sub>22</sub>N<sub>4</sub>O<sub>3</sub>Cl<sub>2</sub> yield (%); 92 m.p.(° C.); 280~281

Mass m/e; 461 (M+1)

NMR δ(DMSO-d<sub>6</sub>);

1.59 (2H, M), 1.94 (2H brd, J=11.6 Hz), 2.62 (1H, brs), 3.32 (2H, m), 3.79 (3H, s), 4.52 (2H, d, J=13.6 Hz), 4.64 (2H, d, J=4.8 Hz), 6.99 (1H, d, J=8.4 Hz), 7.30 (1H, d, J=8.4 Hz), 7.42 (1H, s), 7.69 (1H, d, J=8.8 Hz), 8.00 (1H, d, J=8.8 Hz), 8.51 (1H, s), 10.24 (1H, s), 12.42 (1H, s)

Example 56

2-(4-Carboxypiperidino)-4-(benzimidazol-5-yl)methylamino-6-chloroquinazoline

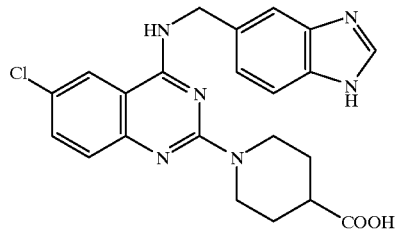

molecular formula; C<sub>22</sub>H<sub>21</sub>N<sub>6</sub>O<sub>2</sub>Cl (436.903)

yield (%); 99 m.p.(° C.); 230(dec.)

Mass; 437 (MH)<sup>+</sup>

NMR δ(DMSO-d<sub>6</sub>);

1.3~1.5 (2H, m), 1.82 (2H, d, J=10 Hz), 2.4~2.5 (1H, m), 2.98 (2H, t, J=11 Hz), 4.60 (2H, d, J=13 Hz), 4.77 (2H, d, J=5.7 Hz), 7.2~7.3 (2H, m), 7.45~7.6 (3H, m), 8.16 (1H, s), 8.19 (1H, d, J=2.4 Hz), 8.68 (1H, t, J=5.7 Hz), 12.17 (1H, brs), 12.33 (1H, brs)

Example 57

2-(Carboxymethyl)amino-4-(3,4-methylenedioxybenzyl)amino-6-chloroquinazoline

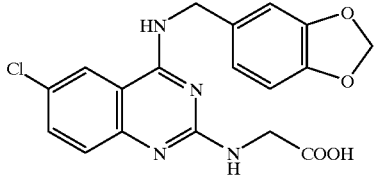

molecular formula; C<sub>18</sub>H<sub>15</sub>N<sub>4</sub>O<sub>4</sub>Cl yield (%); 64 m.p.(° C.); 260~261 (dec.)

Mass m/e; 387 (M+1)

NMR δ(DMSO-d<sub>6</sub>);

4.00 (2H, brs), 4.57 (2H, d, J=5.6 Hz), 5.93 (2H, s), 6.79 (1H, d, J=8.0 Hz), 6.86 (1H, d, J=8.0 Hz), 6.95 (1H, s), 7.35 (1H, brs), 7.50 (1H, brs), 8.30~8.50 (2H, m)

Example 58

2-(3-Carboxypropyl)amino-4-(3,4-methylenedioxybenzyl)amino-6-chloroquinazoline

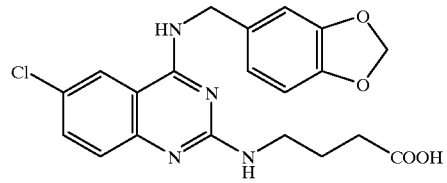

molecular formula; C<sub>20</sub>H<sub>19</sub>N<sub>4</sub>O<sub>4</sub>Cl yield (° C.); 88 m.p.(° C.); 170~172

Mass m/e; 415 (M+1)

NMR δ(DMSO-d<sub>6</sub>);

1.71 (2H, brs), 2.23 (2H, brs), 3.27 (2H, brs), 4.56 (2H, d, J=5.6 Hz), 5.95 (2H, s), 6.82 (3H, m), 6.95 (1H, s), 7.20 (1H, brs), 7.46 (1H, dd, J=8.8 Hz, 1.6 Hz), 8.12 (1H, d, J=1.6 Hz)

Example 59

2-(5-Carboxypentyl)amino-4-(3,4-methylenedioxybenzyl)amino-6-chloroquinazoline

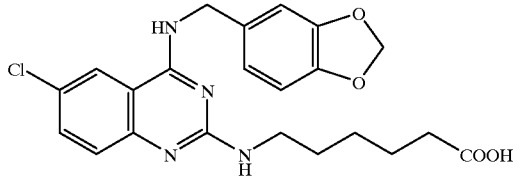

molecular formula; C<sub>22</sub>H<sub>23</sub>N<sub>4</sub>O<sub>4</sub>Cl yield (%); 80 m.p.(° C.); 190~192

Mass m/e; 443 (M+1)

NMR δ(DMSO-d<sub>6</sub>);

1.25 (2H, brs), 1.47 (4H, brs), 2.16 (2H, brs), 3.31 (2H, brs), 4.60 (2H, brs), 5.94 (2H, s), 6.84 (2H, s), 6.96 (1H, s), 7.33 (1H, brs), 7.60 (1H, brs), 8.25 (1H, brs)

Example 60

2-[N-(3-Carboxypropyl)-N-methylamino]-4-(3,4-methylenedioxybenzyl)amino-6-chloroquinazoline

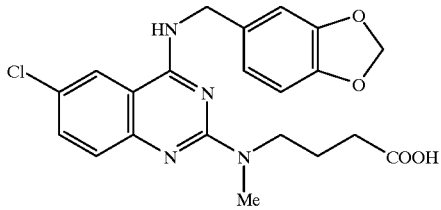

molecular formula; $C_{21}H_{21}N_4O_4Cl$ yield (%); 92 m.p.(° C.); 143~144

Mass m/e; 429 (M+1)

NMR δ(DMSO-d$_6$(+CD$_3$OD));

1.79 (2H, brs), 2.20 (2H, brs), 3.21 (3H, s), 3.71 (2H, t, J=7.2 Hz), 4.65 (2H, s), 5.95 (2H, s), 6.81 (1H, d, J=8.0 Hz), 6.86 (1H, d, J=8.0 Hz), 6.95 (1H, s), 7.79 (1H, d, J=8.8 Hz), 7.85 (1H, d, J=8.8 Hz), 8.49 (1H, s)

Example 61

2-(N-Carboxymethyl-N-methylamino)-4-(3,4-methylenedioxybenzyl)amino-6-cyanoquinazoline

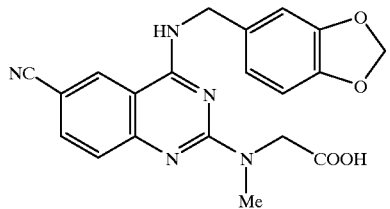

molecular formula; $C_{20}H_{17}N_5O_4$ yield (%); 68 m.p.(° C.); 268~270

Mass m/e; 392 (M+1)

NMR δ(DMSO-d$_6$);

3.11 (3H, s), 4.13 (2H, brs), 4.56 (2H, m), 5.94 (2H, s), 6.83 (2H, m), 6.93 (1H, d, J=14.4 Hz), 7.20 (1H, m), 7.66 (1H, m), 8.51 (1H, s), 8.62 (1H, m)

Example 62

2-[N-Ethyl-N-(3-carboxypropyl)amino]-4-(3,4-methylenedioxybenzyl)amino-6-cyanoquinazoline

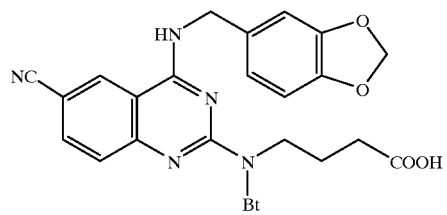

molecular formula; $C_{23}H_{23}N_5O_4$ (433.468)

yield (%); 96 m.p.(° C.); 186~187

Mass; 434 (M+1)

NMR δ(DMSOd$_6$);

1.0~1.15 (3H, br 2 peaks), 1.65~1.85 (2H, br 2 peaks), 2.1~2.25 (2H, br 2 peaks), 3.57 (4H, brs), 4.58 (2H, d, J=5.7 Hz), 5.96 (2H, s), 6.84 (2H, s), 6.93 (1H, s), 7.26 (1H, d, J=8.8 Hz), 7.72 (1H, dd, J=1.8 Hz, 8.8 Hz), 8.56 (1H, d, J=1.8 Hz), 8.71 (1H, brs)

Example 63

2-[N-(3-Carboxypropyl)-N-methylamino]-4-(3-chloro-4-methoxybenzyl)amino-6-cyanoquinazoline

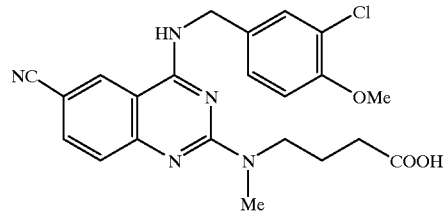

molecular formula; $C_{22}H_{22}N_5O_3Cl$ yield (%); 88 m.p.(° C.); 108~109

Mass; 440 (M+1)

NMR δ(DMSOd$_6$);

1.73 (2H,brs), 2.13 (2H, brs), 3.11 (3H,s), 3.63 (2H, brs), 3.82 (3H, s), 4.61 (2H, d, J=5.6 Hz), 7.07 (1H, d, J=8.4 Hz), 7.27 (1H, d, J=8.8 Hz), 7.31 (1H, d, J=8.4 Hz), 7.43 (1H, s), 7.72 (1H,s), 8.55 (1H,s), 8.74 (1H, brt, J=5.6 Hz), 12.02 (1H, brs)

Example 64

2-(4-Carboxypiperidino)-4-(benzimidazol-5-yl)methylamino-6-cyanoquinazoline

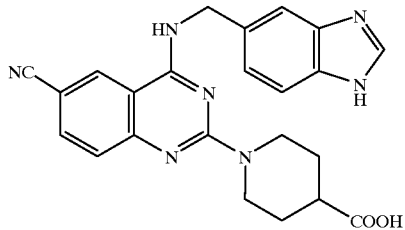

molecular formula; $C_{23}H_{21}N_7O_2$ (427)

yield (%); 50 m.p.(° C.); >290

Mass; 428 ($M^++1$)

NMR δ(DMSO-$d_6$);

1.29~1.42 (2H, m), 1.76~2.20 (2H,m), 2.39~2.51 (2H, m), 2.99~3.07 (3H, m), 4.60~4.64 (2H, m), 4.76 (2H, d, J=5.6 Hz), 7.23 (1H, d, J=8.4 Hz), 7.25 (1H, d, J=8.8 Hz), 7.51 (1H, d, J=8.4 Hz), 7.56 (1H,s), 7.71 (1H, dd, J=8.4 Hz, 1.6 Hz), 8.14 (1H, s), 8.57 (1H, d, J=1.6 Hz), 8.82 (1H, brt, J=5.6 Hz)

Example 65

2-(4-Carboxypiperidino)-4-(3,4-methylenedioxybenzyl)amino-6-carbamoylquinazoline

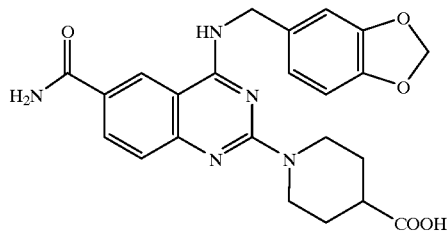

molecular formula; $C_{23}H_{23}N_5O_5$ (449)

yield (%); 6 m.p.(° C.); 180~182 (dec.)

Mass; 450 (M+1)

NMR δ(DMSO-$d_6$);

1.39 (2H, m), 1.81 (2H,m), 2.48 (1H,m), 2.99 (2H, m), 4.55 (2H, d, J=5.6 Hz), 4.62 (2H, m), 5.93 (2H, s), 6.81 (1H, d, J=7.6 Hz), 6.85 (1H, dd, J=7.6 Hz), 6.95 (1H, d, J=1.6 Hz), 7.20 (1H, d, J=8.8 Hz), 7.27 (1H, br), 7.71 (1H, br), 7.92 (1H, dd, J=8.8 Hz, 2.0 Hz), 8.57 (1H, d, J=2.0 Hz), 8.59 (1H, brt, J=5.6 Hz), 12.09 (1H, br)

Example 66

2-(4-Carboxypiperidino)-4-(3,4-methylenedioxybenzyl)oxy-6-chloroquinazoline

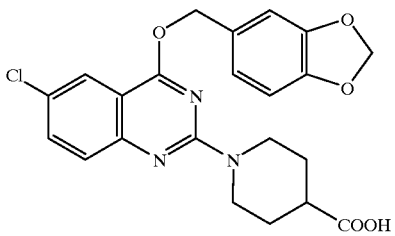

molecular formula; $C_{22}H_{20}ClN_3O_5$ yield (%); 84 m.p.(° C.); 145~147

Mass m/e; 442 (M+1)

NMR δ(DMSO-$d_6$);

1.47 (2H, m), 1.88 (2H, m), 2.49 (1H, m), 3.10 (2H, brt, J=13.2 Hz), 4.60 (2H, brd, J=13.2 Hz), 5.43 (2H, s), 6.01 (2H, s), 6.91 (1H, d, J=8.0 Hz), 7.02 (1H, d, J=8.0 Hz), 7.11 (1H, s), 7.39 (1H, d, J=8.8 Hz), 7.61 (1H, dd, J=8.8 Hz, 2.4 Hz), 7.77 (1H, d, J=2.4 Hz)

Example 67

2-(4-Carboxypiperidino)-4-(3,4-methylenedioxybenzyl)thio-6-chloroquinazoline

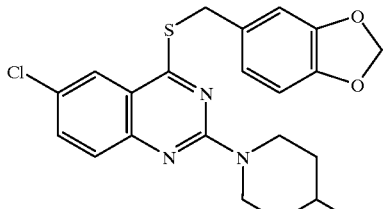

molecular formula; $C_{22}H_{20}ClN_3O_4S$ yield (%); 98 m.p.(° C.); 153~154

Mass m/e; 458 (M+1)

NMR δ(DMSO-$d_6$);

1.50 (2H, m), 1.82 (2H, m), 2.39 (1H, brs), 3.18 (2H, m), 4.48 (2H, s), 4.55 (2H, brs), 5.96 (2H, s), 6.82 (1H, d, J=8.0 Hz), 6.92 (1H, d, J=8.0 Hz), 6.99 (1H, s), 7.41 (1H, brd, J=8.8 Hz), 7.62 (1H, brd, J=8.8 Hz), 7.69 (1H, brs)

Example 68

2-(4-Nitroxypiperidino)-4-(3,4-methylenedioxybenzyl)amino-6-chloroquinazoline

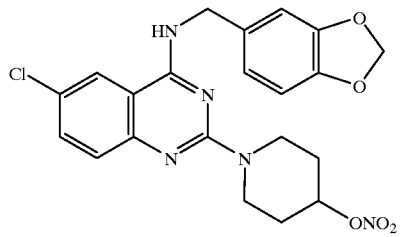

molecular formula; $C_{21}H_{20}ClN_5O_5$
yield (%); 11
m.p.(° C.); oily substance
Mass m/e; 458 (MH$^+$)
NMR δ(CDCl$_3$);
1.71~1.82(2H, m), 2.02~2.10(2H, m), 3.56~3.63(2H, m), 4.39~4.44(2H, m), 4.66(2H, d, J=5.2 Hz), 5.18~5.22(1H, m), 5.61(1H, brt, J=5.2 Hz), 5.96(2H, s), 6.79(1H, d, J=7.6 Hz), 6.84(1H, dd, J=7.6 Hz, 1.2 Hz), 6.87(1H, d, J=1.2 Hz), 7.39(1H, d, J=8.8 Hz), 7.43~7.47(2H, m)

Example 69

2-(4-Carboxypiperidino)-4-(3,4-methylenedioxybenzyl)amino-6-chloroquinoline

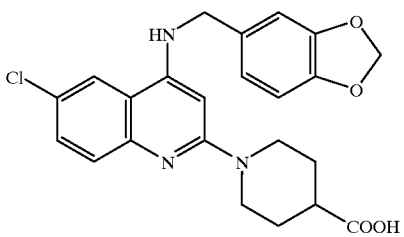

a) 2-(4-Ethoxycarbonylpiperidino)-4-(3,4-methylenedioxybenzyl)amino-6-chloroquinoline A reaction of a mixture comprising 130 mg of 2,6-dichloro-4-(3,4-methylenedioxybenzyl)aminoquinoline, 500 μl of ethyl isonipecotate and 1 ml of N-methyl-2-pyrrolidone was conducted on an oil bath at 150° C. for 3 hours. The reaction mixture was cooled, followed by the addition of water. The resulting mixture was extracted with ethyl acetate and the ethyl acetate layer was washed with water and a saturated aqueous solution of sodium chloride, dried over anhydrous magnesium sulfate and concentrated. The residue was purified by silica gel column chromatography with 20 to 50% ethyl acetate/hexane to give 150 mg of the title compound.

NMR δ(CDCl$_3$);
1.26(3H, t, J=7.1 Hz), 1.70~1.81(2H, m), 1.95~2.02(2H, m), 2.54(1H, tt, J=11.2 Hz, 3.8 Hz), 2.97~3.06(2H, m), 4.14(2H, q, J=7.1 Hz), 4.32~4.39(4H, m), 4.86(1H, t, J=5.5 Hz), 5.98(3H, s), 6.81(1H, d, J=7.7 Hz), 6.84~6.89(2H, m), 7.39(1H, dd, J=9.0 Hz, 2.4 Hz), 7.47(1H, d, J=2.4 Hz), 7.55(1H, d, J=9.0 Hz)

b) 2-(4-Carboxypiperidino)-4-(3,4-methylenedioxybenzyl)amino-6-chloroquinoline

A reaction of a mixture comprising 150 mg of the compound prepared in the step (a), 1 ml of a 1N aqueous solution of sodium hydroxide and 10 ml of ethanol was conducted on an oil bath at 60° C. for 2 hours. The reaction mixture was concentrated, followed by the addition of water. The resulting mixture was neutralized by the addition of 1 ml of 1N hydrochloric acid to precipitate crystals. The crystals were recovered by filtration, washed with water, and dried to give 130 mg of the title compound.

molecular formula; $C_{23}H_{22}ClN_3O_4$
yield (%); 92
m.p.(° C.); 235~237
Mass m/e; 440 (M+1)
NMR δ(DMSO-$_6$);
1.37~1.50(2h, m), 1.77~1.86(2H, m), 2.89~3.00(2H, br, 3 peak), 4.20~4.28(2H, br, 2 peak), 4.42(2H, d, J=5.7 Hz), 5.96(2H, s), 5.97(1H, s), 6.85(1H, d, J=7.9 Hz), 6.92(1H, dd, J=7.9 Hz, 1.5 Hz), 6.98(1H, d, J=1.5 Hz), 7.42(2H, brs), 7.58(1H, brs), 8.15(1H, brs)

Example 70

2-(4-Carboxypiperidino)-4-(3-chloro-4-methoxybenzyl)amino-6-chloroquinoline

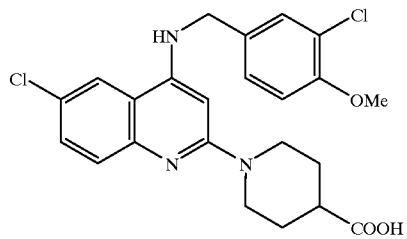

The title compound was prepared in a similar manner to that of Example 255.

molecular formula; $C_{23}H_{23}Cl_2N_3O_3$
m.p.(° C.); 282~283
Mass m/e; 460 (M+1)
NMR δ(DMSO-d$_6$);
1.36~1.48(2H, m), 1.76~1.84(2H, m), 2.43~2.53(1H, m), 2.91(2H, t, J=11.2 Hz), 4.26(2H, brd, J=13.2 Hz), 4.44(2H, d, J=5.9 Hz), 5.97(1H, s), 7.10(1H, d, J=8.6 Hz), 7.36(1H, dd, J=8.6 Hz, 2.2 Hz), 7.38(2H, s), 7.50(2H, brs and d, J=2.2 Hz), 8.11(1H, s)

Example 71

2-(3,4-Methylenedioxybenzylamino)-4-(4carboxypiperidino)-6-chloroquinoline

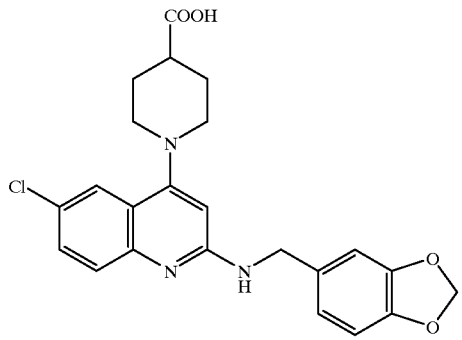

130 mg of the title compound was prepared from 140 mg of the 4,6-dichloro-2-(3,4-methylenedioxybenzyl)

aminoquinoline prepared in the step (b) of Example 253 as a by-product in a similar manner to that of Example 255.

molecular formula; $C_{23}H_{22}ClN_3O_4$
yield (%); 99
m.p.(° C.); 270~272
Mass m/e; 440 (M+1)
NMR δ(DMSO-$d_6$);
1.78~1.89(2H, m), 1.96~2.04(2H, m), 2.70~2.79(2H, m), 3.26~3.36(2H, m), 4.49(2H, d, J=5.7 Hz), 5.96(2H, s), 6.37(1H, s), 6.85(2H, s), 6.94(1H, s), 7.37(1H, t, J=5.7 Hz), 7.41(1H, dd, J=8.8 Hz, 2.4 Hz), 7.46(1H, d, J=8.8 Hz), 7.60(1H, d, J=2.4 Hz)

Example 72

2-(4-Carboxypiperidino)-4-(3-chloro-4-methoxybenzyl)amino-6-cyanoquinazoline

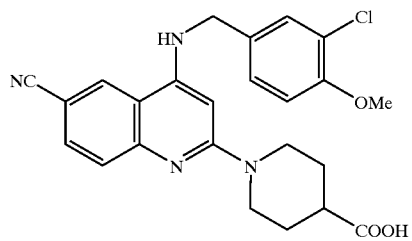

a) 2-(4-Ethoxycarbonylpiperidino)-4-(3-chloro-4methoxybenzylamino)-6-cyanoquinoline A mixture comprising 750 mg of 2-chloro-4-(3-chloro-4-methoxybenzyl)amino-6-cyanoquinoline, 1.6 ml of isonipecotic acid and 5 ml of N-methyl-2-pyrrolidone was heated on an oil bath at 130° C. for 3 hours and cooled, followed by the addition of water. The resulting mixture was extracted with ethyl acetate and the ethyl acetate layer was washed with water and a saturated aqueous solution of sodium chloride, dried over anhydrous magnesium sulfate, and concentrated. The residue was subjected to silica gel column chromatography (20 to 40% ethyl acetate/hexane) and thereafter recrystallized from ethyl acetate/hexane to give 860 mg of the title compound.

NMR δ($CDCl_3$);
1.26(3H, t, J=7.1 Hz), 1.68~1.79(2H, m), 1.95~2.03(2H, m), 2.58(1H, tt, J=11.0 Hz, 4.0 Hz), 3.03~3.12(2H, m), 3.92(3H, s), 4.15(2H, q, J=7.1 Hz), 4.36~4.43(4H, m), 5.08(1H, t, J=5.1 Hz), 5.94(1H, s), 6.95(1H, d, J=8.4 Hz), 7.26(1H, dd, J=8.4 Hz, 2.2 Hz), 7.42(1H, d, J=2.2 Hz), 7.55~7.61(2H, m), 7.88(1H, s)

b) 2-(4-Carboxypiperidino)-4-(3-chloro-4methoxybenzylamino)-6-cyanoquinoline

A mixture comprising 500 mg of the compound prepared in the step (a), 2 ml of a 1N aqueous solution of sodium hydroxide, 20 ml of tetrahydrofuran and 25 ml of ethanol was reacted at 50° C. for 2 hours, followed by the addition of 2 ml of 1N hydrochloric acid. About 20 ml of the solvents was distilled away to precipitate crystals. The crystals were recovered by filtration, washed with water and ethyl acetate, and dried to give 460 mg of the title compound.

molecular formula; $C_{24}H_{23}ClN_4O_3$
yield (%); 98
m.p.(° C.); 274~276(dec.)
NMR δ(DMSO-$d_6$);
1.35~1.47(2H, m), 1.78~1.87(2H, m), 2.47~2.56 (1H, m), 2.95~3.04(2H, m), 3.81(3H, s), 4.30~4.39(2H, m), 4.46(2H, d, J=5.7 Hz), 6.01(1H, s), 7.11(1H, d, J=8.6 Hz), 7.37(1H, dd, J=8.6 Hz, 2.2 Hz), 7.40(1H, d, J=8.8 Hz), 7.52(1H, d, J=2.2 Hz), 7.65(1H, dd, J=8.8 Hz, 1.6 Hz), 7.68(1H, t, J=5.7 Hz), 8.55(1H, d, J=1.6 Hz), 12.20(1H, brs)

Example 73

2-(4-Carboxypiperidino)-8-(3,4-methylenedioxybenzyl)aminopyrido[2,3-d]pyrimidine

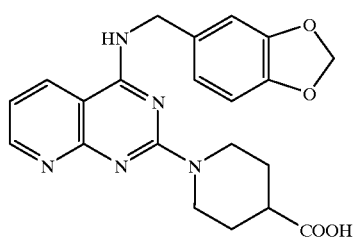

a) 2-(4-ethoxycarbonylpiperidino)-8-(3,4-methylenedioxybenzylamino)pyrido[2,3-d]pyrimidine 41 mg of triethylamine and 190 mg of ethyl isonipecotate were added to a solution of 127 mg of 2-chloro-8-(3,4-methylenedioxybenzyl)aminopyrido[2,3-d]pyrimidine in 8 ml of tetrahydrofuran. The obtained mixture was refluxed for 2 hours, followed by the addition of water. The resulting mixture was extracted with chloroform twice. The organic layers were combined, dried over magnesium sulfate, and distilled to remove the solvent. The residue was purified by silica gel chromatography (with ethyl acetate) to give 175 mg of the title compound (in a yield of 100%).

b) 2-(4-carboxypiperidino)-8-(3,4-methylenedioxybenzyl) aminopyrido[2,3-d]pyrimidine 1.56 ml of 1N sodium hydroxide was added to a solution of 170 mg of 2-(4-ethoxycarbonylpiperidino)-8(3,4-methylenedioxybenzyl)aminopyrido[2,3-d]pyrimidine in 10 ml of ethanol. The obtained mixture was stirred at room temperature for 6 hours and neutralized by the addition of 1N hydrochloric acid and water. The crystals thus precipitated were recovered by filtration, whereby 121 mg of the title compound was obtained.

molecular formula; $C_{21}H_{21}N_5O_4$
yield (%); 76
m.p.(° C.); 255~256
Mass m/e; 408 (M+1)
NMR δ(DMSO-$d_6$);
1.39 (2H, m), 1.80(2H, m), 2.51(1H, m), 3.01(2H, brt, J=11.2 Hz), 4.56(2H, d, J=5.6 Hz), 4.61(2H, brd, J=12.8 Hz), 5.94(2H, s), 6.82(1H, d, J=8.0 Hz), 6.84(1H, d, J=8.0 Hz), 6.93(1H, s), 7.03(1H, dd, J=8.0 Hz, 4.4 Hz), 8.38(1H, dd, J=8.0 Hz, 1.6 Hz), 8.61(1H, dd, J=4.4 Hz, 1.6 Hz), 8.70(1H, t, J=5.6 Hz), 12.16(1H, brs)

Examples 74 to 82

The following compounds were prepared in a similar manner to those of Examples 88 to 94.

Example 74

2-(4-Carboxypiperidino)-4-(3,5-dichloro-4-methoxybenzylamino)-6-cyanoquinazoline

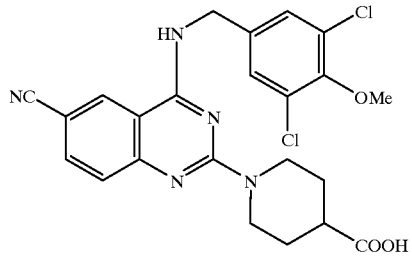

molecular formula; $C_{23}H_{21}Cl_2N_5O_3$ yield (%); 98 m.p.(° C.); 255~256(dec.)

Mass m/e; 486 (M+1)$^+$

NMR δ(DMSO-d$_6$);

1.36(2H, brm), 1.80(2H, brm), 2.52(1H, m), 3.03 (2H, m), 3.78(3H, s), 4.59(2H, d, J=6.0 Hz), 4.59-(2H, brm), 7.29(1H, d, J=8.8 Hz), 7.50(2H, s), 7.75(1H, dd, J=8.8 Hz, 1.6 Hz), 8.53(1H, d, J=1.6 Hz), 8.85(1H, brt, J=6.0 Hz), 12.18(1H, brs)

Example 75

2-[N-[2-(2-Pyridyl)ethyl]methylamino]-4-(3,4-methylenedioxybenzyl)]amino-6-chloroquinazoline dihydrochloride

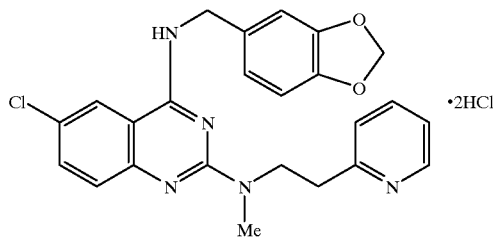

molecular formula; $C_{24}H_{22}ClN_5O_2 \cdot 2HCl$ yield (%); 94 m.p.(° C.); 234~236 (dec.)

Mass m/e; 448 (M+1)$^+$

NMR δ(DMSO-d$_6$);

3.2~3.3(5H, br), 4.12(2H, br), 4.61(2H, br), 5.97(2H, s), 6.82(1H, brd), 6.88(1H, brd), 7.00(1H, s), 7.74(2H, br), 7.86(1H, dd, J=9.2 Hz, 2.0 Hz), 8.01(1H, br), 8.26(1H, br), 8.57(1H, d, J=2.0 Hz), 8.74(1H, br), 10.16(1H, brs), 12.12 (1H, brs)

Example 76

2-(4-Carboxypiperidino)-4-(3,4-dihydroxybenzyl)amino-6-chloroquinazoline

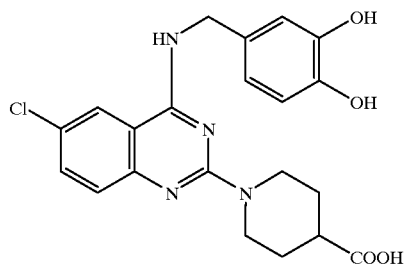

molecular formula; $C_{21}H_{21}ClN_4O_4$ yield (%); 95 m.p.(° C.); 216~218 (dec.)

Mass m/e; 429 (MH$^+$)

NMR δ(DMSO-d$_6$);

1.38~1.47(2H, m), 1.80~1.84(2H, m), 2.44~2.49(1H, m), 2.93~3.00(2H, m), 4.48(2H, d, J=5.6 Hz), 4.57~4.61(2H, m), 6.60~6.65(2H, m), 6.74(1H, d, J=1.6 Hz), 7.24(1H, d, J=8.8 Hz), 7.46(1H, dd, J=8.8 Hz, 2.0 Hz), 8.15(1H, d, J=2.0 Hz), 8.48(1H, brs), 8.675(1H, s), 8.75(1H, s), 12.14(1H, brs)

Example 77

2-(4-Carboxypiperidino)-4-(5-nitroxypentyl)amino-6-chloroquinazoline

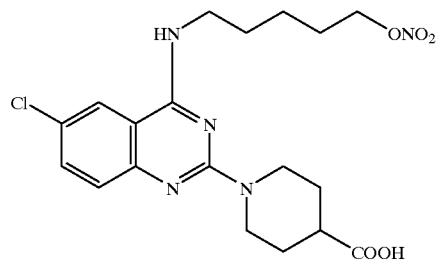

molecular formula; $C_{19}H_{24}ClN_5O_5$ yield (%); 80 m.p.(° C.); 176~179 (dec.)

Mass m/e; 438 (MH$^+$)

NMR δ(DMSO-d$_6$);

1.34~2.00(10H, m), 2.57~2.64(1H, m), 3.18~3.59(4H, m), 4.44~4.58(4H, m), 7.72~7.86(2H, m), 8.39~8.41(1H, m), 12.31(2H, brs)

Example 78

2-(Carboxymethyl)methylamino-4-(3-pyridylmethyl)amino-6-chloroquinazoline

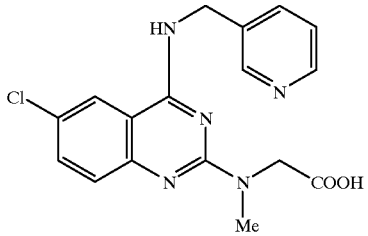

molecular formula; $C_{17}H_{16}ClN_5O_2$ yield (%); 97 m.p.(° C.); 222~223

Mass m/e; 358 (M+1)

NMR δ(DMSO-$d_6$);

3.10(3H, s), 4.22(2H, brs), 4.63(2H, brs), 7.31(2H, m), 7.48(1H, m), 7.72(1H, m), 8.14(1H, d, J=2.4 Hz), 8.43(1H, d, J=4.8 Hz), 8.59(1H, m), 8.66(1H, brs)

Example 79

2-[N-(3-Carboxypropyl)-N-methylamino]-4-(3-pyridylmethyl)amino-6-chloroquinazoline

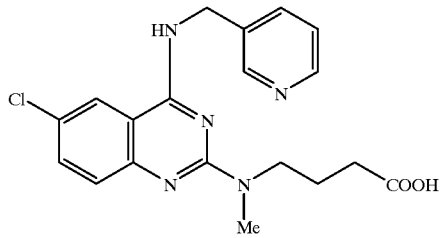

molecular formula; $C_{19}H_{20}ClN_5O_2$ yield (%); 41 m.p.(° C.); 110~112

Mass m/e; 386 (M+1)

NMR δ(DMSO-$d_6$);

1.67(2H, brs), 2.09(2H, m), 3.02(3H, s), 3.53(2H, t, J=6.8 Hz), 4.67(2H, d, J=5.6 Hz), 7.24(2H, d, J=8.8 Hz), 7.31(1H, dd, J=8.0 Hz, 4.8 Hz), 7.47(1H, dd, J=8.8 Hz, 2.0 Hz), 7.73(1H, d, J=8.0 Hz), 8.13(1H, d, J=2.0 Hz), 8.41(1H, d, J=4.8 Hz), 8.58(1H, s), 8.62(1H, brs), 12.04(1H, brs)

Example 80

2-(4-Carboxypiperidino)-4-(2-pyridylmethyl)amino-6-chloroquinazoline

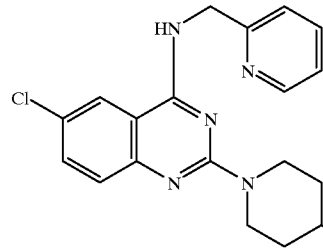

molecular formula; $C_{20}H_{20}ClN_5O_2$ yield (%); 92 m.p.(° C.); 235~237

Mass m/e; 398 (M+1)

NMR δ(DMSO-$d_6$);

1.25~1.45(2H, m), 1.71~1.83(2H, m), 2.45~2.54(1H, m), 2.93~3.10(2H, m), 4.37~4.48(2H, m), 4.77(2H, d, J=5.5 Hz), 7.25(1H, dd, J=7.7 Hz, 5.0 Hz), 7.37(1H, d, J=7.7 Hz), 7.48(1H, brs), 7.63(1H, brs), 7.73(1H, td, J=7.7 Hz, 1.6 Hz), 8.34(1H, brs), 8.51(1H, brd, J=5.0 Hz), 12.23(1H, brs)

Example 81

2-(4-Carboxypiperidino)-4-(3-pyridylmethyl)amino-6-chloroquinazoline

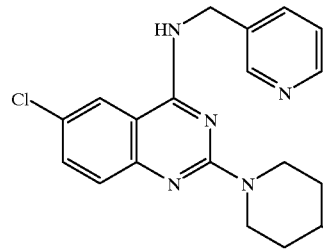

molecular formula; $C_{20}H_{20}ClN_5O_2$ yield (%); 93 m.p.(° C.); >250

Mass m/e; 398 (M+1)

NMR δ(DMSO-$d_6$);

1.45~1.60(2H, m), 1.84~1.97(2H, m), 2.58~2.68(1H, m), 3.25~3.45(2H, m), 4.45~4.54(2H, m), 4.80(2H, d, J=5.7 Hz), 7.41(1H, dd, J=7.9 Hz, 4.8 Hz), 7.82(1H, dd, J=9.0 Hz, 2.0 Hz), 7.86~7.96(2H, m), 8.50(1H, d, J=4.8 Hz), 8.55(1H, d, J=1.6 Hz), 8.69(1H, s)

Example 82

2-(4-Carboxypiperidino)-4-(4-pyridylmethyl)amino-6-chloroquinazoline

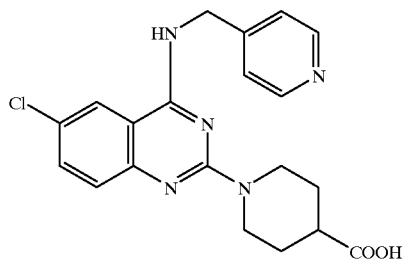

molecular formula; $C_{20}H_{20}ClN_5O_2$
yield (%); 89
m.p.(° C.); 167~168
Mass m/e; 398 (M+1)
NMR δ(DMSO-$d_6$);
1.24~1.36(2H, m), 1.68~1.77(2H, m), 2.40~2.49(1H, m), 2.86~2.96(2H, m), 4.42~4.50(2H, m), 4.66(2H, d, J=5.7 Hz), 7.28(1H, d, J=9.0 Hz), 7.34(2H, d, J=6.0 Hz), 7.51(1H, dd, J=9.0 Hz, 2.4 Hz), 8.18(1H, d, J=2.4 Hz), 8.47(2H, d, J=6.0 Hz), 8.74(1H, t, J=5.7 Hz)

Example 83

2-(4-Cyanopiperidino)-4-(3,4-methylenedioxybenzyl)amino-6-chloroquinazoline

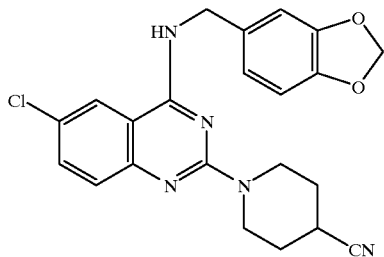

75 ml of thionyl chloride and 150 ml of acetonitrile were added to 3.8 g (0.0086 mol) of 2-(4-carbamoylpiperidino)-4-(3,4-methylenedioxybenzyl)amino-6-chloroquinazoline. The mixture thus obtained was heated under reflux for one hour. The reaction mixture was distilled under a reduced pressure to remove the solvent. A saturated aqueous solution of sodium hydrogencarbonate and triethylamine were added to the residue and the resultant mixture was extracted with ethyl acetate. The organic layer was washed with a saturated aqueous solution of sodium chloride, dried over anhydrous magnesium sulfate, filtered and distilled under a reduced pressure to remove the solvent. The obtained residue was purified by a silica gel column chromatography (ethyl acetate-n-hexane) and recrystallized from chloroform-n-hexane to give 3.1 g of the title compound.

molecular formula; $C_{22}H_{20}ClN_5O_2$
yield (%); 85
m.p.(° C.); 169~170
NMR δ(CDCl$_3$);
1.88 (2H, m), 1.95 (2H, m), 2.87 (1H, m), 3.73 (2H, m), 4.25 (2H, m), 4.67 (2H, d, J=5.6 Hz), 5.65 (1H, t, J=5.6 Hz), 5.97 (2H, s), 6.79 (1H, d, J=8.0 Hz), 6.84 (1H, dd, J=8.0 Hz, 1.6 Hz), 6.87 (1H, d, J=1.6 Hz), 7.39 (1H, d, J=8.8 Hz), 7.44 (1H, d, J=2.4 Hz), 7.46 (1H, dd, J=8.8 Hz, 2.4 Hz)

Example 84

2-[4-(1H-tetrazol-5-yl)piperidinol-4-(3,4-methylenedioxybenzyl)amino-6-chloroquinazoline hydrochloride

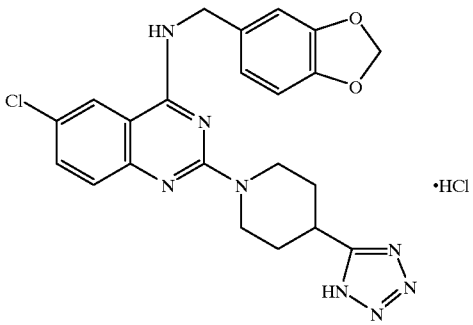

10 ml of toluene was added to a mixture comprising 0.50 g (0.0012 mol) of 2-(4-cyanopiperidino)-4-(3,4-methylenedioxybenzyl)amino-6-chloroquinazoline and 0.50 g (0.0024 mol) of trimethyl stannylazide. The mixture thus obtained was heated under reflux for two days. The reaction mixture was distilled under a reduced pressure to remove the solvent. The residue was suspended in 10 ml of ethanol, followed by the addition of 10 ml of 1N hydrochloric acid. The mixture thus obtained was stirred at room temperature for several hours. The mixture was filtered to recover the crystal. The crystal was washed with water and air-dried to give 0.60 g of the title compound.

molecular formula; $C_{22}H_{21}ClN_8O_2 \cdot HCl$
yield (%); quantitative
m.p.(° C.); 212~214
Mass m/e; 465 (M+1)$^+$
NMR δ(DMSO-$d_6$);
1.80 (2H, m), 2.17 (2H, m), 3.45 (2H, m), 4.62 (2H, m), 4.69 (2H, d, J=5.6 Hz), 5.97 (2H, s), 6.86 (1H, d, J=7.6 Hz), 6.91 (1H, dd, J=7.6 Hz, 1.6 Hz), 7.01 (1H, d, J=1.6 Hz), 7.84 (1H, dd, J=8.8 Hz, 1.6 Hz), 7.88 (1H, d, J=8.8 Hz), 8.51 (1H, d, J=1.6 Hz), 10.13 (1H, brs), 12.28 (1H, brs)

Example 85

4-Amino-6,7-dimethoxy-2-[4-(5-ethoxycarbonylamino-1,2,3-thiadiazole-4-carbonyl)-piperazin-1-yl]-quinazoline Hydrochloride A solution of 5-ethoxycarbonylamino-1,2,3-thiadiazole-4-carbonyl chloride (5.17 g, 0.022 mole) in dioxane (35 ml. was added to a solution of 4-amino-6,7-dimethoxy-2-(1-piperazinyl)quinazoline (6.35 g., 0.022 mole) in diexane (190 ml.). The resultant mixture was stirred at reflux for 1 hour, and then at 23° C. for 18 hours. Filtration gave the title compound; m.p. 281°–284° C. (dec.) after crystallization from methanol.

Anal. Calcd. for $C_{20}H_{24}N_8O_5 \cdot HCl$: C, 45.76; H, 4.80; Cl, 6.75; N, 21.35. Found: C, 45.49; H, 4.65; Cl., 7.10; N, 21.06.

The 5-ethoxycarbonylamino-1,2,3-thiadiazole-4-carbonyl chloride starting material was obtained in the following manner.

A. 5-Ethoxycarbonylamino-1,2,3-thiadiazole-4-carboxylic Acid

A suspension of sodium thiocyanate (24.30 g, 0.30 mole) in acetonitrile (120 ml), maintained at 19° C., was treated dropwise over 22 minutes with a solution of ethyl chloroformate (28.7 ml, 0.30 mole) in acetonitrile (25 ml). The resultant mixture was stirred for 25 minutes at 20° C. and then ethyl diazoacetate (31.5 ml, 0.30 mole) was added. After stirring for 24 hours, 6.0 N hydrochloric acid (300 ml) was added with cooling Acetonitrile solvent was removed in vacuo and the residual aqueous suspension was extracted several times with ether. Combined ether extracts were washed with water, dried ($Na_2SO_4$) and evaporated to leave 51.0 g of ethyl 5-ethoxycarbonylamino-1,2,3-thiadiazole-4-carboxylate. This ester was hydrolyzed by refluxing for 6 hours in a mixture of ethanol (80 ml) and aqueous 6 N hydrochloric acid (400 ml) to yield the title acid; m.p. 179°–180° dec. after crystallization from nitromethane.

B. 5-Ethoxycarbonylamino-1,2,3-thiadiazole-4-carbonyl Chloride

Oxalyl chloride (8.76 g, 0.069 mole) was added slowly to a stirred suspension of 5-ethoxycarbonylamino-1,2,3-thiadiazole-4-carboxylic acid (5.00 g, 0.023 mole) in dry ether (65 ml) containing three drops of N,N-dimethylformamide. Tetrahydrofuran was added and the resultant clear solution was stirred at 23° C. for 2 hours. Filtration and subsequent evaporation gave a residue which was triturated under petroleum ether to yield the title acid chloride (5.17 g, 96%) m.p. 129°–133.5° C.

Example 86

4-Amino-6,7-dimethoxy-2-[4-(1,2,3-thiadiazole-4carbonyl)piperazin-1-yl)quinazoline Hydrochloride The title compound was prepared by reacting 1,2,3-thiadiazole-4-carbonyl chloride (D. L. Pain and R. Slack, J. Chem. Soc., 5166 (1965)) and 4-amino-6,7-dimethoxy-2-(1-piperazinyl)quinazoline according to the procedure of Example 1. After crystallization from aqueous ethanol, the title compound melted at 270° C. (dec.).

Anal. Calcd for $C_{17}H_{19}N_7O_3S \cdot HCl$: C, 46.62; H, 4.60; N, 22.39; S, 7.32. Found: C, 46.43; H, 4.39; N, 22.58; S, 7.14 (corrected for 6.08% water of hydration).

Example 87

4-Amino-6,7-dimethoxy-2-[4-(1,2,3-thiadiazole-5-carbonyl)piperazin-1-yl)quinazoline Hydrochloride A solution of potassium hydroxide (3.30 g.) in water (7 ml.) was added to a solution of ethyl 1,2,3-thiadiazole-5-carboxylate (8.00 g.) in ethanol (25 ml.). The mixture was stirred at 23° C. for 2 hours, and then was worked up to yield potassium 1,2,3-thiadiazole-5-carboxylate. A suspension of this salt (3.00 g.) in toluene (25 ml.) was treated at 0° C. with oxalyl chloride (1.6 ml.), stirred at 0° C. for 1 hour, and then was worked up to yield 1,2,3-thiadiazole-5-carbonyl chloride.

Reaction of a 1,2,3-thiadiazole-5-carbonyl chloride and 4-amino-6,7-dimethoxy-2-(1-piperazinyl)quinazoline according to the procedure of Example 1 provided the title compound having a melting point of 295°–297° C. after crystallization from aqueous ethanol.

Anal. Calcd. for $C_{17}H_{19}N_7O_3S \cdot HCl$: C, 46.62; H, 4.60; N, 22.39; S, 7.32. Found: C, 46.91, H, 4.51; N, 21.91; S, 7.39 (corrected for 2.6% water of hydration).

Example 88

4-Amino-6,7-dimethoxy-2-[4-(5-methyl-1,2,3-thiadiazole-4-carbonyl)-piperazin-1-yl)quinazoline Hydrochloride Hydrolysis of ethyl 5-methyl-1,2,3-thiadiazole-4-carboxylate (D. L. Pain and R. Sleck, J. Chem. Soc., 5166 (1965)) and subsequent treatment of the acid with oxalyl chloride according to the method of Example 3 provides 5-methyl-1,2,3-thiadiazole-4-carbonyl chloride.

Reaction of the carbonyl chloride and 4-amino-6,7-dimethoxy-2-(1-piperizinyl)-quinazoline according to the procedure of Example 1 provides the title compound.

Example 89

4-Amino-6,7-dimethoxy-2-[4-(5-methylthio-1,3,4-oxadiazole-2-carbonyl)-piperazin-1-yl-quinazoline hydrochloride A solution of 5-methylthio-1,3,4-oxadiazole-2-carbonyl chloride (0.601 g., 3.36 mole) in dioxane (10 ml) was added to a solution of 4-amino-6,7-dimethoxy-2-(1-piperizinyl)quinazoline (0.972 g., 3.36 mmole) in dioxane (100 ml.). The resultant mixture was stirred at room temperature for 65 hours, then was heated at reflux for 30 minutes. Filtration gave the title compound (1.56 g.). Recrystallization from methanol gave a product having a M.P. of 280°–285° C. with decomposition.

Anal. Calcd for $C_{18}H_{21}N_7O_4S \cdot HCl$: C, 46.20; H, 4.74; Cl, 7.58; N, 20.96; S, 6.85. Found: C, 46.34; H, 4.89; Cl, 7.59; N, 20.38; S, 6.58.

Example 90

4-Amino-6,7-dimethoxy-2-[4-(5-ethylthio-1,3,4-oxadiazole-2-carbonyl)-piperazin-1-yl-quinazoline hydrochloride The title compound was prepared from 5-ethylthio-1,3,4-oxadiazole-2-carbonyl chloride (0.79 g., 4.1 mmole) and 4-amino-6,7-dimethoxy-2-(1-piperazinyl)-quinazoline (1.19 g., 4.1 mmole) following the procedure described in Example 1. The product had a M.P. of 246°–248.5° C.

Anal. Calcd for $C_{19}H_{13}N_7O_4S \cdot HCl$: C, 47.34; H, 5.02; N, 20.34; S, 6.65. Found: C, 47.37; H, 4.76; N, 20.15; S, 6.71 (corrected for 4.11% $H_2O$).

Example 91

4-Amino-6,7-dimethoxy-2-[4-(5-isopropylthio-1,3,4-oxadiazole-2-carbonyl)-piperazin-1-yl]-quinazoline hydrochloride The title compound was prepared from 5-isopropylthio-1,3,4-oxadiazole-2-carbonyl chloride (1.54 g., 7.5 mmole) and 4-amino-6,7-dimethoxy-2-(1-piperazinyl)quinazoline (2.1 g., 7.5 mmole) following the procedure of Example 1. The product had a M.P. of 260°–263° C. with decomposition.

Anal. Calcd for $C\_H_{23}N_7O_4S \cdot HCl$: C, 48.43; H, 5.28; N, 19.77. Found: C, 48.05; H, 5.20; N, 19.61.

Example 92

4-Amino-6,7-dimethoxy-2-[4-(5-n-propylthio-1,3,4-oxadiazole-2-carbonyl)-piperazin-1-yl]-quinazoline hydrochloride The title compound was prepared from 5-n-propylthio-1,3,4-oxadiazole-2-carbonyl chloride (1.68 g., 8.16 mmole) and 4-amino-6,7-dimethoxy-2-(1-piperazinyl)quinazoline (2.36 g., 8.16 mmole) following the procedure of Example 1. The product had a M.P. of 230°–245° C. with decomposition.

Anal. Calcd for $C_2H\_N_7O_4S \cdot HCl$: C, 48.43; H, 5.25; N, 19.77. Found: C, 48.11; H, 5.35; N, 19.65.

Example 93

4-Amino-6,7-dimethoxy-2-[4-(5-n-butylthio-1,3,4-oxadiazole-2-carbonyl)-piperazin-1-yl]-quinazoline hydrochloride The title compound was prepared from 5-n-butylthio-1,3,4-oxadiazole-2-carbonyl chloride and 4-amino-6,7-dimethoxy-2-(1-piperazinyl)quinazoline following the procedure of Example 89.

Example 94

4-Amino-6,7-dimethoxy-2-[4-(isoxazole-5-carbonyl)-piperazine-1-yl]quinazoline Hydrochloride A solution of isoxazole-5-carbonyl chloride (1.33 g., 0.01 mole) in dioxane was added to a solution at 30° C. of 4-amino-6,7-dimethoxy-2-(1-piperazinyl)quinazoline (2.94 g., 0.01 mole) in dioxane. The mixture was stirred at reflux for three minutes, then at room temperature for 16 hours. Filtration gave the title compound (4.02 g., 94% yield). Recrystallization from aqueous methanol gave a product having a m.p. of 270° C. with decomposition.

Anal. Calcd. for $C_{18}H_{20}N_6O_4S \cdot HCl$: C, 51.37; H, 5.03; Cl, 8.42; N, 19.97. Found: C, 50.86; H, 4.65; Cl, 8.52; N, 19.81 (corrected for 4.30% $H_2O$).

Example 95

4-Amino-6,7-dimethoxy-2-[4-(isoxazole-3-carbonyl)-piperazin-1-yl]quinazoline Hydrochloride A solution of isoxazole-3-carbonyl chloride (0.753 g., 0.0057 mole) in dioxane (20 ml.) was added to a solution of 4-amino-6,7-dimethoxy-2-(1-piperazinyl)quinazoline (1.66 g., 0.0057 mole) in dioxane (60 ml.). The mixture was stirred at reflux for 30 minutes, then at room temperature for 64 hours. Filtration gave the title compound which was recrystallized from methanol (1.81 g., 75% yield). The product had a m.p. of 268°–273° C. with decomposition.

Anal. Calcd. for $C_{18}H_{20}H_6O_4HCl$: C, 51.37; H, 5.03; Cl, 8.42; N, 19.97. Found: C, 50.04; H, 4.86; Cl, 8.66; N, 19.57 (corrected for 3.11% $H_2O$).

Example 96

4-Amino-6,7-dimethoxy-2-[4-(isoxazole-4-carbonyl)-piperazin-1-yl]quinazoline Hydrochloride A solution of isoxazole-4-carbonyl chloride (1.06 g., 8.08 mmole) in dioxane (8 ml.) was added to a solution at of 4-amino-6,7-dimethoxy-2-(1-piperazinyl)quinazoline (2.34 g., 8.08 mmole) in dioxane (200 ml.). The mixture was stirred at room temperature for 20 hours. Filtration gave the title compound, which, after recrystallization from methanol, had a m.p. of 225°–260° C. with decomposition.

Anal. Calcd. for $C_{18}H_{20}N_6O_4HCl$: C, 51.37; H, 5.03; Cl, 8.42; N, 19.97. Found: C, 51.37; H, 4.95; Cl, 8.34; N, 19.95 (corrected for 1.63% $H_2O$).

Example 97

4-Amino-6,7-dimethoxy-2-[4-(5-methylisoxazole-3-carbonyl)-piperazin-1-yl]quinazoline Hydrochloride A solution of 5-methylisoxazole-3-carbonyl chloride (0.41 g., 2.83 mmole) in dioxane was added to a solution of 4-amino-6,7-dimethoxy-2-(1-piperazinyl)quinazoline (0.82 g., 2.83 mmole) in dioxane. The mixture was treated as described in the previous example to give the title compound having a m.p. of 271°–273° C. with decomposition.

Anal. Calcd. for $C_{19}H_{22}N_6O_4HCl \ H_2O$: C, 50.38; H, 5.56; N, 18.56; $H_2O$, 3.92. Found: C, 50.58; H, 5.40; N, 18.86; $H_2O$, 3.72.

Example 98

4-Amino-6,7-dimethoxy-2-[4-(3-methylisoxazole-4-carbonyl)-piperazin-1-yl]quinazoline Hydrochloride A solution of 3-methylisoxazole-4-carbonyl chloride (1.01 g., 6.9 mmole) in dioxane and 4-amino-6,7-dimethoxy-2-(1-piperazinyl)quinazoline (2.00 g., 6.9 mmole) in dioxane was stirred under reflux for 15 hours, then worked up as described in Example 1. The title compound after recrystallization from methanol had a m.p. of 300°–301° C. with decomposition.

Anal. Calcd. for $C_{19}H_{22}N_6O_4HCl$: C, 52.47; H, 5.33; N, 19.33. Found: C, 52.62; H, 5.31; N, 19.12 (corrected for 1.13% $H_2O$).

Example 99

4-Amino-6,7-dimethoxy-2-[4-(3-methylisoxazole-5-carbonyl)-piperazin-1-yl]quinazoline Hydrochloride A solution of 3-methylisoxazole-5-carbonyl chloride (0.73 g., 5.02 mmole) in dioxane was added to a solution of 4-amino-6,7-dimethoxy-2-(1-piperazinyl)quinazoline (1.45 g., 5.02 mmole) in dioxane. The mixture was heated briefly, then was stirred at 20° C. for 2.5 hours. Workup as in Example 1 gave the title compound having a m.p. of 263°–264° C. with decomposition.

Anal. Calcd. for $C_{19}H_{22}N_6O_4HCl$: C, 52.47; H, 5.33; Cl, 8.15; N, 19.33. Found: C, 51.82; H, 5.04; Cl, 8.36; N, 19.46 (corrected for 4.82% $H_2O$).

Example 100

4-Amino-6,7-dimethoxy-2-[4-(oxazole-4-carbonyl)-piperazin-1-yl]quinazoline Hydrochloride A solution of oxazole-4-carbonyl chloride (0.73 g., 5.53 mmole) in dioxane was added to a solution of 4-amino-6,7-dimethoxy-2-(1-piperazinyl)quinazoline (1.60 g., 5.53 mmole) in dioxane. The mixture was heated at reflux for 0.5 hour, then was stirred at 20° C. for 64 hours. Filtration gave the title compound having a m.p. of 291°–294° C. with decomposition after recrystallization from aqueous ethanol.

Anal. Calcd. for $C_{18}H_{20}N_6O_4HCl \ H_2O$: C, 49.26; H, 5.28; Cl, 8.08; N, 19.15. Found: C, 48.92; H, 4.83; Cl, 8.33; N, 18.94.

Example 101

4-Amino-6,7-dimethoxy-2-[4-(2-methyloxazole-4-carbonyl)-piperazin-1-yl]quinazoline Hydrochloride A solution of 2-methyloxazole-4-carbonyl chloride (1.01 g., 6.9 mmole) in dioxane was added to a solution of 4-amino-6,7-dimethoxy-2-(1-piperazinyl)quinazoline (2.00 g., 6.9 mmole) in dioxane. The mixture was heated at reflux for 2 hours. Filtration gave the title compound having a m.p. of 278°–280° C. with decomposition after recrystallization from methanol.

Anal. Calcd. for $C_{19}H_{22}N_6O_4HCl$: C, 52.47; H, 5.33; N, 19.33. Found: C, 52.08; H, 5.43; N, 18.89 (corrected for moisture).

Example 102

4-Amino-6,7-dimethoxy-2-[4-(4-methyloxazole-5-carbonyl)-piperazin-1-yl]quinazoline Hydrochloride The title compound was prepared from 4-methyloxazole-5-carbonyl chloride (0.85 g.) and 4-amino-6,7-dimethoxy-2-(1-piperazinyl)quinazoline (1.68 g.) following the procedure of Example 1. The product had a m.p. of 283.5°–288° C. with decomposition.

Anal. Calcd. for $C_{19}H_{22}N_6O_4HCl$: C, 52.48; H, 5.33; Cl, 8.15; N, 19.33. Found: C, 52.19; H, 4.94; Cl, 8.13; N. 19.05 (corrected for 1.59% $H_2O$).

Example 103

4-Amino-6,7-dimethoxy-2-[4-(isothiazole-4-carbonyl)-piperazin-1-yl]quinazoline Hydrochloride The title compound was prepared from isothiazole-4-carbonyl chloride (1.01 g.) and 4-amino-6,7-dimethoxy-2-(1-piperazinyl)quinazoline (1.99 g.) following previously described procedures. The product had a m.p. of 286°–287° C. with decomposition.

Anal. Calcd for $C_{18}H_{20}N_6O_3S$ HCl: C, 49.48; H, 4.84; Cl, 8.11; N. 19.23; S, 7.34. Found: C, 49.29; H, 4.81; Cl, 8.19; N, 19.27; S, 7.23 (corrected for 0.93% $H_2O$).

Example 104

4-Amino-6,7-dimethoxy-2-[4-(thiazole-2-carbonyl)-piperazin-1-yl]quinazoline Hydrochloride The title compound was prepared from thiazole-2-carbonyl chloride (0.79 g.) and 4-amino-6,7-dimethoxy-2-(1-piperazinyl)quinazoline (1.54 g.) following previously described procedures. The product had a m.p. of 273°–276° C. with decomposition.

Anal. Calcd. for $C_{18}H_{20}N_6O_3S$ HCl: C, 49.48; H, 4.84; N. 19.23. Found: C, 48.68; H, 4.62; N, 18.87 (corrected for 4.19% $H_2O$).

Example 105

4-Amino-6,7-dimethoxy-2-[4-(thiazole-4-carbonyl)-piperazin-1-yl]quinazoline Hydrochloride The title compound was prepared from thiazole-4-carbonyl chloride (1.02 g.) and 4-amino-6,7-dimethoxy-2-(1-piperazinyl)quinazoline (2.00 g.) following previously described procedures. The product had a m.p. of 274°–277° C. with decomposition.

Anal. Calcd. for $C_{18}H_{20}N_6O_3S$ HCl: C, 49.48; H, 4.48; N, 19.24. Found: C, 49.11; H, 4.69; N, 19.31 (corrected for 4.47% $H_2O$).

Example 106

4-Amino-6,7-dimethoxy-2-[4-(2-methylthiazole-4-carbonyl)-piperazin-1-yl]quinazoline Hydrochloride The title compound was prepared from 2-methylthiazole-4-carbonyl chloride (0.49 g.) and 4-amino-6,7-dimethoxy-2-(1-piperazinyl)quinazoline (0.87 g.) following previously described procedures. The product had a m.p. of 260°–263° C. with decomposition.

Anal. Calcd. for $C_{19}H_{22}N_6O_3S$ HCl: C, 50.60; H, 5.14; N, 18.64. Found: C, 50.88; H, 4.96; N, 18.67 (corrected for 2.88% $H_2O$).

Example 107

4-Amino-6,7-dimethoxy-2-[4-(thiazole-5-carbonyl)-piperazin-1-yl]quinazoline Hydrochloride The title compound was prepared from thiazole-5-carbonyl chloride (0.77 g.) and 4-amino-6,7dimethoxy-2-(1-piperazinyl)quinazoline (1.51 g.) following previously described procedures. The product had a m.p. of 280°–281° C. with decomposition.

Anal. Calcd. for $C_{18}H_{20}N_6O_3S$ HCl: C, 49.48; H. 4.84; Cl, 8.11; N, 19.23; S, 7.34. Found: C, 49.22; H, 5.19; Cl, 8.31; N, 19.49; S, 6.79 (corrected for 2.63% $H_2O$).

Example 108

4-Amino-6,7-dimethyoxy-2-[4-(2-methylthiazole-5-carbonyl)-piperazin-1-yl]quinazoline Hydrochloride The title compound was prepared from 2-methylthiazole-5-carbonyl chloride (0.42 g.) and 4-amino-6,7-dimethyoxy-2-(1-piperazinyl)-quinazoline (0.75 g.) following previously described procedures. The product had a m.p. of 294°–297° C. with decomposition.

Anal. Calcd. for $C_{19}H_{22}N_6O_3S$ HCl: C, 50.60; H, 5.14; N, 18.64. Found: C, 50.60; H. 4.95; N. 18.50 (corrected for 1.96% $H_2O$).

Example 109

4-Amino-6,7-dimethoxy-2-[4-(4-methylthiazole-5-carbonyl)-piperazin-1-yl]quinazoline Hydrochloride The title compound was prepared from 4-methylthiazole-5-carbonyl chloride (1.1 g.) and 4-amino-6,7-dimethyoxy-2-(1-piperazinyl)quinazoline (2.0 g.) following previously described procedures. The product had a m.p. of 293°–295° C. with decomposition.

Example 110

Synthesis of 2-[$N^4$-(2-furoyl)-homopiperazino]-4-amino-6,7-dimethoxy-quinazoline a. Synthesis of 2-homopiperazino-4-amino-6,7-dimethoxy-quinazoline 17 Grams of 2-chloro-4-amino-6,7-dimethoxy-quinazoline and 18.2 g of N-formylhomopiperazine are added to 170 ml of butanol and the whole is refluxed with stirring for three hours. After completion of the reaction, the mixture is cooled, and the crystals thus precipitated are filtered out, washed with a small quantity of ethanol and air-dried. 25 Grams of crude crystal are obtained. 13 Grams of the crystal thus obtained are taken and added with 80 ml of 9% hydrochloric acid. The mixture is refluxed under stirring for 60 minutes. After completion of the reaction, the mixture is allowed to cool. The crystal thus precipitated are filtered out and then recrystallized from a mixture of methanol and ethanol.

Yield: 10.7 g (80.4%)

Melting point: 246–247° C.

Elementary analysis (as $C_{18}H_{21}N_5O_2$-2HCl 1/2 $H_2O$):

|  | C | H | N |
|---|---|---|---|
| Theoretical (%) | 46.74 | 6.29 | 18.17 |
| Found (%) | 46.44 | 6.40 | 17.90 | b. Synthesis of 2-[$N^4$-(2-furoyl)homopiperazino]-4-amino-6,7-dimethoxy-quinazoline A solution of 3 g of 2-homopiperazino-4-amino-6,7-dimethoxy-quinazoline in 60 ml of acetone is added dropwise to a solution of 1.3 g of 2-furancarboxylic acid chloride in 30 ml of acetone under stirring and ice-cooling. After completion of the addition, the stirring is continued for additional one hour to complete the reaction. The crystals thus precipitated are filtered out and recrystallized from a mixture of methanol and ethanol.

Yield: 3.1 g (70.4%)

Melting point: 278–280° C.

Elementary analysis (as $C_{20}H_{23}N_3O_4$ HCl):

|  | C | H | N |
|---|---|---|---|
| Theoretical (%) | 55.36 | 5.59 | 16.15 |
| Found (%) | 55.30 | 5.45 | 16.18 |

Example 111

Synthesis of 2-($N^4$-homopiperazino)-4-amino-6,7-dimethoxy-quinazoline

2 Grams of triethylamine are added to a solution of 1.5 g of 2-homopiperazino-4-amino-6,7-dimethoxy-quinazoline and 1.5 g of α-butyl chloride in 20 ml of n-butanol and the mixture is refluxed under stirring for 24 hours. After completion of the reaction, the solvent is distilled off and then the thus obtained residue is made alkaline by addition of 10% aqueous caustic soda solution. The oily substance thus separated out is extracted with chloroform. The extract is washed with water, dried with potassium carbonate and filtered. The filtrate is concentrated. The residue thus obtained is dissolved in 30 ml of isopropanol. The solution is added with 3 ml of saturated isopropanol/hydrochloric acid and the resulting crystals are filtered out and recrystallized from a mixture of methanol/ethanol. The aimed compound is obtained as dihydrochloride.

Yield: 0.9 g (50.6%)

Elementary analysis (as $C_{10}H_{23}N_2O_4 \cdot 2HCl \cdot 1/2 H_2O$)

|  | C | H | N |
|---|---|---|---|
| Theoretical (%) | 51.68 | 7.32 | 15.86 |
| Found (%) | 51.74 | 7.13 | 16.42 |

Examples 112 to 126

Various compounds shown in Table 1 were obtained by the methods similar to those used in Examples 110 and 111.

The results are summarized in Table 1.

TABLE 1

| Example | Molecular formula M.P. (°C.) | Elementary analysis (%) Theoretical | | |
|---|---|---|---|---|
|  |  | | | Found |
| 112 | $C_{17}H_{19}N_3O_3$—HCl—$H_2O$ | 51.05 | 6.57 | 17.52 |
|  | 235–240 | 51.16 | 6.34 | 17.8 |
| 113 | $C_{19}H_{17}N_3O_3$—HCl—½$H_2O$ | 54.46 | 6.99 | 16.71 |
|  | 240–250 | 54.20 | 6.97 | 17.18 |
| 114 | $C_{19}H_{17}N_3O_3$—HCl | 55.66 | 6.90 | 17.09 |
|  | 280–282 | 55.40 | 6.89 | 16.79 |
| 115 | $C_{23}H_{24}ClN_3O_3$—HCl—$H_2O$ | 53.22 | 5.49 | 14.11 |
|  | 235–240 | 53.18 | 5.79 | 13.61 |
| 116 | $C_{23}H_{27}N_3O_4$—HCl | 58.27 | 5.97 | 14.78 |
|  | 225–235 | 57.78 | 6.09 | 14.32 |
| 117 | $C_{23}H_{27}N_3O_1S$—HCl | 52.91 | 5.42 | 13.42 |
|  | 270–272 | 52.98 | 5.44 | 13.45 |
| 118 | $C_{24}H_{28}N_2O_3$—HCl—½$H_2O$ | 56.18 | 6.10 | 13.65 |
|  | 220–225 | 56.06 | 6.29 | 13.46 |
| 119 | $C_{94}H_{97}N_3O_3$—HCl—$H_2O$ | 59.06 | 6.21 | 14.35 |
|  | 210–215 | 58.65 | 5.82 | 14.20 |
| 120 | $C_{24}H_{22}N_3O_3$—HCl—$H_2O$ | 55.17 | 5.61 | 13.41 |
|  | 245–250 | 55.62 | 5.46 | 13.83 |
| 121 | $C_{23}H_{29}N_3O_3$—HCl—½$H_2O$ | 57.51 | 5.42 | 13.42 |
|  | 235–240 | 57.80 | 5.62 | 13.52 |
| 122 | $C_{27}H_{31}N_2O_2$—HCl—½$H_2O$ | 57.18 | 5.88 | 12.35 |
|  | 292–294 | 57.52 | 6.06 | 12.41 |
| 123 | $C_{10}H_{22}N_2O_2$ | 60.54 | 7.32 | 22.07 |
|  | 208–210 | 60.37 | 7.22 | 22.07 |
| 124 | $C_{22}H_{22}Cl_2N_2O_2$—2HCl | 49.35 | 5.09 | 13.08 |
|  | 240–245 | 49.44 | 5.56 | 12.52 |
| 125 | $C_{22}H_{22}N_2O_2$—2HCl | 55.63 | 6.31 | 14.11 |
|  | 280–285 | 55.59 | 6.36 | 14.34 |
| 126 | $C_{22}H_{22}N_2O_2$—3HCl | 51.01 | 6.04 | 16.23 |
|  | 250–260 | 50.52 | 6.30 | 15.90 |

Example 127

4-Amino-2-[4-(cyclopentylcarbonyl)-1-piperazinyl]-6,7-dimethoxyquinazoline a. A mixture of N-(cyclopentylcarbonyl) piperazine (3.6 g., 0.02 mole) and 2-chloro-4-amino-6,7-dimethoxyquinazoline (4.79 g., 0.02 mole) in 50 ml. of absolute ethanol is heated in an enclosed reactor at 170° C. for a period of 16 hours. The reaction mixture is cooled, filtered and insolubles triturated with 100 ml. of concentrated ammonium hydroxide to provide the free base. The insoluble product is collected and crystallized from methanol to afford analytically pure 4-amino-2-[4-cyclopentylcarbonyl)-1-piperazinyl]-6,7-dimethoxyquinazoline, m.p. 256.0° C. (corr.).

Analysis. Calcd. for $C_{20}H_{27}N_5O_3$ (percent): C, 62.32; H, 7.06; N, 18.17. Found (percent): C, 62.06; H, 7.24; N, 17.99.

Example 127(a) illustrates the procedure of Equation 1 of U.S. Pat. No. 4,060,615 to Matier et al., which is incorporated herein by reference, while the following Examples 127(b–e) illustrate procedures of Equations 2–5 of U.S. Pat. No. 4,060,615, respectively, for the preparation of 4-amino-2-[4-(cyclopentyl-carbonyl)-1-piperazinyl]-6,7-dimethoxyquinazoline.

b. Cyclopentylcarbonyl chloride (0.1 mole) is added to 0.1 mole of 4-amino-2-(1-piperazinyl)-6,7-dimethoxyquinazoline in 300 ml. of methanol with vigorous stirring at room temperature. Stirring is continued for a period of 2 to 6 hours and the product is isolated according to the procedure of Example 127(a) to provide 4-amino-2-[4-(cyclopentylcarbonyl)-1-piperazinyl]-6,7-dimethoxyquinazoline. If the hydrochloride salt is desired, the base treatment is omitted and evaporation of the solvent provides 4-amino-2-[4-(cyclopentylcarbonyl)-piperazinyl]-6,7-dimethoxyquinazoline hydrochloride, m.p. 279°–280° C. (dec.)(corr.) crystallized from methanol-isopropanol.

Analysis. Calcd. for $C_{20}H_{27}N_5O_3 \cdot HCl$ (percent): C, 56.93; H, 6.69; N, 16.60. Found (percent): C, 56.65; H, 6.89; N, 16.44.

c. A mixture of anhydrous ammonia and 4-chloro-2-[4-(cyclopentylcarbonyl)-1-piperazinyl]-6,7-dimethoxyquinazoline in 100 ml. of tetrahydrofuran is heated at 100° C. for a period of 16 to 24 hours and the product isolated according to the procedure of Example 127(a) to provide 4-amino-2-[4-(cyclopentylcarbonyl)-1-piperazinyl]-6,7-dimethoxyquinazoline.

d. A mixture of 4-amino-2-methylmercapto-6,7-dimethoxyquinazoline (0.1 mole) and from 0.1 to 0.15 mole of N-(cyclopentylcarbonyl)piperazine in 150 ml. of isoamyl alcohol is refluxed for a period of 8 to 24 hours. The solvent is evaporated and residual material, treated according to procedure of Example 127(a), provides 4-amino-2-[4-(cyclopentylcarbonyl)-1-piperazinyl]-6,7-dimethoxyquinazoline.

e. Ethyl-4-(cyclopentylcarbonyl)piperazin-1-yl-formamidate hydrochloride (0.01 mole) is added to a solution of 4,5-dimethoxy-2-aminobenzonitrile (0.01 mole) in 30 ml. of N,N-dimethylformamide. Sodium hydride (0.02 mole of a 56% suspension in mineral oil) is added and the mixture stirred 0.5 hr. at room temperature and then at 100° C. for a period of 12 hr. When the reaction period is complete, water is added providing 4-amino-2-[4-cyclopentylcarbonyl)-1-piperazinyl]-6,7-dimethoxyquinazoline.

Example 128

4-Amino-2-[4-(cyclopropylcarbonyl)-1-piperazinyl]-6,7-dimethoxyquinazoline

N-(Cyclopropylcarbonyl)piperazine (3.08 g., 0.02 mole) and 2-chloro-4-amino-6,7-dimethoxyquinazoline (4.74 g., 0.02 mole) are reacted according to the procedure of Example 127(a). The crude product crystallized from ethanol affords analytically pure 4-amino-2-[4-(cyclopropylcarbonyl)-1-piperazinyl]-6,7-dimethoxyquinazoline, m.p. 283.5° C. (corr.).

Analysis, Calcd. for $C_{18}H_{23}N_5O_3$ (percent): C, 60.49; H, 6.49; N, 19.59. Found (percent): C, 60.56; H, 6.46; N, 19.41.

Example 129

4-Amino-2-[4-(cyclohexylcarbonyl)-1-piperazinyl]-6,7-dimethoxyquinazoline

N-(Cyclohexylcarbonyl)piperazine (5.9 g., 0.03 mole) and 2-chloro-4-amino-6,7-dimethoxyquinazoline (7.2 g., 0.03 mole) are reacted according to the procedure of Example 127(a). The crude product crystallized from methanol affords analytically pure 4-amino-2-4-(cyclohexylcarbonyl)-1-piperazinyl]-6,7-dimethoxyquinazoline, m.p. 223°–225° C., resolidifying and remelting at 248.0°–250.0° C. (corr.)

Analysis. Calcd. for $C_{21}H_{29}N_5O_3$ (percent): C, 63.14; H, 7.32; N, 17.53. Found (percent): C, 63.07; H, 7.43; N, 17.63.

Example 130

4-Amino-2-[4-(cyclopenten-1-ylcarbonyl)-piperazinyl]-6,7-dimethoxyquinazoline

N-(1-cyclopenten-1-ylcarbonyl)piperazine (1.8 g., 0.01 mole) and 2-chloro-4-amino-6,7-dimethoxyquinazoline (2.4 g., 0.01 mole) are reacted according to the procedure of Example 127(a). The isolated product crystallized from methanol affords analytically pure 4-amino-2-[4-(1-cyclopenten-1-ylcarbonyl)piperazinyl]-6,7-dimethoxyquinazoline, m.p. 256.5°–258.0° C. (corr.).

Analysis. Calcd. for $C_{20}H_{25}N_5O_3$ (percent): C, 62.65; H, 6.57; N, 18.26. Found (percent): C, 65.23; H, 6.56; N, 18.42.

Example 131

4-Amino-2-[4-(3-cyclopentenylcarbonyl)-1-piperazinyl-6,7-dimethoxyquinazoline

N-(3-cyclopentenylcarbonyl)piperazine (2.7 g., 0.015 mole) and 2-chloro-4-amino-6,7-dimethoxyquinazoline (3.6 g., 0.015 mole) are reacted according to the procedure of Example 127(a). The crude product crystallized from methanol affords analytically pure 4-amino-2-4-(3-cyclopentenylcarbonyl)-1-piperazinyl]-6,7-dimethoxyquinazoline, m.p. 215.5°–217.5° C. (corr.).

Analysis. Calcd. for $C_{20}H_{25}N_5O_3$ (percent): C, 62.65; H. 6.57; N, 18.26. Found (percent): C, 62.35; H, 6.72; N, 18.21.

Example 132

4-Amino-2-[4-(3-cyclohexenylcarbonyl)-1-piperazinyl]-6,7-dimethoxyquinazoline

N-(3-cyclohexenylcarbonyl)piperazine (7.65 g., 0.04 mole) and 2-chloro-4-amino-6,7-dimethoxyquinazoline (9.6 g., 0.04 mole) are reacted according to the procedure of Example 127(a). The crude product crystallized from methanol affords analytically pure 4-amino-2-[4-(3-cyclohexenlcarbonyl)-1-piperazinyl]-6,7-dimethoxyquinazoline, m.p. 211°–213° C. resolidifying and melting at 234.0°–236.0° C. (corr.).

Analysis. Calcd. for $C_{21}H_{27}N_5O_3$ (percent): C, 63.46; H, 6.85; N, 17.62. Found (percent): C, 63.18; H, 6.80; N, 17.63.

Example 133

4-Amino-2-[4-(cyclobutylcarbonyl)-1-piperazinyl]-6,7-dimethoxyquinazoline Hydrochloride N-(Cyclobutylcarbonyl)piperazine (0.02 mole) and 2-chloro-4-amino-6,7-dimethoxyquinazoline (0.02 mole) are reacted according to the procedure of Example 127(a). When reaction is complete, the solvent is removed and the residue crystallized from methanolisopropanol to provide analytically pure 4-amino-2-[4-(cyclobutylcarbonyl)-1-piperazinyl]-6,7-dimethoxyquinazoline hydrochloride hydrate, m.p. 267°–268° C. (dec.)(corr.).

Analysis. Calcd. for $C_{19}H_{25}N_5O_3 \cdot HCl \cdot 1/4 H_2O$ (percent): C, 55.33; H, 6.48; N, 16.98. Found (percent): C, 55.49; H, 6.75; N, 16.62.

Example 134

4-Amino-2-[4-(cycloheptylcarbonyl)-1-piperazinyl]-6,7-dimethoxyquinazoline Hydrochloride N-(Cycloheptylcarbonyl)piperazine (0.02 mole) and 2-chloro-4-amino-6,7-dimethoxyquinazoline (0.02 mole) are reacted according to the procedure of Example 133. Crystallization of the product from methanol-isopropanol provides analytically pure 4-amino-2-[4-(cycloheptylcarbonyl)-1-piperazinyl]-6,7-dimethoxyquinazoline hydrochloride, m.p. 278°–279° C. (corr.).

Analysis. Calcd. for $C_{22}H_{31}N_5O_3 \cdot HCl$ (percent): C, 58.72; H, 7.17; N, 15.56. Found (percent): C, 58.73; H, 7.39; N, 15.44.

Example 135

Following the procedure of Example 127 but employing an equimolar amount of:
N-(2-cyclopentenylcarbonyl)piperazine,
N-(1-cyclohexen-1-ylcarbonyl)piperazine,
(1-cyclohexen-1-ylcarbonyl)piperazine,
N-(cyclooctylcarbonyl)piperazine,
N-(2-methylcyclopentylcarbonyl)piperazine,
N-(1-methylcyclopentylcarbonyl)piperazine,
N-(1-methylcyclohexylcarbonyl)piperazine,
in place of N-(cyclopentylcarbonyl)piperazine, there is produced:

a. 4-amino-2-[4-(2-cyclopentenylcarbonyl)1-piperazinyl]-6,7-dimethoxyquinazoline.
b. 4-amino-2-[4-(1-cyclohexen-1-ylcarbonyl)-1-piperazinyl]-6,7-dimethoxyquinazoline,
c. 4-amino-2-[4-(cyclooctylcarbonyl)-1-piperazinyl]-6,7-dimethoxyquinazoline,
d. 4-amino-2-[4-(2-methylcyclopentylcarbonyl)-1-piperazinyl]-6,7-dimethoxyquinazoline.
e. 4-amino-2-[4-(1-methylcyclopentylcarbonyl)-1-piperazinyl]-6,7-dimethoxyquinazoline,
f. 4-amino-2-[4-(1-methylcyclohexylcarbonyl)-1-piperazinyl]-6,7-dimethoxyquinazoline.

Example 136

4-Hydrazino-2-[4-(cyclopentylcarbonyl)-1-piperazinyl]-6,7-dimethoxyquinazoline Hydrochloride N-(Cyclopentylcarbonyl)piperazine (0.02 mole) and 2-chloro-4-hydrazino-6,7-dimethoxyquinazoline (0.02 mole) reacted according to the procedure of Example 133 provides 4-hydrazino-2-[4-(cyclopentylcarbonyl)-1-piperazinyl]-6,7-dimethoxyquinazolinehydrochloride, m.p. 282°–284° C.

Example 137

Suspensions

A suspension of 4-amino-2-[4-(cyclopentyl-carbonyl)-1-piperazinyl]-6,7-dimethoxyquinazoline or a pharmaceutically acceptable salt thereof is prepared with the following ingredients:

Active ingredient: 20 g.
Sucrose, U.S.P.: 400 g.
Sorbitol, U.S.P.: 100 g.
Bentonite: 20 g.
Flavors, q.s.
Water, distilled to make 1 liter Each milliliter of the suspension contains approximately 20 mg. of the active ingredient.

Example 138

Tablets

The following ingredients are blended in the proportion by weight indicated according to conventional pharmaceutical techniques to provide a tablet base:

Lactose: 79
Corn Starch: 10
Talcum: 6
Tragancanth: 4
Magnesium Stearate: 1

This tablet base is blended with sufficient 4-amino-2-[4-(cyclopentylcarbonyl)-1-piperazinyl]-6,7-dimethoxyquinazoline or a pharmaceutically acceptable salt thereof to provide tablets containing 0.1, 0.25, 0.5, 1, 2.5, 5, 7.5, 10, 25, and 50 mg. of active ingredient; formed in a tablet of the desired size in a conventional tablet press.

Example 139

Dry Filled Capsules

The following ingredients are blended in a conventional manner in the proportion by weight indicated.

Lactose, U.S.P.: 50
Starch: 5
Magnesium Stearate: 2

Sufficient 4-amino-2-[4-(cyclopentylcarbonyl)-1-piperazinyl]-6,7-dimethoxyquinazoline or a pharmaceutically acceptable salt thereof is added to the blend to provide capsules containing 0.1, 0.25, 0.5, 1, 2.5, 5, 7.5, 10, 25, and 50 mg. of active ingredient, and filled into hard gelatin capsules of a suitable size.

It will be understood that various changes and modifications can be made in the details of procedure, formulation and use without departing from the spirit of the invention, especially as defined in the following claims.

We claim:

1. A method of treating a patient having precancerous lesions sensitive to compounds below and in the need of treatment, comprising administering to the patient a pharmacologically effective amount of a compound of the formula:

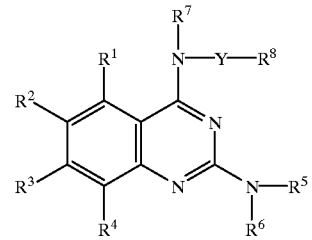

wherein R1, R2, R3 and R4, each of which may be the same or different, are selected from a hydrogen atom, a halogen atom, an alkoxy group having from 1 to 6 carbon atoms, or a cyano group R5 and R6 form a piperidino group which may be substituted;

R7 is selected from a hydrogen atom or an alkyl group having 1 to 6 carbon atoms;

R8 is a benzyl group which may be substituted, said substitutions, which may be the same or different, are selected from a hydrogen atom, a halogen atom, a hydroxyl group, an amino group, a nitro group, an alkyl group having from 1 to 6 carbon atoms, an alkoxy group having from 1 to 6 carbon atoms, an alkoxyalkyl group having from 2 to 8 carbon atoms, an alkenyl group having from 2 to 8 carbon atoms, an acyl group, an acylamino group, an alkylsulfonylamino group, a hydroiminoalkyl group, an alkyloxycarbonylamino group, an alkyloxybarbonyloxy group or a heteroaryl group which may be substituted; or two of said substitutions may together form a methylenedioxy group; and Y is a group represented by the formula —(CH2)q— (wherein q is 0 or an integer of 1 to 8), when q is an integer of 1 to 8, each carbon atom may have from 1 to 2 substituents.

2. The method of claim 1, wherein R2 is a halogen atom.

3. The method of claim 2, wherein R2 is a chlorine atom.

4. The method of claim 3, wherein R1, R3 and R4 are hydrogen atoms.

5. The method of claim 1, wherein R7 is a hydrogen atom.

6. The method of claim 5, wherein R5 and R6 form a ring represented by the formula:

wherein R9 is selected from a hydroxyl group which may be protected, a halogen atom, a alkyl group having 1 to 8 carbon atoms, a lower alkoxy group, a carboxyl group which may be protected, a hydroxyalkyl group, a carboxyalkyl group and a heteroacyl group.

7. The method of claim 5, wherein said compound is 2-(4-Carboxypiperidino)-4-(3,4-methylenedioxybenzyl)amino-6-chloroquinazolin.

8. The method of claim 1, wherein R8 is a group represented by the formula:

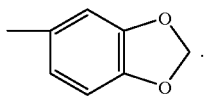

9. The method of claim 8, wherein one of R1, R2, R3 and R4 is a cyano group, a chlorine atom or a methoxy atom.

10. The method of claim 9, wherein R2 is a halogen atom.

11. The method of claim 10, wherein R2 is a chlorine atom.

12. The method of claim 11, wherein R1, R3 and R4 are hydrogen atoms.

13. The method of claim 12, wherein R5 and R6 form a ring which is represented by the formula:

wherein R9 is selected from a hydroxyl group which may be protected, a halogen atom, a alkyl group having 1 to 8 carbon atoms, a lower alkoxy group, a carboxyl group which may be protected, a hydroxyalkyl group, a carboxyalkyl group and a heteroacyl group.

14. The method for inhibiting the growth of neoplastic cells sensitive to a compound below, comprising exposing said cells to an effective amount of a compound of the formula:

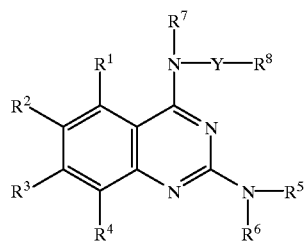

wherein R1, R2, R3 and R4, each of which may be the same or different, are selected from a hydrogen atom, a halogen atom, an alkoxy group having from 1 to 6 carbon atoms, or a cyano group;

R5 and R6 form a piperidino group which may be substituted;

R7 is selected from a hydrogen atom or an alkyl group having 1 to 6 carbon atoms;

R8 is a benzyl group which may be substituted, said substitutions, which may be the same or different, are selected from a hydrogen atom, a halogen atom, a hydroxyl group, an amino group, a nitro group, an alkyl group having from 1 to 6 carbon atoms, an alkoxy group having from 1 to 6 carbon atoms, an alkoxyalkyl group having from 2 to 8 carbon atoms, an alkenyl group having from 2 to 8 carbon atoms, an acyl group, an acylamino group, an alkylsulfonylamino group, a hydroiminoalkyl group, an alkyloxycarbonylamino group, an alkyloxybarbonyloxy group or a heteroaryl group which may be substituted; or two of said substitutions may together form a methylenedioxy group; and Y is a group represented by the formula —(CH2)q— (wherein q is 0 or an integer of 1 to 8), when q is an integer of 1 to 8, each carbon atom may have from 1 to 2 substituents.

15. The method of claim 14 wherein R1, R2, R3 and R4 may independently be a cyano group, a halogen or a methoxy group.

16. The method of claim 15, wherein R2 is a halogen.

17. The method of claim 16, wherein R8 is represented by the formula:

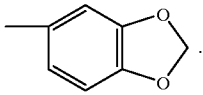

18. The method of claim 17, wherein R5 and R6 form a ring which is represented by the formula:

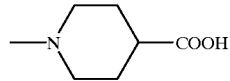

19. The method of claim 18, wherein said compound is 2-(4-Carboxypiperidino)-4-(3,4-methylenedioxybenzyl)amino-6-chloroquinazolin.

* * * * *